US010556015B2

(12) United States Patent
Zhang et al.

(10) Patent No.: US 10,556,015 B2
(45) Date of Patent: Feb. 11, 2020

(54) LYSOSOMAL TARGETING OF ENZYMES, AND USES THEREOF

(71) Applicant: Shire Human Genetic Therapies, Inc., Lexington, MA (US)

(72) Inventors: Bohong Zhang, Lexington, MA (US); Michael F. Concino, Lexington, MA (US)

(73) Assignee: Criteo S.A., Paris (FR)

( * ) Notice: Subject to any disclaimer, the term of this patent is extended or adjusted under 35 U.S.C. 154(b) by 0 days.

(21) Appl. No.: 15/521,130

(22) PCT Filed: Oct. 23, 2015

(86) PCT No.: PCT/US2015/057214
§ 371 (c)(1),
(2) Date: Apr. 21, 2017

(87) PCT Pub. No.: WO2016/065319
PCT Pub. Date: Apr. 28, 2016

(65) Prior Publication Data
US 2017/0333569 A1    Nov. 23, 2017

Related U.S. Application Data

(60) Provisional application No. 62/068,033, filed on Oct. 24, 2014.

(51) Int. Cl.
| | |
|---|---|
| *A61K 47/65* | (2017.01) |
| *C12N 9/64* | (2006.01) |
| *C12N 9/24* | (2006.01) |
| *A61K 47/64* | (2017.01) |
| *C12N 9/96* | (2006.01) |
| *C12N 15/62* | (2006.01) |

(52) U.S. Cl.
CPC .............. *A61K 47/65* (2017.08); *A61K 47/64* (2017.08); *C12N 9/2402* (2013.01); *C12N 9/6454* (2013.01); *C12N 9/96* (2013.01); *C12N 15/62* (2013.01); *C12Y 302/0102* (2013.01); *C12Y 302/0105* (2013.01); *C07K 2319/06* (2013.01); *C07K 2319/50* (2013.01)

(58) Field of Classification Search
CPC ...... A61K 47/65; A61K 47/64; C12N 9/2402; C12N 9/6454; C12N 9/96; C12N 15/62; C12Y 302/0102; C12Y 302/0105; C07K 2319/06; C07K 2319/50
USPC ........................................................ 424/94.1
See application file for complete search history.

(56) References Cited

U.S. PATENT DOCUMENTS

| | | | |
|---|---|---|---|
| 2005/0281805 A1 | 12/2005 | Lebowitz et al. | |
| 2011/0003315 A1* | 1/2011 | Seidah | .................. C07K 16/40 435/7.21 |
| 2011/0223147 A1* | 9/2011 | Lebowitz | ............... C07K 14/65 424/94.3 |
| 2011/0318327 A1* | 12/2011 | Concino | ............. A61K 9/0085 424/94.61 |

FOREIGN PATENT DOCUMENTS

| | | | | |
|---|---|---|---|---|
| EP | 2471929 | * | 7/2012 | ............. C12N 15/82 |
| WO | 03/102583 A1 | | 12/2003 | |
| WO | 2005/078077 A2 | | 8/2005 | |
| WO | 2009/137721 A2 | | 11/2009 | |
| WO | 2010/148253 A2 | | 12/2010 | |
| WO | 2011/163652 A2 | | 12/2011 | |
| WO | 2014/085621 A1 | | 6/2014 | |

OTHER PUBLICATIONS

Desnick et al., Enzyme Replacement Therapy for Lysosomal Diseases: Lessons from 20 Years of Experience and Remaining Challenges, Annu. Rev. Genom. Human Genet., 2012, 13:307-335.*
Kourimate et al., Cellular and secreted pro-protein convertase subtilisin/kexin type 9 catalytic activity in hepatocytes, Atherosclerosis, 206 (2009), pp. 134-140.*
Bosshart, H. et al., "The cytoplasmic domain mediates localization of furin to the trans-Golgi network en route to the endosomal/lysosomal system", J Cell Biol., 126(5): 1157-1172 (1994).
DeVay, R. M. et al., "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)", J Biol Chem., 288(15): 10805-18 (2013).
Wolins N. et al., "The luminal domain of furin mediates in aggregation in the trans-Golgi network and targeting to lysosomes", Molecular Biology of the Cell, & 37th Annual Meeting of the American Society for Cell Biology; Washington, D.C., USA; Dec. 13-17, vol. 8, Suppl., p. 422a (1997).
Wolins N. et al., "Aggregation as a Determinant of Protein Fate in Post-Golgi Compartments: Role of the Luminal Domain of Furin in Lysosomal Targeting", J Cell Biol, 139(7): 1735-1745 (2007).

* cited by examiner

*Primary Examiner* — Jennifer M. H. Tichy
(74) *Attorney, Agent, or Firm* — Proskauer Rose LLP; Fangli J. D. Chen; Julio J. Mendez

(57) ABSTRACT

The invention provides compositions and methods for effective lysosomal targeting mediated by PCSK9. In particular, the compositions and methods provided by the invention may be used to treat lysosomal storage diseases such as Pompe Disease and Sanfilippo Syndrome Type B, and they may be used for targeting lysosomal enzymes to the various muscles of the human body.

5 Claims, No Drawings

Specification includes a Sequence Listing.

LYSOSOMAL TARGETING OF ENZYMES, AND USES THEREOF

CROSS-REFERENCE TO RELATED APPLICATIONS

This application is the U.S. National Stage Entry claiming priority and benefit to International Application PCT/US15/57214 filed on Oct. 23, 2015; which claims priority and benefit to U.S. Provisional Application No. 62/068,033 filed Oct. 24, 2014, the disclosures of each of which are hereby incorporated by reference in their entireties for all purposes.

BACKGROUND

More than forty lysosomal storage diseases are caused, directly or indirectly, by the absence or deficiency of one or more lysosomal enzymes.

Pompe disease is a lysosomal storage disease caused by a deficiency or dysfunction of the lysosomal hydrolase acid alpha-glucosidase (GAA), a glycogen-degrading lysosomal enzyme. Deficiency of GAA results in lysosomal glycogen accumulation in many tissues, with cardiac and skeletal muscle tissues being most seriously affected. The combined incidence of all forms of Pompe disease is estimated to be 1:40,000. It is estimated that approximately one third of patients with Pompe disease have the rapidly progressive, fatal infantile-onset form, while the majority of patients present with the more slowly progressive, juvenile or late-onset forms.

Sanfilippo syndrome, or mucopolysaccharidosis III (MPS III), on the other hand, is a rare genetic disorder characterized by the deficiency of enzymes involved in the degradation of glycosaminoglycans (GAG). Four distinct forms of MPS III, designated MPS IIIA, B, C, and D, have been identified. Each is characterized by the absence or deficiency of a different lysosomal enzyme. Mucopolysaccharidosis type IIIB (MPS IIIB; Sanfilippo B disease) is an autosomal recessive disorder that is caused by a deficiency of the enzyme alpha-N-acetyl-glucosaminidase (Naglu), resulting in the accumulation of heparan sulfate in lysosomes of particularly neurons and glial cells in the brain, with additional lysosomal accumulation of heparan sulfate elsewhere. MPS IIIB manifests itself primarily in the brain.

Enzyme replacement therapy (ERT) has been used to deliver enzymes for the treatment of various lysosomal storage diseases. Normally, lysosomal enzymes are synthesized in the cytosol and then traverse the endoplasmic reticulum (ER), where they are glycosylated with N-linked, high mannose type carbohydrates. In the Golgi apparatus, high mannose carbohydrates on glycoproteins are then modified by a series of glycotransferases to become mature N-glycan; one of these modifications is the addition of mannose-6-phosphate (M6P). Proteins carrying this modification are then targeted to the lysosome via binding of the M6P moiety to the cation-independent mannose-6-phosphate receptor (CI-M6PR) and cation-dependant mannose-6-phoshate receptor (CD-M6PR).

Efficacy of enzyme replacement therapy is critically dependent on proper lysosomal targeting of the replacement enzyme. However, recombinantly produced Naglu protein is characterized by a dramatic lack of M6P phosphorylation, making lysosomal targeting of this enzyme and its effective use for ERT very difficult. Similarly, for some diseases, such as Pompe, enzyme replacement therapy has shown limitations, such as limited clinical benefit resulting from poor cellular uptake of recombinant enzyme in skeletal muscle and cardiac tissues of the body (Schoser et al., Neurotherapeutics 5:569-578 (2008)).

Therefore, there remains a need to develop alternative methods for lysosomal targeting to ensure effective enzyme replacement therapy.

SUMMARY

The present invention provides an alternative lysosomal targeting approach for enzyme replacement therapy that is more efficient, reliable and consistent. The present invention is, in part, based on the surprising discovery that a replacement enzyme can be effectively delivered to the lysosome through the use of a soluble extracellular protein, such as PCSK9, and its interaction with various secondary binding proteins, such as, but not limited to, amyloid precursor-like protein 2 (APLP2), Dynamin, amyloid precursor protein (APP), autosomal recessive hypercholesterolemia (ARH) protein or low density lipoprotein receptor-related protein 8 (Lrp8). Thus, the present invention permits targeting of a therapeutic to a lysosome in a glycosylation or M6P-independent manner and can be used to deliver enzymes with low levels of glycosylation or even with complete absence of glycosylation. Accordingly, the present invention allows for simpler processes of manufacturing recombinant enzymes for enzyme replacement therapy. Since PCSK9 is ubiquitously expressed throughout the various tissues of the body, the invention provides an effective means for delivering replacement enzymes for diseases associated with the nervous system and/or other tissues inn the body. Furthermore, many of PCSK9's potential cognate transmembrane binding partners, i.e., APLP2 and Dynamin, are known to be enriched in human skeletal muscle and tissues of the kidney (The Human Protein Atlas; Uhlen et al. Nat Biotechnol. 2010 28(12):1248-50. Uhlén et al. Mol Cell Proteomics. 2005 4(12):1920-32. Pontén et al. J Pathol. 2008 216(4): 387-93. Lundberg et al. Mol Syst Biol. 2010 6:450. Pontén et al. Mol Syst Biol. 2009 5:337), which means that the invention provides an effective means for treating lysosomal storage diseases that affect these tissues, such as Pompe disease.

In one aspect, the present invention provides a targeted therapeutic including a lysosomal enzyme and a lysosomal targeting moiety including a proprotein convertase protein or fragment thereof.

In some embodiments, the lysosomal enzyme is selected from Table 3.

In some embodiments, the lysosomal enzyme is an acid alpha-glucosidase (GAA) protein. In some embodiments, the GAA protein comprises an amino acid sequence at least 80%, 90%, or 95% identical to SEQ ID NO:1. In some embodiments, the GAA protein comprises an amino acid sequence identical to SEQ ID NO:1.

In some embodiments, the lysosomal enzyme is an alpha-N-acetylglucosaminidase (Naglu) protein. In some embodiments, the Naglu protein comprises an amino acid sequence at least 80%, 90%, or 95% identical to SEQ ID NO:4. In some embodiments, the Naglu protein comprises an amino acid sequence identical to SEQ ID NO:4.

In some embodiments, the proprotein convertase protein is selected from the group consisting of PC1/3; PC2; Furin; PC4; PC5/6; PACE4, PC7, SKI-1/S1P and PCSK9. In some embodiments, the proprotein convertase comprises an amino acid substitution selected from the group consisting of S386A, F379A and a combination thereof. In some embodiments, the proprotein convertase is a PCSK9 protein.

In some embodiments, the PCSK9 protein comprises an amino acid sequence at least 80%, 90% or 95% identical to SEQ ID NO:7. In some embodiments, the PCSK9 protein comprises an amino acid sequence is identical to SEQ ID NO:7.

In some embodiments, the targeted therapeutic is a fusion protein. In some embodiments, the lysosomal targeting moiety is fused to the N-terminus or C-terminus of the lysosomal enzyme. In some embodiments, the lysosomal targeting moiety and the lysosomal enzyme are fused via a linker. In some embodiments, the linker is a peptide linker. In some embodiments, the peptide linker comprises a cleavage site. In some embodiments, the cleavage site comprises a lysosomal protease recognition site. In some embodiments, the linker comprises a sequence of GAPGGGGGAAAAAGGGGGGAPGGGGGAAAAAG-GGGGGAPGGGGGAAAAAGGGGG GAP (SEQ ID NO. 13). In some embodiments, the fusion protein comprises a sequence at least 80%, 90% or 95% identical to the amino acid sequence of SEQ ID NO. 21 or 22. In some embodiments, the fusion protein comprises a sequence identical to the amino acid sequence of SEQ ID NO. 21 or 22.

In some embodiments, the targeted therapeutic comprises an auxiliary propeptide derived from a proprotein convertase protein a fragment thereof. In some embodiments, the auxiliary propeptide is derived from a proprotein convertase protein selected from the group consisting of PC1/3; PC2; Furin; PC4; PC5/6; PACE4, PC7, SKI-1/S1P and PCSK9. In some embodiments, the auxiliary propeptide is derived from PCSK9. In some embodiments, the auxiliary propeptide comprises a sequence at least 80%, 90% or 95% identical to the amino acid sequence of SEQ ID NO. 23. In some embodiments, the auxiliary propeptide comprises a sequence identical to the amino acid sequence of SEQ ID NO. 23. In some embodiments, the targeted therapeutic has a higher binding affinity for Amyloid Precursor-like Protein 2 (APLP2), Dynamin, Amyloid Precursor Protein (APP), Autosomal Recessive Hypercholesterolemia (ARH) protein, or Low Density Lipoprotein Receptor-related Protein 8 (Lrp8), than for an LDL receptor. In some embodiments, the targeted therapeutic has a binding affinity for Amyloid Precursor-like Protein 2 (APLP2), Dynamin, Amyloid Precursor Protein (APP), Autosomal Recessive Hypercholesterolemia (ARH) protein, or Low Density Lipoprotein Receptor-related Protein 8 (Lrp8) that is at least 2, 3, 4, 5, 6, 7, 8, 9 or 10 fold higher than for an LDL receptor.

In one aspect, the present invention provides a nucleic acid encoding any of the proteins disclosed herein.

In one aspect, the present invention provides a vector including any of the nucleic acids disclosed herein.

In one aspect, the present invention provides a host cell including any of the vectors disclosed herein. In some embodiments, the host cell is selected from a bacterial, yeast, insect or mammalian cell. In some embodiments, the host cell is a mammalian cell. In some embodiments, the the mammalian cell is a human cell. In some embodiments, the mammalian cell is a CHO cell.

In one aspect, the present invention provides a method of producing a targeted therapeutic, the method including steps of a) culturing any of the host cells disclosed herein under conditions suitable for expression of the targeted therapeutic by the host cell; and b) harvesting the targeted therapeutic expressed by the host cell. In some embodiments, any of the fusion proteins disclosed herein and an auxiliary protein are cultured within the same host cell. In some embodiments, the fusion protein and the auxiliary protein are harvested from the host cell simultaneously.

In one aspect, the present invention provides a pharmaceutical composition comprising any of the targeted therapeutics disclosed herein, and a pharmaceutical acceptable carrier.

In one aspect, the present invention provides a method of treating a lysosomal storage disease including administering to a subject in need of treatment any of the pharmaceutical compositions disclosed herein. In some embodiments, the lysosomal storage disease is selected from Table 3. In some embodiments, the lysosomal storage disease is Pompe disease or Sanfilippo syndrome type B. In some embodiments, the pharmaceutical composition is administered intravenously, intramuscularly, subcutaneously, intrathecally and/or combinations thereof.

In one aspect, the present invention provides a method of delivering a targeted therapeutic to skeletal muscle, vascular smooth muscle or cardiac muscle, including administering to a subject in need of treatment any of the pharmaceutical compositions disclosed herein. In some embodiments, this composition includes a targeted therapeutic that is the fusion protein of SEQ ID NO. 21 or 22.

Definitions

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" is meant the prevention, reduction or palliation of a state, or improvement of the state of a subject. Amelioration includes, but does not require complete recovery or complete prevention of a disease condition. In some embodiments, amelioration includes increasing levels of relevant protein or its activity that is deficient in relevant disease tissues.

Amino acid: As used herein, term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active. In particular embodiments, where a protein or polypeptide is biologically active, a portion of that protein or polypeptide that shares at least one biological activity of the protein or polypeptide is typically referred to as a "biologically active" portion.

Cation-independent mannose-6-phosphate receptor (CI-M6PR): As used herein, the term "cation-independent mannose-6-phosphate receptor (CI-M6PR)" refers to a cellular receptor that binds mannose-6-phosphate (M6P) tags on acid hydrolase precursors in the Golgi apparatus that are destined for transport to the lysosome. In addition to mannose-6-phosphates, the CI-M6PR also binds other proteins including IGF-II. The CI-M6PR is also known as "M6P/IGF-II receptor", "CI-M6PR/IGF-II receptor", "CD222", "MPR300", "IGF-II receptor" or "IGF2 Receptor." These terms and abbreviations thereof are used interchangeably herein.

Cell culture: These terms as used herein refer to a cell population that is gown in a medium under conditions suitable to survival and/or growth of the cell population. As will be clear to those of ordinary skill in the art, these terms as used herein may refer to the combination comprising the cell population and the medium in which the population is grown.

Diluent: As used herein, the term "diluent" refers to a pharmaceutically acceptable (e.g., safe and non-toxic for administration to a human) diluting substance useful for the preparation of a reconstituted formulation. Exemplary diluents include sterile water, bacteriostatic water for injection (BWFI), a pH buffered solution (e.g. phosphate-buffered saline), sterile saline solution, Ringer's solution or dextrose solution.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses.

Enzyme replacement therapy (ERT): As used herein, the term "enzyme replacement therapy (ERT)" refers to any therapeutic strategy that corrects an enzyme deficiency by providing the missing enzyme. In some embodiments, the missing enzyme is provided by intrathecal administration. In some embodiments, the missing enzyme is provided by infusing into bloodsteam. Once administered, enzyme is taken up by cells and transported to the lysosome, where the enzyme acts to eliminate material that has accumulated in the lysosomes due to the enzyme deficiency. Typically, for lysosomal enzyme replacement therapy to be effective, the therapeutic enzyme is delivered to lysosomes in the appropriate cells in target tissues where the storage defect is manifest.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein. In this application, the terms "expression" and "production," and grammatical equivalent, are used interchangeably.

Fragment: The term "fragment" as used herein refers to polypeptides and is defined as any discrete portion of a given polypeptide that is unique to or characteristic of that polypeptide. The term as used herein also refers to any discrete portion of a given polypeptide that retains at least a fraction of the activity of the full-length polypeptide. Preferably the fraction of activity retained is at least 10% of the activity of the full-length polypeptide. More preferably the fraction of activity retained is at least 20%, 30%, 40%, 50%, 60%, 70%, 80% or 90% of the activity of the full-length polypeptide. More preferably still the fraction of activity retained is at least 95%, 96%, 97%, 98% or 99% of the activity of the full-length polypeptide. Most preferably, the fraction of activity retained is 100% of the activity of the full-length polypeptide. The term as used herein also refers to any portion of a given polypeptide that includes at least an established sequence element found in the full-length polypeptide. Preferably, the sequence element spans at least 4-5, more preferably at least about 10, 15, 20, 25, 30, 35, 40, 45, 50 or more amino acids of the full-length polypeptide.

Gene: The term "gene" as used herein refers to any nucleotide sequence, DNA or RNA, at least some portion of which encodes a discrete final product, typically, but not limited to, a polypeptide, which functions in some aspect of a cellular process. The term is not meant to refer only to the coding sequence that encodes the polypeptide or other discrete final product, but may also encompass regions preceding and following the coding sequence that modulate the basal level of expression, as well as intervening sequences ("introns") between individual coding segments ("exons"). In some embodiments, a gene may include regulatory sequences (e.g., promoters, enhancers, poly adenylation sequences, termination sequences, Kozac sequences, tata box, etc.) and/or modification sequences. In some embodiments, a gene may include references to nucleic acids that do not encode proteins but rather encode functional RNA molecules such as tRNAs, RNAi-inducing agents, etc.

Gene product or expression product: As used herein, the term "gene product" or "expression product" generally refers to an RNA transcribed from the gene (pre- and/or post-processing) or a polypeptide (pre- and/or post-modification) encoded by an RNA transcribed from the gene.

Genetic control element: The term "genetic control element" as used herein refers to any sequence element that modulates the expression of a gene to which it is operably linked. Genetic control elements may function by either increasing or decreasing the expression levels and may be located before, within or after the coding sequence. Genetic control elements may act at any stage of gene expression by regulating, for example, initiation, elongation or termination of transcription, mRNA splicing, mRNA editing, mRNA stability, mRNA localization within the cell, initiation, elongation or termination of translation, or any other stage of gene expression. Genetic control elements may function individually or in combination with one another.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Intrathecal administration: As used herein, the term "intrathecal administration" or "intrathecal injection" refers to an injection into the spinal canal (intrathecal space surrounding the spinal cord). Various techniques may be used including, without limitation, lateral cerebroventricular injection through a burrhole or cisternal or lumbar puncture or the like. In some embodiments, "intrathecal administration" or "intrathecal delivery" according to the present invention refers to IT administration or delivery via the lumbar area or region, i.e., lumbar IT administration or delivery. As used herein, the term "lumbar region" or "lumbar area" refers to the area between the third and fourth lumbar (lower back) vertebrae and, more inclusively, the L2-S1 region of the spine.

Linker: As used herein, the term "linker" refers to, in a fusion protein, an amino acid sequence other than that appearing at a particular position in the natural protein and is generally designed to be flexible or to interpose a structure, such as an a-helix, between two protein moieties. A linker is also referred to as a spacer.

Lysosomal enzyme: As used herein, the term "lysosomal enzyme" refers to any enzyme that is capable of reducing accumulated materials in mammalian lysosomes or that can rescue or ameliorate one or more lysosomal storage disease symptoms. Lysosomal enzymes suitable for the invention include both wild-type or modified lysosomal enzymes and can be produced using recombinant and synthetic methods or purified from nature sources. Exemplary lysosomal enzymes are listed in Table 2.

Lysosomal enzyme deficiency: As used herein, "lysosomal enzyme deficiency" refers to a group of genetic disorders that result from deficiency in at least one of the enzymes that are required to break macromolecules (e.g., enzyme substrates) down to peptides, amino acids, monosaccharides, nucleic acids and fatty acids in lysosomes. As a result, individuals suffering from lysosomal enzyme deficiencies have accumulated materials in various tissues (e.g., CNS, liver, spleen, gut, blood vessel walls and other organs).

Lysosomal Storage Disease: As used herein, the term "lysosomal storage disease" refers to any disease resulting from the deficiency of one or more lysosomal enzymes necessary for metabolizing natural macromolecules. These diseases typically result in the accumulation of un-degraded molecules in the lysosomes, resulting in increased numbers of storage granules (also termed storage vesicles). These diseases and various examples are described in more detail below.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Peptide: As used herein, a "peptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that peptides sometimes include "non-natural" amino acids or other entities that nonetheless are capable of integrating into a polypeptide chain, optionally. As used herein, the terms "polypeptide" and "peptide" are used interchangeably.

Protein: As used herein, the term "protein" of "therapeutic protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain 1-amino acids, d-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

Recombinant protein and Recombinant polypeptide: These terms as used herein refer to a polypeptide expressed from a host cell, that has been genetically engineered to express that polypeptide. In some embodiments, a recombinant protein may be expressed in a host cell derived from an animal. In some embodiments, a recombinant protein may be expressed in a host cell derived from an insect. In some embodiments, a recombinant protein may be expressed in a host cell derived from a yeast. In some embodiments, a recombinant protein may be expressed in a host cell derived from a prokaryote. In some embodiments, a recombinant protein may be expressed in a host cell derived from a mammal. In some embodiments, a recombinant protein may be expressed in a host cell derived from a human. In some embodiments, the recombinantly expressed polypeptide may be identical or similar to a polypeptide that is normally expressed in the host cell. In some embodiments, the recombinantly expressed polypeptide may be foreign to the host cell, i.e. heterologous to peptides normally expressed in the host cell. Alternatively, in some embodiments the recombinantly expressed polypeptide can be a chimeric, in that portions of the polypeptide contain amino acid sequences that are identical or similar to polypeptides normally expressed in the host cell, while other portions are foreign to the host cell.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Target tissues: As used herein, the term "target tissues" refers to any tissue that is affected by the lysosomal storage disease to be treated or any tissue in which the deficient lysosomal enzyme is normally expressed. In some embodiments, target tissues include those tissues in which there is a detectable or abnormally high amount of enzyme substrate, for example stored in the cellular lysosomes of the tissue, in patients suffering from or susceptible to the lysosomal storage disease. In some embodiments, target tissues include those tissues that display disease-associated pathology, symptom, or feature. In some embodiments, target tissues include those tissues in which the deficient lysosomal enzyme is normally expressed at an elevated level. As used herein, a target tissue may be a brain target tissue, a spinal cord target tissue and/or a peripheral target tissue. Exemplary target tissues are described in detail below.

Treatment: As used herein, the term "treatment" (also "treat" or "treating") refers to any administration of a therapeutic protein (e.g., lysosomal enzyme) that partially or completely alleviates, ameliorates, relieves, inhibits, delays onset of, reduces severity of and/or reduces incidence of one or more symptoms or features of a particular disease, disorder, and/or condition (e.g., Hunters syndrome, Sanfilippo B syndrome). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

DETAILED DESCRIPTION

The present invention provides, among other things, methods and compositions for lysosomal targeting of a therapeutic protein (e.g., a lysosomal enzyme) based on a lysosomal targeting moiety that comprises PCSK9 (proprotein convertase subtilisin kexin type 9). In some embodiments, the present invention provides a targeted therapeutic comprising a lysosomal enzyme and a lysosomal targeting moiety that binds to amyloid precursor-like protein 2 (APLP2), Dynamin, amyloid precursor protein (APP), autosomal recessive hypercholesterolemia (ARH) protein, low density lipoprotein receptor-related protein 8 (Lrp8) and/or Annexin A2.

Various aspects of the invention are described in further detail in the following subsections. The use of subsections is not meant to limit the invention. Each subsection may apply to any aspect of the invention. In this application, the use of "or" means "and/or" unless stated otherwise.

Lysosomal Enzymes

The present invention may be used to target any therapeutic protein to a lysosome. In particular, the present invention may be used to target a lysosomal enzyme to a lysosome for the treatment of a lysosomal storage disease. According to the present invention, a lysosomal enzyme is contemplated to encompass any enzyme or protein that, when targeted to the lysosome, is suitable for the treatment of a lysosomal storage disease. As non-limiting examples, particularly suitable lysosomal enzymes are acid alpha-glucosidase (GAA) protein, which is deficient in Pompe disease, and alpha-N-acetylglucosaminidase (Naglu) protein, which is deficient in Sanfilippo Syndrome Type B disease. Additional exemplary lysosomal enzymes are shown in Table 3.

GAA Protein

A suitable GAA protein according to the present invention can be any molecule that can substitute for naturally-occurring GAA protein activity or rescue one or more phenotypes or symptoms associated with GAA-deficiency. In some embodiments, a GAA protein suitable for the invention is a polypeptide having an N-terminus and C-terminus and an amino acid sequence substantially similar or identical to mature human GAA protein.

Typically, human GAA is produced as a precursor molecule that is processed to a mature form. This process generally occurs by removing the 27 amino acid signal peptide as the protein enters the endoplasmic reticulum. Typically, the precursor form including the 27 amino acid signal peptide is also referred to as Full-Length GAA protein, which contains 952 amino acids. The N-terminal 27 amino acids are cleaved as the Full-Length GAA protein enters the endoplasmic reticulum, resulting in the Precursor Form GAA Protein. The Precursor Form GAA Protein is then subsequently cleaved to remove a N-terminal propeptide sequence of 42 amino acids, to produce the Mature Form GAA protein (aa 70-952). Thus, it is contemplated that the N-terminal 27 amino acids that constitute the signal peptide and the N-terminal 42 amino acids that constitute the propeptide are generally not required for GAA protein activity. However, the use of the Full-Length GAA Protein (aa 1-952) and of the Precursor Form GAA Protein (aa 28-952) are also contemplated within the scope of the instant invention. The amino acid sequences of the Mature Form GAA Protein (SEQ ID NO:1); Precursor Form GAA Protein (SEQ ID NO:2) and Full-Length GAA Protein (SEQ ID NO:3) of a typical wild-type or naturally-occurring human GAA protein are shown in Table 1 below.

TABLE 1

Mature and Precursor GAA Protein

| | |
|---|---|
| Mature Form Protein | GAAAHPGRPRAVPTQCDVPPNSRFDCAPDKAITQEQCEARGCCYIPAKQGLQGAQMG QPWCFFPPSYPSYKLENLSSSEMGYTATLTRTTPTFFPKDILTLRLDVMMETEN RLHFTIKDPANRRYEVPLETPHVHSRAPSPLYSVEFSEEPFGVIVRRQLDGRVL LNTTVAPLFFADQFLQLSTSLPSQYITGLAEHLSPLMLSTSWTRITLWNRDLAP TPGANLYGSHPFYLALEDGGSAHGVFLLNSNAMDVVLQPSPALSWRSTGGILDV YIFLGPEPKSVVQQYLDVVGYPFMPPYWGLGFHLCRWGYSSTAITRQVVENMTR AHFPLDVQWNDLDYMDSRRDFTFNKDGFRDFPAMVQELHQGGRRYMMIVDPAIS SSGPAGSYRPYDEGLRRGVFITNETGQPLIGKVWPGSTAFPDFTNPTALAWWED MVAEFHDQVPFDGMWIDMNEPSNFIRGSEDGCPNNELENPPYVPGVVGGTLQAA TICASSHQFLSTHYNLHNLYGLTEAIASHRALVKARGTRPFVISRSTFAGHGRY AGHWTGDVWSSWEQLASSVPEILQFNLLGVPLVGADVCGFLGNTSEELCVRWTQ LGAFYPFMRNHNSLLSLPQEPYSFSEPAQQAMRKALTLRYALLPHLYTLFHQAH VAGETVARPLFLEFPKDSSTWTVDHQLLWGEALLITPVLQAGKAEVTGYFPLGT WYDLQTVPVEALGSLPPPPAAPREPAIHSEGQWVTLPAPLDTINVHLRAGYIIP LQGPGLTTTESRQQPMALAVALTKGGEARGELFWDDGESLEVLERGAYTQVIFL ARNNTIVNELVRVTSEGAGLQLQKVTVLGVATAPQQVLSNGVPVSNFTYSPDTK VLDICVSLLMGEQFLVSWC (SEQ ID NO: 1) |
| Precursor Form GAA Protein | GHILLHDFLLVPRELSGSSPVLEETHPAHQQGASRPGPRDAQAHPGRPRAVPTQ CDVPPNSRFDCAPDKAITQEQCEARGCCYIPAKQGLQGAQMGQPWCFFPPSYPS YKLENLSSSEMGYTATLTRTTPTFFPKDILTLRLDVMMETENRLHFTIKDPANR RYEVPLETPHVHSRAPSPLYSVEFSEEPFGVIVRRQLDGRVLLNTTVAPLFFAD QFLQLSTSLPSQYITGLAEHLSPLMLSTSWTRITLWNRDLAPTPGANLYGSHPF YLALEDGGSAHGVFLLNSNAMDVVLQPSPALSWRSTGGILDVYIFLGPEPKSVV QQYLDVVGYPFMPPYWGLGFHLCRWGYSSTAITRQVVENMTRAHFPLDVQWNDL DYMDSRRDFTFNKDGFRDFPAMVQELHQGGRRYMMIVDPAISSSGPAGSYRPYD EGLRRGVFITNETGQPLIGKVWPGSTAFPDFTNPTALAWWEDMVAEFHDQVPFD GMWIDMNEPSNFIRGSEDGCPNNELENPPYVPGVVGGTLQAATICASSHQFLST HYNLHNLYGLTEAIASHRALVKARGTRPFVISRSTFAGHGRYAGHWTGDVWSSW EQLASSVPEILQFNLLGVPLVGADVCGFLGNTSEELCVRWTQLGAFYPFMRNHN SLLSLPQEPYSFSEPAQQAMRKALTLRYALLPHLYTLFHQAHVAGETVARPLFL EFPKDSSTWTVDHQLLWGEALLITPVLQAGKAEVTGYFPLGTWYDLQTVPVEAL GSLPPPPAAPREPAIHSEGQWVTLPAPLDTINVHLRAGYIIPLQGPGLTTTESR QQPMALAVALTKGGEARGELFWDDGESLEVLERGAYTQVIFLARNNTIVNELVR VTSEGAGLQLQKVTVLGVATAPQQVLSNGVPVSNFTYSPDTKVLDICVSLLMGE QFLVSWC (SEQ ID NO: 2) |

TABLE 1-continued

Mature and Precursor GAA Protein

| | |
|---|---|
| Full-Length<br>Protein | GAAMGVRHPPCSHRLLAVCALVSLATAALLGHILLHDFLLVPRELSGSSPVLEETHP<br>AHQQGASRPGPRDAQAHPGRPRAVPTQCDVPPNSRFDCAPDKAITQEQCEARGC<br>CYIPAKQGLQGAQMGQPWCFFPPSYPSYKLENLSSSEMGYTATLTRTTPTFFPK<br>DILTLRLDVMMETENRLHFTIKDPANRRYEVPLETPHVHSRAPSPLYSVEFSEE<br>PFGVIVRRQLDGRVLLNTTVAPLFFADQFLQLSTSLPSQYITGLAEHLSPLMLS<br>TSWTRITLWNRDLAPTPGANLYGSHPFYLALEDGGSAHGVFLLNSNAMDVVLQP<br>SPALSWRSTGGILDVYIFLGPEPKSVVQQYLDVVGYPFMPPYWGLGFHLCRWGY<br>SSTAITRQVVENMTRAHFPLDVQWNDLDYMDSRRDFTFNKDGFRDFPAMVQELH<br>QGGRRYMMIVDPAISSSGPAGSYRPYDEGLRRGVFITNETGQPLIGKVWPGSTA<br>FPDFTNPTALAWWEDMVAEFHDQVPFDGMWIDMNEPSNFIRGSEDGCPNNELEN<br>PPYVPGVVGGTLQAATICASSHQFLSTHYNLHNLYGLTEALASHRALVKARGTR<br>PFVISRSTFAGHGRYAGHWTGDVWSSWEQLASSVPEILQFNLLGVPLVGADVCG<br>FLGNTSEELCVRWTQLGAFYPFMRNHNSLLSLPQEPYSFSEPAQQAMRKALTLR<br>YALLPHLYTLFHQAHVAGETVARPLFLEFPKDSSTWTVDHQLLWGEALLITPVL<br>QAGKAEVTGYFPLGTWYDLQTVPVEALGSLPPPPAAPREPAIHSEGQWVTLPAP<br>LDTINVHLRAGYIIPLQGPGLTTTESRQQPMALAVALTKGGEARGELFWDDGES<br>LEVLERGAYTQVIFLARNNTIVNELVRVTSEGAGLQLQKVTVLGVATAPQQVLS<br>NGVPVSNFTYSPDTKVLDICVSLLMGEQFLVSWC (SEQ ID NO: 3) |

Thus, in some embodiments, GAA protein suitable for the present invention is a human Mature Form GAA Protein (SEQ ID NO:1). In some embodiments, a suitable GAA protein may be a homologue or an orthologue of human Mature Form GAA Protein from a different species (e.g., mouse, rat, sheep, pig, dog, etc.). In other embodiments, a suitable GAA protein may be a functional variant of human Mature Form GAA Protein. A functional variant Mature Form GAA Protein may be a modified human Mature Form GAA Protein containing one or more amino acid substitutions, deletions, and/or insertions as compared to a wild-type or naturally-occurring human Mature Form GAA Protein (e.g., SEQ ID NO:1), while retaining substantial GAA protein activity. Thus, in some embodiments, a GAA protein suitable for the present invention is substantially homologous to human Mature Form GAA Protein (SEQ ID NO:1). In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:1. In some embodiments, a GAA protein suitable for the present invention is substantially identical to human Mature Form GAA Protein (SEQ ID NO:1). In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:1. In some embodiments, a GAA protein suitable for the present invention contains a fragment or a portion of human Mature Form GAA Protein.

Alternatively, a GAA protein suitable for the present invention is a human Precursor Form GAA Protein (SEQ ID NO:2). In some embodiments, a GAA protein suitable may be a homologue or an orthologue of human Precursor Form GAA Protein from a different species (e.g., mouse, rat, sheep, pig, dog, etc.). In some embodiments, a suitable GAA protein is a functional variant of a human Precursor Form GAA Protein, containing one or more amino acid substitutions, deletions, and/or insertions as compared to a wild-type or naturally-occurring human Precursor Form GAA Protein (e.g., SEQ ID NO:2), while retaining substantial GAA protein activity. Thus, in some embodiments, a GAA protein suitable for the present invention is substantially homologous to human Precursor Form GAA Protein (SEQ ID NO:2). In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:2. In some embodiments, a GAA protein suitable for the present invention is substantially identical to SEQ ID NO:2. In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:2. In some embodiments, a GAA protein suitable for the present invention contains a fragment or a portion of human Precursor Form GAA Protein. As used herein, a Precursor Form GAA Protein typically contains a propeptide sequence.

Alternatively, a GAA protein suitable for the present invention is a human Full-Length GAA Protein (SEQ ID NO:3). In some embodiments, a GAA protein suitable may be a homologue or an orthologue of Full-Length GAA Protein from a different species (e.g., mouse, rat, sheep, pig, dog, etc.). In some embodiments, a suitable GAA protein is a functional variant of human Full-Length GAA Protein, containing one or more amino acid substitutions, deletions, and/or insertions as compared to a wild-type or naturally-occurring full length GAA protein (e.g., SEQ ID NO:3), while retaining substantial GAA protein activity. Thus, in some embodiments, a GAA protein suitable for the present invention is substantially homologous to human Full-Length GAA Protein (SEQ ID NO:3). In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:3. In some embodiments, a GAA protein suitable for the present invention is substantially identical to SEQ ID NO:3. In some embodiments, a GAA protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:3. In some embodiments, a GAA protein suitable for the present invention contains a fragment or a portion of human Full-Length GAA Protein. As used herein, a Full-Length GAA Protein typically contains a signal peptide sequence and a propeptide sequence.

Naglu Protein

A suitable Naglu protein according to the present invention can be any molecule that can substitute for naturally-occurring Naglu protein activity or rescue one or more phenotypes or symptoms associated with Naglu-deficiency. In some embodiments, a Naglu protein suitable for the invention is a polypeptide having an N-terminus and C-terminus and an amino acid sequence substantially similar or identical to mature human Naglu protein.

Typically, human Naglu is produced as a precursor molecule that is processed to a mature form. This process generally occurs by removing the 23 amino acid signal peptide as the protein enters the endoplasmic reticulum. Typically, the precursor form is also referred to as full-length precursor or full-length Naglu protein, which contains 743 amino acids. The N-terminal 23 amino acids are cleaved as the precursor protein enters the endoplasmic reticulum, resulting in a mature form. Thus, it is contemplated that the N-terminal 23 amino acids is generally not required for the Naglu protein activity. However, the use of the full-length precursor of the Naglu protein is also contemplated within the scope of the instant invention. The amino acid sequences of the mature form (SEQ ID NO:4) and full-length precursor (SEQ ID NO:5) of a typical wild-type or naturally-occurring human Naglu protein are shown in Table 2 below.

Naglu protein (SEQ ID NO:4). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:4. In some embodiments, a Naglu protein suitable for the present invention is substantially identical to mature human Naglu protein (SEQ ID NO:4). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:4. In some embodiments, a Naglu protein suitable for the present invention contains a fragment or a portion of a mature Naglu protein.

Alternatively, a Naglu protein suitable for the present invention is a full-length Naglu protein (SEQ ID NO:5). In some embodiments, a Naglu protein suitable may be a homologue or an orthologue of the full-length human Naglu protein from a different species (e.g., mouse, rat, sheep, pig, dog, etc.). In some embodiments, a suitable Naglu protein is a functional variant of the full-length human Naglu protein,

TABLE 2

Mature and Precursor Naglu Protein

| | |
|---|---|
| Mature Form of Naglu | DEAREAAAVRALVARLLGPGPAADFSVSVERALAAKPGLDTYSLGGGGAARVRV RGSTGVAAAAGLHRYLRDFCGCHVAWSGSQLRLPRPLPAVPGELTEATPNRYRY YQNVCTQSYSFVWWDWARWEREIDWMALNGINLALAWSGQEAIWQRVYLALGLT QAEINEFFTGPAFLAWGRMGNLHTWDGPLPPSWHIKQLYLQHRVLDQMRSFGMT PVLPAFAGHVPEAVTRVFPQVNVTKMGSWGHFNCSYSCSFLLAPEDPIFPIIGS LFLRELIKEFGTDHIYGADTFNEMQPPSSEPSYLAAATTAVYEAMTAVDTEAVW LLQGWLFQHQPQFWGPAQIRAVLGAVPRGRLLVLDLFAESQPVYTRTASFQGQP FIWCMLHNFGGNHGLFGALEAVNGGPEAARLFPNSTMVGTGMAPEGISQNEVVY SLMAELGWRKDPVPDLAAWVTSFAARRYGVSHPDAGAAWRLLLRSVYNCSGEAC RGHNRSPLVRRPSLQMNTSIWYNRSDVFEAWRLLLTSAPSLATSPAFRYDLLDL TRQAVQELVSLYYEEARSAYLSKELASLLRAGGVLAYELLPALDEVLASDSRFL LGSWLEQARAAAVSEAEADFYEQNSRYQLTLWGPEGNILDYANKQLAGLVANYY TPRWRLFLEALVDSVAQGIPFQQHQFDKNVFQLEQAFVLSKQRYPSQPRGDTVD LAKKIFLKYYPRWVAGSW (SEQ ID NO: 4) |
| Full-Length Precursor/Full Length Naglu Protein | MEAVAVAAAVGVLLLAGAGGAAGDEAREAAAVRALVARLLGPGPAADFSVSVER ALAAKPGLDTYSLGGGGAARVRVRGSTGVAAAAGLHRYLRDFCGCHVAWSGSQL RLPRPLPAVPGELTEATPNRYRYYQNVCTQSYSFVWWDWARWEREIDWMALNGI NLALAWSGQEAIWQRVYLALGLTQAEINEFFTGPAFLAWGRMGNLHTWDGPLPP SWHIKQLYLQHRVLDQMRSFGMTPVLPAFAGHVPEAVTRVFPQVNVTKMGSWGH FNCSYSCSFLLAPEDPIFPIIGSLFLRELIKEFGTDHIYGADTFNEMQPPSSEP SYLAAATTAVYEAMTAVDTEAVWLLQGWLFQHQPQFWGPAQIRAVLGAVPRGRL LVLDLFAESQPVYTRTASFQGQPFIWCMLHNFGGNHGLFGALEAVNGGPEAARL FPNSTMVGTGMAPEGISQNEVVYSLMAELGWRKDPVPDLAAWVTSFAARRYGVS HPDAGAAWRLLLRSVYNCSGEACRGHNRSPLVRRPSLQMNTSIWYNRSDVFEAW RLLLTSAPSLATSPAFRYDLLDLTRQAVQELVSLYYEEARSAYLSKELASLLRA GGVLAYELLPALDEVLASDSRFLLGSWLEQARAAAVSEAEADFYEQNSRYQLTL WGPEGNILDYANKQLAGLVANYYTPRWRLFLEALVDSVAQGIPFQQHQFDKNVF QLEQAFVLSKQRYPSQPRGDTVDLAKKIFLKYYPRWVAGSW (SEQ ID NO: 5) |

Thus, in some embodiments, Naglu protein suitable for the present invention is a mature human Naglu protein (SEQ ID NO:4). In some embodiments, a suitable Naglu protein may be a homologue or an orthologue of the mature human Naglu protein from a different species (e.g., mouse, rat, sheep, pig, dog, etc.). In other embodiments, a suitable Naglu protein may be a functional variant of the mature human Naglu protein. A functional variant of the mature human Naglu protein may be a modified mature human Naglu protein containing one or more amino acid substitutions, deletions, and/or insertions as compared to a wild-type or naturally-occurring Naglu protein (e.g., SEQ ID NO:4), while retaining substantial Naglu protein activity. Thus, in some embodiments, a Naglu protein suitable for the present invention is substantially homologous to mature human containing one or more amino acid substitutions, deletions, and/or insertions as compared to a wild-type or naturally-occurring full-length Naglu protein (e.g., SEQ ID NO:5), while retaining substantial Naglu protein activity. Thus, in some embodiments, a Naglu protein suitable for the present invention is substantially homologous to full-length human Naglu protein (SEQ ID NO:5). In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more homologous to SEQ ID NO:5. In some embodiments, a Naglu protein suitable for the present invention is substantially identical to SEQ ID NO:5. In some embodiments, a Naglu protein suitable for the present invention has an amino acid sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:5. In some embodiments, a Naglu protein suitable for the present invention contains a fragment or a portion of a full-length Naglu protein. As used herein, a full-length Naglu protein typically contains a signal peptide sequence.

Additional Lysosomal Enzymes

The present invention may be used to deliver any lysosomal enzymes that can be used to treat any lysosomal storage diseases, in particular those lysosomal storage diseases having skeletal muscle, kidney and/or CNS etiology and/or symptoms, including, but are not limited to, aspartylglucosaminuria, cholesterol ester storage disease, Wolman disease, cystinosis, Danon disease, Fabry disease, Farber lipogranulomatosis, Farber disease, fucosidosis, galactosialidosis types I/II, Gaucher disease types I/II/III, globoid cell leukodystrophy, Krabbe disease, glycogen storage disease II, Pompe disease, GM1-gangliosidosis types I/II/III, GM2-gangliosidosis type I, Tay Sachs disease, GM2-gangliosidosis type II, Sandhoff disease, GM2-gangliosidosis, α-mannosidosis types I/II, .beta.-mannosidosis, metachromatic leukodystrophy, mucolipidosis type I, sialidosis types I/II, mucolipidosis types II/III, I-cell disease, mucolipidosis type IIIC pseudo-Hurler polydystrophy, mucopolysaccharidosis type I, mucopolysaccharidosis type II, mucopolysaccharidosis type MA, Sanfilippo syndrome, mucopolysaccharidosis type IIIB, mucopolysaccharidosis type IIIC, mucopolysaccharidosis type HID, mucopolysaccharidosis type IVA, Morquio syndrome, mucopolysaccharidosis type IVB, mucopolysaccharidosis type VI, mucopolysaccharidosis type VII, Sly syndrome, mucopolysaccharidosis type IX, multiple sulfatase deficiency, neuronal ceroid lipofuscinosis, CLN1 Batten disease, CLN2 Batten diseae, Niemann-Pick disease types A/B, Niemann-Pick disease type C1, Niemann-Pick disease type C2, pycnodysostosis, Schindler disease types I/II, Gaucher disease and sialic acid storage disease.

A detailed review of the genetic etiology, clinical manifestations, and molecular biology of the lysosomal storage diseases are detailed in Scriver et al., eds., The Metabolic and Molecular Basis of Inherited Disease, 7.sup.th Ed., Vol. II, McGraw Hill, (1995). Thus, the enzymes deficient in the above diseases are known to those of skill in the art, some of these are exemplified in Table 3 below:

TABLE 3

Enzymes Associated With Lysosomal Storage Disease

| Disease Name | Enzyme Deficiency | Substance Stored |
| --- | --- | --- |
| Pompe Disease | Acid-α1, 4-Glucosidase | Glycogen α-1-4 linked Oligosaccharides |
| GM1 Gangliodsidosis | β-Galactosidase | $GM_1$ Gangliosides |
| Tay-Sachs Disease | β-Hexosaminidase A | $GM_2$ Ganglioside |
| GM2 Gangliosidosis: AB Variant | $GM_2$ Activator Protein | $GM_2$ Ganglioside |
| Sandhoff Disease | β-Hexosaminidase A&B | $GM_2$ Ganglioside |
| Fabry Disease | α-Galactosidase A | Globosides |
| Gaucher Disease | Glucocerebrosidase | Glucosylceramide |
| Metachromatic Leukodystrophy | Arylsulfatase A | Sulphatides |
| Krabbe Disease | Galactosylceramidase | Galactocerebroside |
| Niemann Pick, Types A & B | Acid Sphingomyelinase | Sphingomyelin |
| Niemann-Pick, Type C | Cholesterol Esterification Defect | Sphingomyelin |
| Niemann-Pick, Type D | Unknown | Sphingomyelin |
| Farber Disease | Acid Ceramidase | Ceramide |
| Wolman Disease | Acid Lipase | Cholesteryl Esters |
| Hurler Syndrome (MPS IH) | α-L-Iduronidase | Heparan & Dermatan Sulfates |
| Scheie Syndrome (MPS IS) | α-L-Iduronidase | Heparan & Dermatan, Sulfates |
| Hurler-Scheie (MPS IH/S) | α-L-Iduronidase | Heparan & Dermatan Sulfates |
| Hunter Syndrome (MPS II) | Iduronate Sulfatase | Heparan & Dermatan Sulfates |
| Sanfilippo A (MPS IIIA) | Heparan N-Sulfatase | Heparan Sulfate |
| Sanfilippo B (MPS IIIB) | α-N-Acetylglucosaminidase | Heparan Sulfate |
| Sanfilippo C (MPS IIIC) | Acetyl-CoA-Glucosaminide Acetyltransferase | Heparan Sulfate |
| Sanfilippo D (MPS IIID) | N-Acetylglucosamine-6-Sulfatase | Heparan Sulfate |
| Morquio B (MPS IVB) | β-Galactosidase | Keratan Sulfate |
| Maroteaux-Lamy (MPS VI) | Arylsulfatase B | Dermatan Sulfate |
| Sly Syndrome (MPS VII) | β-Glucuronidase | |
| α -Mannosidosis | α-Mannosidase | Mannose/Oligosaccharides |
| β -Mannosidosis | β-Mannosidase | Mannose/Oligosaccharides |
| Fucosidosis | α-L-Fucosidase | Fucosyl/Oligosaccharides |
| Aspartylglucosaminuria | N-Aspartyl-β-Glucosaminidase | Aspartylglucosamine Asparagines |

TABLE 3-continued

Enzymes Associated With Lysosomal Storage Disease

| Disease Name | Enzyme Deficiency | Substance Stored |
|---|---|---|
| Sialidosis (Mucolipidosis I) | α-Neuraminidase | Sialyloligosaccharides |
| Galactosialidosis (Goldberg Syndrome) | Lysosomal Protective Protein Deficiency | Sialyloligosaccharides |
| Schindler Disease | α-N-Acetyl-Galactosaminidase | |
| Mucolipidosis II (I-Cell Disease) | N-Acetylglucosamine-1-Phosphotransferase | Heparan Sulfate |
| Mucolipidosis III (Pseudo-Hurler Polydystrophy) | Same as ML II | |
| Cystinosis | Cystine Transport Protein | Free Cystine |
| Salla Disease | Sialic Acid Transport Protein | Free Sialic Acid and Glucuronic Acid |
| Infantile Sialic Acid Storage Disease | Sialic Acid Transport Protein | Free Sialic Acid and Glucuronic Acid |
| Infantile Neuronal Ceroid Lipofuscinosis | Palmitoyl-Protein Thioesterase | Lipofuscins |
| Mucolipidosis IV | Unknown | Gangliosides & Hyaluronic Acid |
| Prosaposin | Saposins A, B, C or D | |

In some embodiments, a suitable lysosomal enzyme may be a naturally occurring lysosomal enzyme. In some embodiments, a suitable lysosomal enzyme may be a recombinant version of a naturally occurring lysosomal enzyme.

In some embodiments, a lysosomal enzyme suitable for the invention may have a wild-type or naturally occurring sequence. In some embodiments, a lysosomal enzyme suitable for the invention may have a modified sequence having substantial homology or identify to the wild-type or naturally-occurring sequence (e.g., having at least 50%, 55%, 60%, 65%, 70%, 75%, 80%, 85%, 90%, 95%, 98% sequence identity to the wild-type or naturally-occurring sequence).

Lysosomal Targeting Moiety

According to the present invention, a lysosomal targeting moiety refers to any agent that can facilitate lysosomal delivery via binding to a protein other than the CI-M6PR receptor. In some embodiments, the lysosomal targeting moiety is able to bind, directly or indirectly, to one or more membrane proteins via a cis-his rich domain (CHRD) to form a protein complex. In some embodiments, the lysosomal targeting moiety binds, directly or indirectly, to one or more secondary binding proteins selected from the group consisting of the low density lipoprotein receptor (LDLR), amyloid precursor-like protein 2 (APLP2), Dynamin, amyloid precursor protein (APP), autosomal recessive hypercholesterolemia (ARH) protein, low density lipoprotein receptor-related protein 8 (Lrp8), or combinations thereof. In some embodiments, the lysosomal targeting moiety comprises a proprotein convertase, or fragment thereof. In some embodiments, the proprotein convertase is a mammalian proprotein convertase.

Proprotein Convertase

Mammalian proprotein convertases are members of a secretory serine protease family composed of nine members related to bacterial subtilisin and yeast kexin. The catalytic domains of seven members of this family (PC1/3; PC2; Furin; PC4; PC5/6; PACE4 and PC7) exhibit homology to the catalytic domain of yeast kexin, and they are known to cleave after basic residues in target proteins. The eighth member, SKI-1/S1P, shows strong homology to bacterial pyrolysin and, similar to the other 7 family members, is known to cleave after basic residues in target proteins. Finally, the last member, PCSK9, shows homology to fungal proteinase K and undergoes autoproteolytic cleavage at the (V/I)FAQ motif in the endoplasmic reticulum. Like many other proteases, these proprotein convertases are synthesized as inactive zymogens that carry an N-terminal propeptide. It is thought that this propeptide facilitates proper folding of the convertase, and that it functions as a natural inhibitor of the enzyme until it is cleaved off.

Among the nine family members, five PCs (Furin, PC5/6; PACE4, SKI-1/S1P and PCSK9) have been shown to play a central role in regulating sterols and/or lipid metabolism. This is especially true for PCSK9, whose over-activity/gain-of-function results in Familial Hypercholesterolemia (FH). PCSK9 is highly expressed in the liver and produced as a preprotein that undergoes autoproteolytic cleavage during passage through the secretory pathyway. During this process, the C-terminus of the N-terminal propeptide occupies PCSK9's catalytic pocket, inhibiting its proteolytic activity and blocking access to other exogenous substrates.

PCSK9 binds to the EGF-A domain of the LDL receptor through part of its catalytic domain to form a non-covalent protein complex, which is internalized by endocytosis and targeted for degradation in the acidic compartment of the lysosome.

Data suggest, that while the PCSK9-LDLR complex is necessary for LDL receptor (LDLR) recycling and removal of LDL from the extracellular space, it is not required for PCSK9 endocytosis to the lysosome. Several studies have shown that disruption of PCSK9 binding to LDLR, through mutations within its catalytic domain or via the use of blocking antibodies does not impede PCSK9 internalization. This suggests that alternative mechanisms exist by which PCSK9 is internalized. In particular, it has been suggested that lysosomal targeting and function of PCSK9 relies on its C-terminal Cys-His-rich domain (CHRD), a region which allows for non-covalent binding with various membrane bound protein such as: amyloid precursor-like protein 2 (APLP2), Dynamin, amyloid precursor protein (APP), autosomal recessive hypercholesterolemia (ARH) protein, low density lipoprotein receptor-related protein 8 (Lrp8) and Annexin A2 (LoSurdo et al., EMBO 12:1300-1305 (2011); Ni et al., J. Biol. Chem. 285:12882-12891 (2010); Saavedra et al., J. Biol. Chem. 287:43492-43501 (2012); DeVay et al., J. Biol. Chem. 288:10805-10818 (2013); and Chaparro-Riggers et al., J. Biol. Chem. 287:11090-11097 (2012); the contents of all of which are hereby incorporated by reference.)

Exemplary Lysosomal Targeting Moieties

In some embodiments, a suitable lysosomal targeting moiety may be any proprotein convertase molecule, fragment or portion thereof (e.g., a motif or domain) capable of endocytosis to the lysosome. In some embodiments, the proprotein convertase molecule or fragment thereof, comprises a CHRD motif. In some embodiments, the proprotein convertase is a mammalian proprotein convertase. In some embodiments, the proprotein convertase is selected from the group consisting of PC1/3; PC2; Furin; PC4; PC5/6; PACE4, PC7, SKI-1/S1P and PCSK9. In some specific embodiments, the proprotein convertase is PCSK9.

In some embodiments, a suitable lysosomal targeting moiety may be any proprotein convertase molecule, fragment or portion thereof (e.g. a motif or domain) capable of binding, directly or indirectly, to the LDL receptor (LDLR). In some embodiments, the proprotein convertase molecule or fragment thereof, is capable of binding, directly or indirectly, to a secondary binding protein selected from the group consisting of amyloid precursor-like protein 2 (APLP2), Dynamin, amyloid precursor protein (APP), autosomal recessive hypercholesterolemia (ARH) protein, low density lipoprotein receptor-related protein 8 (Lrp8) and Annexin A. As used herein, binding to LDLR or secondary binding protein typically refers to a physiologically meaningful binding. For example, a physiologically meaningful binding typically has a dissociation constant (Kd) no greater than $10^{-7}$ under physiological conditions (e.g., pH 6-8, and in particular, pH 7.4).

In some embodiments, the lysosomal targeting moiety comprises the PCSK9 preprotein (including the PCSK9 signal peptide {N-terminal 30 amino acids} and propeptide {N-terminal amino acids from position 31 to 122}) (SEQ ID NO:6). In some embodiments, the lysosomal targeting moiety comprises the PCSK9 protein without the N-terminal signal and propeptide, i.e., PCSK9 Mature Protein (SEQ ID NO:7). In some embodiments, a lysosomal targeting moiety is a peptide fragment derived from human PCSK9 preprotein (SEQ ID NO:6). The amino acid sequences of a typical wild-type or naturally-occurring human PCSK9 preprotein and an auto-proteolytically cleaved human mature PCSK9 protein are shown in Table 4 below.

In some embodiments, a lysosomal targeting moiety has a sequence at least 50%, 55%, 60%, 65%, 70%, 75%, 80%, 85%, 90%, 95%, 98%, or 99% identical to the sequence of the PCSK9 preprotein (SEQ ID NO:6). In some embodiments, a lysosomal targeting moiety has a sequence at least 50%, 55%, 60%, 65%, 70%, 75%, 80%, 85%, 90%, 95%, 98%, or 99% identical to the sequence of PCSK9 Mature Protein (SEQ ID NO:7). In some embodiments, a lysosomal targeting moiety is a fragment of human PCSK9 Preprotein. In some embodiments, a lysosomal targeting moiety contains one or more N-terminal, C-terminal or internal deletions, or combinations thereof, in the sequence of human PCSK9 Preprotein (SEQ ID NO:6). In some embodiments, a lysosomal targeting moiety contains one or more N-terminal, C-terminal or internal deletions, or combinations thereof, in the sequence of the human PCSK9 Mature Protein (SEQ ID NO:7).

In some embodiments, a lysosomal targeting moiety is a modified human PCSK9 sequence (preprotein or mature form) containing amino acid substitutions, insertions or deletions. In some embodiments, the lysosomal targeting moiety has one or more amino acid substitutions, deletions or insertions within the catalytic domain of the preprotein or mature form of PCSK9. In some specific embodiments, the lysosomal targeting moiety has one or more mutations within the PCSK9 catalytic domain that diminish or enhance auto proteolytic cleavage. In some embodiments, the one or more mutations within the catalytic domain comprise a S386A substitution.

In some embodiments, the lysosomal targeting moiety has one or more mutations (amino acid substitutions, insertions or deletions) within the LDLR binding region that diminish or enhance binding to the LDL receptor. In some embodiments, the mutation within the LDLR binding region comprises a F379A substitution.

In some embodiments, the lysosomal targeting moiety has one or more mutations (amino acid substitutions, insertions or deletions) within the CHRD region of the protein. In some embodiments, the lysosomal targeting moiety has one or more mutations within the CHRD region that enhance

TABLE 4

Human PCSK9 Sequences

| | |
|---|---|
| PCSK9 Preprotein | MGTVSSRRSWWPLPLLLLLLLLLGPAGARAQEDEDGDYEELVLALRSEEDGLAE APEHGTTATFHRCAKDPWRLPGTYVVVLKEETHLSQSERTARRLQAQAARRGYL TKILHVFHGLLPGFLVKMSGDLLELALKLPHVDYIEEDSSVFAQSIPWNLERIT PPRYRADEYQPPDGGSLVEVYLLDTSIQSDHREIEGRVMVTDFENVPEEDGTRF HRQASKCDSHGTHLAGVVSGRDAGVAKGASMRSLRVLNCQGKGTVSGTLIGLEF IRKSQLVQPVGPLVVLLPLAGGYSRVLNAACQRLARAGVVLVTAAGNFRDDACL YSPASAPEVITVGATNAQDQPVTLGTLGTNFGRCVDLFAPGEDIIGASSDCSTC FVSQSGTSQAAAHVAGIAAMMLSAEPELTLAELRQRLIHFSAKDVINEAWFPED QRVLTPNLVAALPPSTHGAGWQLFCRTVWSAHSGPTRMATAVARCAPDEELLSC SSFSRSGKRRGERMEAQGGKLVCRAHNAFGGEGVYAIARCCLLPQANCSVHTAP PAEASMGTRVHCHQQGHVLTGCSSHWEVEDLGTHKPPVLRPRGQPNQCVGHREA SIHASCCHAPGLECKVKEHGIPAPQEQVTVACEEGWTLTGCSALPGTSHVLGAY AVDNTCVVRSRDVSTTGSTSEGAVTAVAICCRSRHLAQASQELQ (SEQ ID NO: 6) |
| PCSK9 Mature Protein | SIPWNLERITPPRYRADEYQPPDGGSLVEVYLLDTSIQSDHREIEGRVMVTDFE NVPEEDGTRFHRQASKCDSHGTHLAGVVSGRDAGVAKGASMRSLRVLNCQGKGT VSGTLIGLEFIRKSQLVQPVGPLVVLLPLAGGYSRVLNAACQRLARAGVVLVTA AGNFRDDACLYSPASAPEVITVGATNAQDQPVTLGTLGTNFGRCVDLFAPGEDI IGASSDCSTCFVSQSGTSQAAAHVAGIAAMMLSAEPELTLAELRQRLIHFSAKD VINEAWFPEDQRVLTPNLVAALPPSTHGAGWQLFCRTVWSAHSGPTRMATAVAR CAPDEELLSCSSFSRSGKRRGERMEAQGGKLVCRAHNAFGGEGVYAIARCCLLP QANCSVHTAPPAEASMGTRVHCHQQGHVLTGCSSHWEVEDLGTHKPPVLRPRGQ PNQCVGHREASIHASCCHAPGLECKVKEHGIPAPQEQVTVACEEGWTLTGCSAL PGTSHVLGAYAVDNTCVVRSRDVSTTGSTSEGAVTAVAICCRSRHLAQASQELQ (SEQ ID NO: 7) | binding to one or more secondary binding proteins selected from the group consisting of amyloid precursor-like protein 2 (APLP2), Dynamin, amyloid precursor protein (APP), autosomal recessive hypercholesterolemia (ARH) protein, low density lipoprotein receptor-related protein 8 (Lrp8) and Annexin A.

In some embodiments, the lysosomal targeting moiety has one or more mutations, substitutions, deletions or insertions within a region selected from the group consisting of the catalytic domain, propeptide, CHRD region, LDLR binding region and combinations thereof. In some embodiments, the one or more mutations are selected from the group consisting of S386A, F379A and combinations thereof. In some embodiments, the one or more mutations are selected from the group consisting of amino acid substitutions at positions R194 (elimination of LDL receptor binding), D186 and/or H226 (both elimination of protease activity); the substitution in these three cases may be A, as well as other amino acids such as L, G, V, and others.

Lysosomal Targeting Moiety Complex

In some embodiments, a suitable lysosomal targeting moiety is a protein complex comprising a proprotein convertase, or fragment thereof, and one or more auxiliary proteins. As used herein, the term "auxiliary protein" is used to describe a protein (i.e., full length, fragment, peptide or motif) non-covalently bound to the catalytic domain of a proprotein convertase, or fragment thereof, which is capable of inhibiting enzyme activity and/or of enhancing cellular uptake of the proprotein convertase.

In some embodiments, a suitable lysosomal targeting moiety is a protein complex comprising human PCSK9 and one or more auxiliary proteins. In some embodiments, the auxiliary protein comprises a protein (i.e., full length, fragment, peptide or motif) which binds within the catalytic domain of a human proprotein convertase. In some embodiments, the auxiliary protein partially occludes the catalytic site of PCSK9 or any other proprotein convertase when bound. In some embodiments, the auxiliary protein completely occludes the catalytic site of PCSK9 when bound. In some embodiments, the auxiliary protein binds within the catalytic domain of PCSK9 or any other proprotein convertase and reduces enzyme activity by at least 10%, 20%, 30%, 40%, 50%, 60%, 70%, 80%, 90% or 95%. In some embodiments, the auxiliary protein completely blocks enzyme activity when bound within the catalytic site of PCSK9 or any other proprotein convertase.

In some embodiments, the auxiliary protein binds the LDLR receptor binding site within the catalytic domain of PCSK9 or any other proprotein convertase.

In some embodiments, the auxiliary protein reduces binding between PCSK9, or any other proprotein convertase, and LDLR by at least 10%, 20%, 30%, 40%, 50%, 60%, 70%, 80%, 90% or 95%. In some embodiments, the auxiliary protein completely reduces binding of PCSK9, or any other proprotein convertase, to LDLR.

In some embodiments, the auxiliary protein enhances cellular uptake of PCSK9, or any other proprotein convertase, by at least 10%, 20%, 30%, 40%, 50%, 60%, 70%, 80%, 90% or 95%.

In some embodiments, an auxiliary protein comprises a proprotein convertase propeptide, or fragment thereof. In some embodiments, the propeptide or fragment thereof is derived from a proprotein convertase protein selected from the group consisting of PC1/3; PC2; Furin; PC4; PC5/6; PACE4, PC7, SKI-1/S1P and PCSK9. In some embodiments, the propeptide or fragment thereof is derived from PCSK9.

In some embodiments, the propeptide is derived from the PCSK9 preprotein (SEQ ID NO:6). In some embodiments, the propeptide comprises an amino acid sequence at least 50%, 60%, 70%, 80%, 85%, 90% or 95% identical SEQ ID NO:8. In some embodiments, the propeptide is identical to SEQ ID NO:8. The amino acid sequences of a propeptide derived from a typical wild-type or naturally-occurring human PCSK9 preprotein is shown in Table 5 below.

TABLE 5

| Human PCSK9 Propeptide Sequence | |
|---|---|
| PCSK9 Pro-peptide | QEDEDGDYEELVLALRSEEDGLAEAPEHGTTATFHRCAKD PWRLPGTYVVVLKEETHLSQSERTARRLQAQAARRGYLTK ILHVFHGLLPGFLVKMSGDLLELALKLPHVDYIEEDSSVF AQ (SEQ ID NO: 8) |

Association Between Lysosomal Enzyme and Lysosomal Targeting Moiety

A lysosomal enzyme and a targeting moiety can be associated, directly or indirectly. In some embodiments, a lysosomal enzyme and a targeting moiety are non-covalently associated. The association is typically stable at or about pH 7.4. For example, a targeting moiety can be biotinylated and bind avidin associated with a lysosomal enzyme. In some embodiments, a targeting moiety and a lysosomal enzyme are crosslinked to each other (e.g., using a chemical crosslinking agent).

In some embodiments, a targeting moiety is fused to a lysosomal enzyme as a fusion protein. The targeting moiety can be at the amino-terminus of the fusion protein, the carboxy-terminus, or can be inserted within the sequence of the lysosomal enzyme at a position where the presence of the targeting moiety does not unduly interfere with the therapeutic activity of the enzyme. Where a lysosomal enzyme is a heteromeric protein, one or more of the subunits can be associated with a targeting moeity.

Linker or Spacer

A lysosomal targeting moiety can be fused to the N-terminus or C-terminus of a lysosomal enzyme polypeptide, or inserted internally. The lysosomal targeting moiety can be fused directly to the lysosomal enzyme polypeptide or can be separated from the lysosomal enzyme polypeptide by a linker or a spacer. An amino acid linker or spacer is generally designed to be flexible or to interpose a structure, such as an alpha-helix, between two protein moieties. A linker or spacer can be relatively short, such as a "GGG" or a poly "GAG" sequence GGGGGAAAAAGGGGG (SEQ ID NO:9), a "GAP" sequence of GAP (SEQ ID NO:10), a "PolyGP" sequence of GGGGGP (SEQ ID NO:11), or can be longer, such as, for example, 10-50 (e.g., 10-20, 10-25, 10-30, 10-35, 10-40, 10-45, 10-50) amino acids in length. In some embodiments, various short linker sequences can be present in tandem repeats. For example, a suitable linker may contain the "GAG" amino acid sequence of GGGGGAAAAAGGGGG (SEQ ID NO:9) present in tandem repeats. In some embodiments, such a linker may further contain one or more "GAP" sequences, that frame the "GAG" sequence of GGGGGAAAAAGGGGG (SEQ ID NO:9). For example, in some embodiments a GAG2 linker may be used, which contains two tandem "GAG" repeats, each framed by a "GAP" sequence, such as GAPGGGGGAAAAAGGGGGGAPGGGGGAAAAA-GGGGGGAP (SEQ ID NO:12). In some embodiments a GAG3 linker may be used, which contains three tandem "GAG" repeats, each framed by two "GAP" sequences, such as GAPGGGGGAAAAAGGGGGGAPGGGGGAAAA-AGGGGGGAPGGGGGAAAAAGGGGG GAP (SEQ ID NO:13).

In some embodiments, a suitable linker or spacer may contain a sequence at least 50%, 55%, 60%, 65%, 70%, 75%, 80%, 85%, 90%, 95%, 98%, or 99% identical to any of the linker sequences described herein, including, but not limited to, SEQ ID NO:9, SEQ ID NO:10, SEQ ID NO:11, SEQ ID NO:12, or SEQ ID NO:13.

Additional linkers or spacers suitable for the invention are known in the art including those described in WO 2012122042, entitled "PEPTIDE LINKERS FOR POLYPEPTIDE COMPOSITIONS AND METHODS FOR USING SAME", which is incorporated by reference in its entirety.

It is contemplated that the association between a lysosomal enzyme and a lysosomal targeting moiety according to the present invention does not substantially alter enzyme activity. In some embodiments, the targeted therapeutic has an enzyme activity that is substantially similar or enhanced when compared to the corresponding native enzyme. In some embodiments, the enzyme activity of a targeted therapeutic retains at least about 60%, 65%, 70%, 75%, 80%, 85%, 90%, 95%, 98%, 99%, or 100% enzymatic activity as compared to the native enzyme. In some embodiments, the enzyme activity of a targeted therapeutic is enhanced by at least about 5%, 10%, 15%, 20%, 25%, 30%, 35%, 40%, 45%, 50%, 55%, 60%, 70%, 80%, 90% or 100% compared to the native enzyme.

In some embodiments, a targeted therapeutic of the present invention comprises a GAA or Naglu protein fused to a lysosomal targeting moiety. In some embodiments, the GAA or Naglu protein has a Km for a known substrate of at least about 0.10 nM (e.g., at least about 0.15 nM, 0.20 nM, 0.25 nM, 0.30 nM, or 0.35 nM).

It is also contemplated that in some embodiments, the targeted therapeutic of the present invention permits substantial binding between the lysosomal targeting moiety and a secondary binding protein, such as, but not limited to, amyloid precursor-like protein 2 (APLP2), Dynamin, amyloid precursor protein (APP), autosomal recessive hypercholesterolemia (ARH) protein, low density lipoprotein receptor-related protein 8 (Lrp8), LDLR and Annexin A. In some embodiments, the targeted therapeutic of the present invention may be engineered to permit substantial binding between the lysosomal targeting moiety and a secondary binding protein, such as, but not limited to amyloid precursor-like protein 2 (APLP2), Dynamin, amyloid precursor protein (APP), autosomal recessive hypercholesterolemia (ARH) protein, low density lipoprotein receptor-related protein 8 (Lrp8) and Annexin A, but shows a reduction or complete block in LDLR binding. In some embodiments, the level of LDLR or secondary binding protein binding of the targeted therapeutic may be tested using any of a variety of well-known binding assays, such as, but not limited to, radiolabeled run on assay, radiolabeled binding assay, ELISA, Surface Plasmone Resonance and Isothermal Titration calorimetry. In some embodiments, the level of LDLR or secondary binding protein binding of the targeted therapeutics of the invention may be evaluated by cellular uptake studies.

In some embodiments, the cellular uptake of a targeted therapeutic according to the present invention has a Kd of at least about 1.0e+2 nM (e.g., at least about 1.0e+3 nM, 1.0e+4 nM, or 1.0e+5 nM).

Production of Targeted Therapeutics

Targeted therapeutics according to the present invention may be produced via various methods known in the art. In some embodiments, a targeted therapeutic is a fusion protein comprising a lysosomal targeting moiety and a therapeutic protein (e.g., a lysosomal enzyme). In some embodiments, the fusion protein further comprises one or more auxiliary proteins. It is contemplated in accordance with the invention, that the targeted therapeutic, alone or further comprising an auxiliary binding protein, may be produced recombinantly. For example, a fusion protein according to the invention may be engineered using standard recombinant technology and produced using a cell culture system. In some embodiments, it is envisioned that the addition of an auxiliary protein may be achieved by co-expression of each component (fusion protein and auxiliary binding protein) to facilitate formation of the protein complex in vivo. Alternatively, in some embodiments, the auxiliary protein and the fusion protein may be recombinantely produced separately and brought together in vitro (e.g., following purification) to facilitate formation of the protein complex. In some embodiments, it is envisioned that a fusion protein is engineered and expressed that comprises a lysosomal targeting moiety (e.g., PCSK9) and a therapeutic protein (e.g., GAA) and at the N-terminus, separated by a proteolytic cleavage site (e.g., for Furin), a signal peptide and propeptide of a proprotein convertases (e.g., PCSK9). This proteolytic site will be cleaved intracellularly and the fusion comprising a lysosomal targeting moiety (e.g., PCSK9) and a therapeutic protein (e.g., GAA) will form a complex with the released propeptide (from which the signal peptide is removed within the ER).

Various prokaryotic and eukaryotic cells may be used for producing fusion proteins including, without limitation, cell lines derived from bacteria strains, yeast strains, insect cells, animal cells, mammalian cells and human cells. Aspects of the present invention also provide for expression constructs and the generation of recombinant stable cell lines useful for expressing fusion proteins which are disclosed in the present specification. In addition, aspects of the present invention also provide methods for producing cell lines that express fusion proteins using the disclosed nucleic acid sequences of the present specification.

Nucleic Acids Encoding Recombinant Fusion Proteins

In some embodiments, nucleic acid molecules are provided comprising nucleic acid sequences encoding for a recombinant fusion protein (herein referred to as a transgene), such as GAA and Naglu fusion proteins described in various embodiments herein. In some embodiments, the nucleic acid encoding a transgene may be modified to provide increased expression of the fusion protein, which is also referred to as codon optimization. For example, the nucleic acid encoding a transgene can be modified by altering the open reading frame for the coding sequence. As used herein, the term "open reading frame" is synonymous with "ORF" and means any nucleotide sequence that is potentially able to encode a protein, or a portion of a protein. An open reading frame usually begins with a start codon (represented as, e.g. AUG for an RNA molecule and ATG in a DNA molecule in the standard code) and is read in codon-triplets until the frame ends with a STOP codon (represented as, e.g. UAA, UGA or UAG for an RNA molecule and TAA, TGA or TAG in a DNA molecule in the standard code). As used herein, the term "codon" means a sequence of three nucleotides in a nucleic acid molecule that specifies a particular amino acid during protein synthesis; also called a triplet or codon-triplet. For example, of the 64 possible codons in the standard genetic code, two codons, GAA and GAG encode the amino acid Glutamine whereas the codons AAA and AAG specify the amino acid Lysine. In the standard genetic code three codons are stop codons, which do not specify an amino acid. As used herein, the term "synonymous codon" means any and all of the codons that code for a single amino acid. Except for Methionine and Tryptophan, amino acids are coded by two to six synonymous codons. For example, in the standard genetic code the four synonymous codons that code for the amino acid Alanine are GCA, GCC, GCG and GCU, the two synonymous codons that specify Glutamine are GAA and GAG and the two synonymous codons that encode Lysine are AAA and AAG.

In some embodiments, a nucleic acid encoding the open reading frame of fusion protein may be modified using standard codon optimization methods. Various commercial algorithms for codon optimization are available and can be used to practice the present invention. Typically, codon optimization does not alter the encoded amino acid sequences. In some embodiments, codon optimization may lead to amino acids alteration such as substitution, deletion or insertion. Typically, such amino acid alteration does not substantially alter the protein activity.

Exemplary nucleic acid sequences encoding PCSK9-GAA, Naglu-PCSK9 and the PCSK9 propeptide are each respectively shown in SEQ ID NO:14, 15 and 16 below.

SEQ ID NO:14 Exemplary nucleic acid sequence encoding PCSK9-GAA.

ATGGGCACCGTCAGCTCCAGGCGGTCCTGGTGGCCGCTGCCACTGCTGCT
GCTGCTGCTGCTCCTGGGTCCCGCGGGCGCCCGTGCGAGCATCCCGT
GGAACCTGGAGCGGATTACCCCTCCACGGTACCGGGCGGATGAATACCAG
CCCCCCGACGGAGGCAGCCTGGTGGAGGTGTATCTCCTAGACACCAGCAT
ACAGAGTGACCACCGGGAAATCGAGGGCAGGGTCATGGTCACCGACTTCG
AGAATGTGCCCGAGGAGGACGGGACCCGCTTCCACAGACAGGCCAGCAAG
TGTGACAGTCATGGCACCCACCTGGCAGGGGTGGTCAGCGGCCGGGATGC
CGGCGTGGCCAAGGGTGCCAGCATGCGCAGCCTGCGCGTGCTCAACTGCC
AAGGGAAGGGCACGGTTAGCGGCACCCTCATAGGCCTGGAGTTTATTCGG
AAAAGCCAGCTGGTCCAGCCTGTGGGGCCACTGGTGGTGCTGCTGCCCCT
GGCGGGTGGGTACAGCCGCGTCCTCAACGCCGCCTGCCAGCGCCTGGCGA
GGGCTGGGGTCGTGCTGGTCACCGCTGCCGGCAACTTCCGGGACGATGCC
TGCCTCTACTCCCCAGCCTCAGCTCCCGAGGTCATCACAGTTGGGGCCAC
CAATGCCCAAGACCAGCCGGTGACCCTGGGGACTTTGGGGACCAACTTTG
GCCGCTGTGTGGACCTCTTTGCCCCAGGGGAGGACATCATTGGTGCCTCC
AGCGACTGCAGCACCTGCGCTGTGTCACAGAGTGGGACAGCACAGGCTGC
TGCCCACGTGGCTGGCATTGCAGCCATGATGCTGTCTGCCGAGCCGGAGC
TCACCCTGGCCGAGTTGAGGCAGAGACTGATCCACTTCTCTGCCAAAGAT
GTCATCAATGAGGCCTGGTTCCCTGAGGACCAGCGGGTACTGACCCCCAA
CCTGGTGGCCGCCCTGCCCCCAGCACCCATGGGCAGGTTGGCAGCTGT
TTTGCAGGACTGTATGGTCAGCACACTCGGGGCCTACACGGATGGCCACA
GCCGTCGCCCGCTGCGCCCCAGATGAGGAGCTGCTGAGCTGCTCCAGTTT
CTCCAGGAGTGGGAAGCGGCGGGGCGAGCGCATGGAGGCCCAAGGGGCA

AGCTGGTCTGCCGGGCCCACAACGCTTTTGGGGGTGAGGGTGTCTACGCC
ATTGCCAGGTGCTGCCTGCTACCCCAGGCCAACTGCAGCGTCCACACAGC
TCCACCAGCTGAGGCCAGCATGGGGACCCGTGTCCACTGCCACCAACAGG
GCCACGTCCTCACAGGCTGCAGCTCCCACTGGGAGGTGGAGGACCTTGGC
ACCCACAAGCCGCCTGTGCTGAGGCCACGAGGTCAGCCCAACCAGTGCGT
GGGCCACAGGGAGGCCAGCATCCACGCTTCCTGCTGCCATGCCCCAGGTC
TGGAATGCAAAGTCAAGGAGCATGGAATCCCGGCCCCTCAGGAGCAGGTG
ACCGTGGCCTGCGAGGAGGGCTGGACCCTGACTGGCTGCAGTGCCCTCCC
TGGGACCTCCCACGTCCTGGGGGCCTACGCCGTAGACAACACGTGTGTAG
TCAGGAGCCGGGACGTCAGCACTACAGGCAGCACCAGCGAAGGGCCGTG
ACAGCCGTTGCCATCTGCTGCCGGAGCCGGCACCTGGCGCAGGCCTCCCA
GGAGCTCCAGGGAGGTGGAGCACACCCCGGCCGTCCCAGAGCAGTGCCCA
CACAGTGCGACGTCCCCCCAACAGCCGCTTCGATTGCGCCCCTGACAAG
GCCATCACCCAGGAACAGTGCGAGGCCCGCGGCTGTTGCTACATCCCTGC
AAAGCAGGGGCTGCAGGGAGCCCAGATGGGGCAGCCCTGGTGCTTCTTCC
CACCCAGCTACCCCAGCTACAAGCTGGAGAACCTGAGCTCCTCTGAAATG
GGCTACACGGCCACCCTGACCCGTACCACCCCCACCTTCTTCCCCAAGGA
CATCCTGACCCTGCGGCTGGACGTGATGATGGAGACTGAGAACCACTTGC
CTCCCACGATCAAAGATCCAGCTAACAGGCGCTACGAGGTGCCCTTGGAG
ACCCCGCATGTCCACAGCCGGGCACCGTCCCCACTCTACAGCGTGGAGTT
CTCCGAGGAGCCCTTCGGGGTGATCGTGCGCCGGCAGCTGGACGGCCGCG
TGCTGCTGAACACGACGGTGGCGCCCCTGTTCTTTGCGGACCAGTTCCTT
CAGCTGTCCACCTCGCTGCCCTCGCAGTATATCACAGGCCTCGCCGAGCA
CCTCAGTCCCCTGATGCTCAGCACCAGCTGGACCAGGATCACCCTGTGGA
ACCGGGACCTTGCGCCCACGCCCGGTGCGAACCTCTACGGGTCTCACCCT
TTCTACCTGGCGCTGGAGGACGGCGGGTCGGCACACGGGGTGTTCCTGCT
AAACAGCAATGCCATGGATGTGGTCCTGCAGCCGAGCCCTGCCCTTAGCT
GGAGGTCGACAGGTGGGATCCTGGATGTCTACATCTTCCTGGGCCCAGAG
CCCAAGAGCGTGGTGCAGCAGTACCTGGACGTTGTGGGATACCCGTTCAT
GCCGCCATACTGGGGCCTGGGCTTCCACCTGTGCCGCTGGGGCTACTCCT
CCACCGCTATCACCCGCCAGGTGGTGGAGAACATGACCAGGGCCCACTTC
CCCCTGGACGTCCAGTGGAACGACCTGGACTACATGGACTCCGGAGGGA
CTTCACGTTCAACAAGGATGGCTTCCGGGACTTCCCGGCCATGGTGCAGG
AGCTGCACCAGGGCGGCCGGCGCTACATGATGATCGTGGATCCTGCCATC
AGCAGCTCGGGCCCTGCCGGGAGCTACAGGCCCTACGACGAGGGTCTGCG
GAGGGGGGTTTTCATCACCAACGAGACCGGCCAGCCGCTGATTGGGAAGG

-continued

*TATGGCCCGGGTCCACTGCCTTCCCCGACTTCACCAACCCCACAGCCCTG*

*GCCTGGTGGGAGGACATGGTGGCTGAGTTCCATGACCAGGTGCCCTTCGA*

*CGGCATGTGGATTGACATGAACGAGCCTTCCAACTTCATCAGGGGCTCTG*

*AGGACGGCTGCCCCAACAATGAGCTGGAGAACCCACCCTACGTGCCTGGG*

*GTGGTTGGGGGGACCCTCCAGGCGGCCACCATCTGTGCCTCCAGCCACCA*

*GTTTCTCTCCACACACTACAACCTGCACAACCTCTACGGCCTGACCGAAG*

*CCATCGCCTCCCACAGGGCGCTGGTGAAGGCTCGGGGACACGCCCATTT*

*GTGATCTCCCGCTCGACCTTTGCTGGCCACGGCCGATACGCCGGCCACTG*

*GACGGGGACGTGTGGAGCTCCTGGGAGCAGCTCGCCTCCTCCGTGCCAG*

*AAATCCTGCAGTTTAACCTGCTGGGGGTGCCTCTGGTCGGGGCCGACGTC*

*TGCCGGCTTCCTGGGCAACACCTCAGAGGAGCTGTGTGTGCGCTGGACCCA*

*GCTGGGGGCCTTCTACCCCTTCATGCGGAACCACAACAGCCTGCTCAGTC*

*TGCCCCAGGAGCCGTACAGCTTCAGCGAGCCGGCCCAGCAGGCCATGAGG*

*AAGGCCCTCACCCTGCGCTACGCACTCCTCCCCCACCTCTACACACTGTT*

*CCACCAGGCCCACGTCGCGGGGGAGACCGTGGCCCGGCCCCTCTTCCTGG*

*AGTTCCCCAAGGACTCTAGCACCTGGACTGTGGACCACCAGCTCCTGTGG*

*GGGGAGGCCCTGCTCATCACCCCAGTGCTCCAGGCCGGGAAGGCCGAAGT*

*GACTGGCTACTTCCCCTTGGGCACATGGTACGACCTGCAGACGGTGCCAG*

*TAGAGGCCCTTGGCAGCCTCCCACCCCCACCTGCAGCTCCCCGTGAGCCA*

*GCCATCCACAGCGAGGGCAGTGGGTGACGCTGCCGGCCCCCCTGGACAC*

*CATCAACGTCCACCTCCGGGCTGGGTACATCATCCCCCTGCAGGGCCCTG*

*GCCTCACAACCACAGAGTCCCGCCAGCAGCCCATGGCCCTGGCTGTGGCC*

*CTGACCAAGGGTGGGGAGGCCCGAGGGGAGCTGTTCTGGGACGATGGAGA*

*GAGCCTGGAAGTGCTGGAGCGAGGGGCCTACACACAGGTCATCTTCCTGG*

*CCAGGAATAACACGATCGTGAATGAGCTGGTACGTGTGACCAGTGAGGGA*

*GCTGGCCTGCAGCTGCAGAAGGTGACTGTCCTGGGCGTGGCCACGGCGCC*

*CCAGCAGGTCCTCTCCAACGGTGTCCCTGTCTCCAACTTCACCTACAGCC*

*CCGACACCAAGGTCCTGGACATCTGTGTCTCGCTGTTGATGGGAGAGCAG*

*TTTCTCGTCAGCTGGTGTTAG*

(1) The nucleotide sequence encoding PCSK9 signal peptide is underlined.
(2) The nucleotide sequence encoding PCSK9 Mature Protein (except nucleotide sequences encoding mutations F379A and S386A, which are underlined) is not underlined, bold or in italics.
(3) The nucleotide sequence encoding the amino acid sequence of the GlyGlyGly linker is underlined.
(4) The nucleotide sequence encoding Mature Form GAA Protein amino acid sequence (aa70-952) is bold and in italics.

SEQ ID NO:15 Exemplary nucleic acid sequence encoding Naglu-PCSK9.

<u>ATGGAGGCGGTGGCGGTGGCCGCGGCGGTGGGGGTCCTTCTCCTGGCCGG</u>

<u>GGCCGGGGCGCGGCAGGCGACGAGGCCCGGGAGGCGGCGGCCGTGCGGG</u>

CGCTCGTGGCCCGGCTGCTGGGGCCAGGCCCCGCGGCCGACTTCTCCGTG

TCGGTGGAGCGCGCTCTGGCTGCCAAGCCGGGCTTGGACACCTACAGCCT

GGGCGGCGGCGGCGCGGCGCGCGTGCGGGTGCGCGGCTCCACGGGCGTGG

CGGCCGCCGCGGGGCTGCACCGCTACCTGCGCGACTTCTGTGGCTGCCAC

GTGGCCTGGTCCGGCTCTCAGCTGCGCCTGCCGCGGCCACTGCCAGCCGT

GCCGGGGGAGCTGACCGAGGCCACGCCCAACAGGTACCGCTATTACCAGA

ATGTGTGCACGCAAAGCTACTCCTTCGTGTGGTGGGACTGGGCCCGCTGG

GAGCGAGAGATAGACTGGATGGCGCTGAATGGCATCAACCTGGCACTGGC

CTGGAGCGGCCAGGAGGCCATCTGGCAGCGGGTGTACCTGGCCTTGGGCC

TGACCCAGGCAGAGATCAATGAGTTCTTTACTGGTCCTGCCTTCCTGGCC

TGGGGGCGAATGGGCAACCTGCACACCTGGGATGGCCCCCTGCCCCCCTC

CTGGCACATCAAGCAGCTTTACCTGCAGCACCGGGTCCTGGACCAGATGC

GCTCCTTCGGCATGACCCCAGTGCTGCCTGCATTCGCGGGGCATGTTCCC

GAGGCTGTCACCAGGGTGTTCCCTCAGGTCAATGTCACGAAGATGGGCAG

TTGGGGCCACTTTAACTGTTCCTACTCCTGCTCCTTCCTTCTGGCTCCGG

AAGACCCCATATTCCCCATCATCGGGAGCCTCTTCCTGCGAGAGCTGATC

AAAGAGTTTGGCACAGACCACATCTATGGGGCCGACACTTTCAATGAGAT

GCAGCCACCTTCCTCAGAGCCCTCCTACCTTGCCGCAGCCACCACTGCCG

TCTATGAGGCCATGACTGCAGTGGATACTGAGGCTGTGTGGCTGCTCCAA

GGCTGGCTCTTCCAGCACCAGCCGCAGTTCTGGGGGCCCGCCCAGATCAG

GGCTGTGCTGGGAGCTGTGCCCCGTGGCCGCCTCCTGGTTCTGGACCTGT

TTGCTGAGAGCCAGCCTGTGTATACCCGCACTGCCTCCTTCCAGGGCCAG

CCCTTCATCTGGTGCATGCTGCACAACTTTGGGGGAAACCATGGTCTTTT

TGGAGCCCTAGAGGCTGTGAACGGAGGCCCAGAAGCTGCCCGCCTCTTCC

CCAACTCCACCATGGTAGGCACGGGCATGGCCCCGAGGGCATCAGCCAG

AACGAAGTGGTCTATTCCCTCATGGCTGAGCTGGGCTGGCGAAAGGACCC

AGTGCCAGATTTGGCAGCCTGGGTGACCAGCTTTGCCGCCCGGCGGTATG

GGGTCTCCCACCCGGACGCAGGGGCAGCGTGGAGGCTACTGCTCCGGAGT

GTGTACAACTGCTCCGGGGAGGCCTGCAGGGGCCACAATCGTAGCCCGCT

GGTCAGGCGGCCGTCCCTACAGATGAATACCAGCATCTGGTACAACCGAT

CTGATGTGTTTGAGGCCTGGCGGCTGCTGCTCACATCTGCTCCCTCCCTG

GCCACCAGCCCCGCCTTCCGCTACGACCTGCTGGACCTCACTCGGCAGGC

AGTGCAGGAGCTGGTCAGCTTGTACTATGAGGAGGCAAGAAGCGCCTACC

TGAGCAAGGAGCTGGCCTCCCTGTTGAGGGCTGGAGGCGTCCTGGCCTAT

GAGCTGCTGCCGGCACTGGACGAGGTGCTGGCTAGTGACAGCCGCTTCTT

GCTGGGCAGCTGGCTAGAGCAGGCCCGAGCAGCGGCAGTCAGTGAGGCCG

AGGCCGATTTCTACGAGCAGAACAGCCGCTACCAGCTGACCTTGTGGGGG

```
CCAGAAGGCAACATCCTGGACTATGCCAACAAGCAGCTGGCGGGGTTGGT

GGCCAACTACTACACCCCTCGCTGGCGGCTTTTCCTGGAGGCGCTGGTTG

ACAGTGTGGCCCAGGGCATCCCTTTCCAACAGCACCAGTTTGACAAAAAT

GTCTTCCAACTGGAGCAGGCCTTCGTTCTCAGCAAGCAGAGGTACCCCAG

CCAGCCGCGAGGAGACACTGTGGACCTGGCCAAGAAGATCTTCCTCAAAT

ATTACCCCGCTGGGTGGCCGGCTCTTGGGGAGGTGGAAGCATCCCGTGG

AACCTGGAGCGGATTACCCCTCCACGGTACCGGGCGGATGAATACCAGCC

CCCCGACGGAGGCAGCCTGGTGGAGGTGTATCTCCTAGACACCAGCATAC

AGAGTGACCACCGGGAAATCGAGGGCAGGGTCATGGTCACCGACTTCGAG

AATGTGCCCGAGGAGGACGGGACCCGCTTCCACAGACAGGCCAGCAAGTG

TGACAGTCATGGCACCCACCTGGCAGGGGTGGTCAGCGGCCGGGATGCCG

GCGTGGCCAAGGGTGCCAGCATGCGCAGCCTGCGCGTGCTCAACTGCCAA

GGGAAGGGCACGGTTAGCGGCACCCTCATAGGCCTGGAGTTTATTCGGAA

AAGCCAGCTGGTCCAGCCTGTGGGGCCACTGGTGGTGCTGCTGCCCCTGG

CGGGTGGGTACAGCCGCGTCCTCAACGCCGCCTGCCAGCGCCTGGCGAGG

GCTGGGGTCGTGCTGGTCACCGCTGCCGGCAACTTCCGGGACGATGCCTG

CCTCTACTCCCCAGCCTCAGCTCCCGAGGTCATCACAGTTGGGGCCACCA

ATGCCCAAGACCAGCCGGTGACCCTGGGGACTTTGGGGACCAACTTTGGC

CGCTGTGTGGACCTCTTTGCCCCAGGGGAGGACATCATTGGTGCCTCCAG

CGACTGCAGCACCTGCGCTGTGTCACAGAGTGGGACAGCACAGGCTGCTG

CCCACGTGGCTGGCATTGCAGCCATGATGCTGTCTGCCGAGCCGGAGCTC

ACCCTGGCCGAGTTGAGGCAGAGACTGATCCACTTCTCTGCCAAAGATGT

CATCAATGAGGCCTGGTTCCCTGAGGACCAGCGGGTACTGACCCCCAACC

TGGTGGCCGCCCTGCCCCCCAGCACCCATGGGGCAGGTTGGCAGCTGTTT

TGCAGGACTGTATGGTCAGCACACTCGGGGCCTACACGGATGGCCACAGC

CGTCGCCCGCTGCGCCCCAGATGAGGAGCTGCTGAGCTGCTCCAGTTTCT

CCAGGAGTGGGAAGCGGCGGGGCGAGCGCATGGAGGCCCAAGGGGGCAAG

CTGGTCTGCCGGGCCCACAACGCTTTTGGGGGTGAGGGTGTCTACGCCAT

TGCCAGGTGCTGCCTGCTACCCCAGGCCAACTGCAGCGTCCACACAGCTC

CACCAGCTGAGGCCAGCATGGGGACCCGTGTCCACTGCCACCAACAGGGC

CACGTCCTCACAGGCTGCAGCTCCCACTGGGAGGTGGAGGACCTTGGCAC

CCACAAGCCGCCTGTGCTGAGGCCACGAGGTCAGCCCAACCAGTGCGTGG

GCCACAGGGAGGCCAGCATCCACGCTTCCTGCTGCCATGCCCCAGGTCTG

GAATGCAAAGTCAAGGAGCATGGAATCCCGGCCCCTCAGGAGCAGGTGAC

CGTGGCCTGCGAGGAGGGCTGGACCCTGACTGGCTGCAGTGCCCTCCCTG

GGACCTCCCACGTCCTGGGGGCCTACGCCGTAGACAACACGTGTGTAGTC

AGGAGCCGGGACGTCAGCACTACAGGCAGCACCAGCGAAGGGGCCGTGAC

AGCCGTTGCCATCTGCTGCCGGAGCCGGCACCTGGCGCAGGCCTCCCAGG

AGCTCCAGTAG
```

(1) The nucleotide sequence encoding Naglu signal peptide is underlined.

(2) The nucleotide sequence encoding Mature Form of Naglu is not underlined, bold or in italics.

(3) The nucleotide sequence encoding the amino acid sequence of the GlyGlyGly linker is underlined.

(4) The nucleotide sequence encoding PCSK9 Mature Protein (except the nucleotide sequences encoding mutations F379A and S386A, which are additionally underlined) is in italics.

SEQ ID NO:16 Exemplary nucleic acid sequence encoding PCSK9 propeptide and PCSK9 N-terminal signal peptide.

```
ATGGGCACCGTCAGCTCCAGGCGGTCCTGGTGGCCGCTGCCACTGCTGCT

GCTGCTGCTGCTGCTCCTGGGTCCCGCGGGCGCCCGTGCGCAGGAGGACG

AGGACGGCGACTACGAGGAGCTGGTGCTAGCCTTGCGTTCCGAGGAGGAC

GGCCTGGCCGAAGCACCCGAGCACGGAACCACAGCCACCTTCCACCGCTG

CGCCAAGGATCCGTGGAGGTTGCCTGGCACCTACGTGGTGGTGCTGAAGG

AGGAGACCCACCTCTCGCAGTCAGAGCGCACTGCCCGCCGCCTGCAGGCC

CAGGCTGCCCGCCGGGGATACCTCACCAAGATCCTGCATGTCTTCCATGG

CCTTCTTCCTGGCTTCCTGGTGAAGATGAGTGGCGACCTGCTGGAGCTGG

CCTTGAAGTTGCCCCATGTCGACTACATCGAGGAGGACTCCTCTGTCTTT

GCCCAGTGA
```

(1) The nucleotide sequence encoding PCSK9 signal peptide is underlined.

(2) The nucleotide sequence encoding PCSK9 propeptide is in italics.

In some embodiments, a nucleotide change may alter a synonymous codon within the open reading frame in order to agree with the endogenous codon usage found in a particular heterologous cell selected for expression. Alternatively or additionally, a nucleotide change may alter the G+C content within the open reading frame to better match the average G+C content of open reading frames found in endogenous nucleic acid sequence present in the heterologous host cell. A nucleotide change may also alter a poly-mononucleotide region or an internal regulatory or structural site found within a protein sequence. Thus, a variety of modified or optimized nucleotide sequences are envisioned including, without limitation, nucleic acid sequences providing increased expression of a fusion protein in a prokaryotic cell; yeast cell; insect cell; and in a mammalian cell.

Thus, in some embodiments, a nucleic acid encoding a PCSK9-GAA fusion protein suitable for the present invention comprises a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:14. In some embodiments, a nucleic acid encoding a Naglu-PCSK9 fusion protein suitable for the present invention comprises a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:15. In some embodiments, a nucleic acid encoding a PCSK9 propetiped suitable for the present invention comprises a nucleotide sequence at least 50%, 55%, 60%, 65%, 70%, 75%, 80%, 85%, 90%, 91%, 92%, 93%, 94%, 95%, 96%, 97%, 98%, 99% or more identical to SEQ ID NO:16. A modified nucleic acid may or may not result in amino acid sequence alterations in a fusion protein. In the event there is amino acid alteration, such alteration typically does not substantially alter the biological activity of the protein.

Expression Vectors

A nucleic acid sequence encoding a fusion protein or auxiliary binding protein as described in the present application, can be molecularly cloned (inserted) into a suitable vector for propagation or expression in a host cell. A wide variety of expression vectors can be used to practice the present invention, including, without limitation, a prokaryotic expression vector; a yeast expression vector; an insect expression vector and a mammalian expression vector. Exemplary vectors suitable for the present invention include, but are not limited to, viral based vectors (e.g., AAV based vectors, retrovirus based vectors, plasmid based vectors). Typically, a nucleic acid encoding a fusion protein is operably linked to various regulatory sequences or elements.

Regulatory Sequences or Elements

Various regulatory sequences or elements may be incorporated in an expression vector suitable for the present invention. Exemplary regulatory sequences or elements include, but are not limited to, promoters, enhancers, repressors or suppressors, 5' untranslated (or non-coding) sequences, introns, 3' untranslated (or non-coding) sequences.

As used herein, a "Promoter" or "Promoter sequence" is a DNA regulatory region capable of binding an RNA polymerase in a cell (e.g., directly or through other promoter bound proteins or substances) and initiating transcription of a coding sequence. A promoter sequence is, in general, bound at its 3' terminus by the transcription initiation site and extends upstream (5' direction) to include the minimum number of bases or elements necessary to initiate transcription at any level. The promoter may be operably associated with or operably linked to the expression control sequences, including enhancer and repressor sequences or with a nucleic acid to be expressed. In some embodiments, the promoter may be inducible. In some embodiments, the inducible promoter may be unidirectional or bio-directional. In some embodiments, the promoter may be a constitutive promoter. In some embodiments, the promoter can be a hybrid promoter, in which the sequence containing the transcriptional regulatory region is obtained from one source and the sequence containing the transcription initiation region is obtained from a second source. Systems for linking control elements to coding sequence within a transgene are well known in the art (general molecular biological and recombinant DNA techniques are described in Sambrook, Fritsch, and Maniatis, *Molecular Cloning: A Laboratory Manual*, Second Edition, Cold Spring Harbor Laboratory Press, Cold Spring Harbor, N.Y., 1989, which is incorporated herein by reference). Commercial vectors suitable for inserting a transgene for expression in various host cells under a variety of growth and induction conditions are also well known in the art.

In some embodiments, a specific promoter may be used to control expression of the transgene in a mammalian host cell such as, but are not limited to, SRα-promoter (Takebe et al., Molec. and Cell. Bio. 8:466-472 (1988)), the human CMV immediate early promoter (Boshart et al., Cell 41:521-530 (1985); Foecking et al., Gene 45:101-105 (1986)), human CMV promoter, the human CMV5 promoter, the murine CMV immediate early promoter, the EF1-α-promoter, a hybrid CMV promoter for liver specific expression (e.g., made by conjugating CMV immediate early promoter with the transcriptional promoter elements of either human α-1-antitrypsin (HAT) or albumin (HAL) promoter), or promoters for hepatoma specific expression (e.g., wherein the transcriptional promoter elements of either human albumin (HAL; about 1000 bp) or human α-1-antitrypsin (HAT, about 2000 bp) are combined with a 145 long enhancer element of human α-1-microglobulin and bikunin precursor gene (AMBP); HAL-AMBP and HAT-AMBP); the SV40 early promoter region (Benoist at al., Nature 290:304-310 (1981)), the *Orgyia pseudotsugata* immediate early promoter, the herpes thymidine kinase promoter (Wagner at al., Proc. Natl. Acad. Sci. USA 78:1441-1445 (1981)); or the regulatory sequences of the metallothionein gene (Brinster et al., Nature 296:39-42 (1982)). In some embodiments, the mammalian promoter is a constitutive promoter such as, but not limited to, the hypoxanthine phosphoribosyl transferase (HPTR) promoter, the adenosine deaminase promoter, the pyruvate kinase promoter, the beta-actin promoter as well as other constitutive promoters known to those of ordinary skill in the art.

In some embodiments, a specific promoter may be used to control expression of a transgene in a prokaryotic host cell such as, but are not limited to, the β-lactamase promoter (Villa-Komaroff et al., Proc. Natl. Acad. Sci. USA 75:3727-3731 (1978)); the tac promoter (DeBoer et al., Proc. Natl. Acad. Sci. USA 80:21-25 (1983)); the T7 promoter, the T3 promoter, the M13 promoter or the M16 promoter; in a yeast host cell such as, but are not limited to, the GAL1, GAL4 or GAL10 promoter, the ADH (alcohol dehydrogenase) promoter, PGK (phosphoglycerol kinase) promoter, alkaline phosphatase promoter, glyceraldehyde-3-phosphate dehydrogenase III (TDH3) promoter, glyceraldehyde-3-phosphate dehydrogenase II (TDH2) promoter, glyceraldehyde-3-phosphate dehydrogenase I (TDH1) promoter, pyruvate kinase (PYK), enolase (ENO), or triose phosphate isomerase (TPI).

In some embodiments, the promoter may be a viral promoter, many of which are able to regulate expression of a transgene in several host cell types, including mammalian cells. Viral promoters that have been shown to drive constitutive expression of coding sequences in eukaryotic cells include, for example, simian virus promoters, herpes simplex virus promoters, papilloma virus promoters, adenovirus promoters, human immunodeficiency virus (HIV) promoters, Rous sarcoma virus promoters, cytomegalovirus (CMV) promoters, the long terminal repeats (LTRs) of Moloney murine leukemia virus and other retroviruses, the thymidine kinase promoter of herpes simplex virus as well as other viral promoters known to those of ordinary skill in the art.

In some embodiments, the gene control elements of an expression vector may also include 5' non-transcribing and 5' non-translating sequences involved with the initiation of transcription and translation, respectively, such as a TATA box, capping sequence, CAAT sequence, Kozak sequence and the like. Enhancer elements can optionally be used to increase expression levels of a polypeptide or protein to be expressed. Examples of enhancer elements that have been shown to function in mammalian cells include the SV40 early gene enhancer, as described in Dijkema et al., EMBO J. (1985) 4: 761 and the enhancer/promoter derived from the long terminal repeat (LTR) of the Rous Sarcoma Virus (RSV), as described in Gorman et al., Proc. Natl. Acad. Sci. USA (1982b) 79:6777 and human cytomegalovirus, as described in Boshart et al., Cell (1985) 41:521. Genetic control elements of an expression vector will also include 3' non-transcribing and 3'non-translating sequences involved with the termination of transcription and translation. Respectively, such as a poly polyadenylation (polyA) signal for stabilization and processing of the 3' end of an mRNA transcribed from the promoter. Poly A signals included, for example, the rabbit beta globin polyA signal, bovine growth hormone polyA signal, chicken beta globin terminator/polyA signal, or SV40 late polyA region.

Selectable Markers

Expression vectors will preferably but optionally include at least one selectable marker. In some embodiments, the selectable maker is a nucleic acid sequence encoding a resistance gene operably linked to one or more genetic regulatory elements, to bestow upon the host cell the ability to maintain viability when grown in the presence of a cyctotoxic chemical and/or drug. In some embodiments, a selectable agent may be used to maintain retention of the expression vector within the host cell. In some embodiments, the selectable agent is may be used to prevent modification (i.e. methylation) and/or silencing of the transgene sequence within the expression vector. In some embodiments, a selectable agent is used to maintain episomal expression of the vector within the host cell. In some embodiments, the selectable agent is used to promote stable integration of the transgene sequence into the host cell genome. In some embodiments, an agent and/or resistance gene may include, but is not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), zeomycin, mycophenolic acid, or glutamine synthetase (GS, U.S. Pat. Nos. 5,122,464; 5,770,359; 5,827,739) for eukaryotic host cell; tetracycline, ampicillin, kanamycin or chlorampenichol for a prokaryotic host cell; and URA3, LEU2, HIS3, LYS2, HIS4, ADE8, CUP1 or TRP1 for a yeast host cell.

Expression vectors may be transfected, transformed or transduced into a host cell. As used herein, the terms "transfection," "transformation" and "transduction" all refer to the introduction of an exogenous nucleic acid sequence into a host cell. In some embodiments, expression vectors containing nucleic acid sequences encoding a fusion therapeutic glycoprotein is transfected, transformed or transduced into a host cell. In some embodiments, one or more expression vectors containing nucleic acid sequences encoding a fusion therapeutic glycoprotein are transfected, transformed or transduced into a host cell sequentially. For example, a vector encoding a first fusion therapeutic glycoprotein protein may be transfected, transformed or transduced into a host cell, followed by the transfection, transformation or transduction of a vector encoding a second fusion therapeutic glycoprotein, and vice versa. Examples of transformation, transfection and transduction methods, which are well known in the art, include liposome delivery, i.e., Lipofectamine™ (Gibco BRL) Method of Hawley-Nelson, Focus 15:73 (1193), electroporation, CaPO$_4$ delivery method of Graham and van der Erb, *Virology*, 52:456-457 (1978), DEAE-Dextran medicated delivery, microinjection, biolistic particle delivery, polybrene mediated delivery, cationic mediated lipid delivery, transduction, and viral infection, such as, e.g., retrovirus, lentivirus, adenovirus adeno-associated virus and Baculovirus (Insect cells). General aspects of cell host transformations have been described in the art, such as by Axel in U.S. Pat. No. 4,399,216; Sambrook, supra, Chapters 1-4 and 16-18; Ausubel, supra, chapters 1, 9, 13, 15, and 16. For various techniques for transforming mammalian cells, see Keown et al., *Methods in Enzymology* (1989), Keown et al., *Methods in Enzymology*, 185:527-537 (1990), and Mansour et al., *Nature*, 336:348-352 (1988).

Once introduced inside cells, expression vectors may be integrated stably in the genome or exist as extra-chromosomal constructs. Vectors may also be amplified and multiple copies may exist or be integrated in the genome. In some embodiments, cells of the invention may contain 1, 2, 3, 4, 5, 6, 7, 8, 9, 10, 15, 20 or more copies of nucleic acids encoding a fusion therapeutic glycoprotein. In some embodiments, cells of the invention may contain multiple copies (e.g., 2, 3, 4, 5, 6, 7, 8, 9, 10, 15, 20 or more) of nucleic acids encoding one or more fusion therapeutic glycoproteins.

Mammalian Cell Lines

Any mammalian cell or cell type susceptible to cell culture, and to expression of polypeptides, may be utilized in accordance with the present invention as a host cell. Non-limiting examples of mammalian cells that may be used in accordance with the present invention include HT1080 cells (Rasheed S, Nelson-Rees W A, Toth E M, Arnstein P, Gardner M B. Characterization of a newly derived human sarcoma cell line (HT1080). Cancer 33:1027-1033, 1974), human embryonic kidney 293 cells (HEK293), HeLa cells; BALB/c mouse myeloma line (NSO/l, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells +/−DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In some embodiments, a suitable mammalian cell is not a endosomal acidification-deficient cell.

Additionally, any number of commercially and non-commercially available hybridoma cell lines that express polypeptides or proteins may be utilized in accordance with the present invention. One skilled in the art will appreciate that hybridoma cell lines might have different nutrition requirements and/or might require different culture conditions for optimal growth and polypeptide or protein expression, and will be able to modify conditions as needed.

Non-Mammalian Cell Lines

Any non-mammalian derived cell or cell type susceptible to cell culture, and to expression of polypeptides, may be utilized in accordance with the present invention as a host cell. Non-limiting examples of non-mammalian host cells and cell lines that may be used in accordance with the present invention include cells and cell lines derived from *Pichia pastoris, Pichia methanolica, Pichia angusta, Schizosacccharomyces pombe, Saccharomyces cerevisiae*, and *Yarrowia lipolytica* for yeast; *Sodoptera frugiperda, Trichoplusis ni, Drosophila melangoster* and *Manduca sexta* for insects; and *Escherichia coli, Salmonella typhimurium, Bacillus subtilis, Bacillus licheniformis, Bacteroides fragilis, Clostridia perfringens, Clostridia difficile* for bacteria; and *Xenopus Laevis* from amphibian.

In other embodiments, transgenic nonhuman mammals have been shown to produce therapeutic glycoproteins (e.g., lysosomal enzymes) in their milk. Such transgenic nonhuman mammals may include mice, rabbits, goats, sheep, porcines or bovines. See U.S. Pat. Nos. 6,118,045 and 7,351,410, each of which are hereby incorporated by reference in their entirety.

Any and all methods suitable for producing recombinant protein can be used to produce therapeutic protein of the present invention.

Pharmaceutical Compositions and Administration

The present invention further provides pharmaceutical compositions containing targeted therapeutics according to the present invention. Typically, suitable pharmaceutical compositions contain at least one pharmaceutically acceptable excipient and are formulated for administration to humans.

For example, pharmaceutical compositions provided herein may be provided in a sterile injectable form (e.g., a form that is suitable for subcutaneous, intravenous, or intrathecal injection). For example, in some embodiments, pharmaceutical compositions are provided in a liquid dosage form that is suitable for injection. In some embodiments, pharmaceutical compositions are provided as powders (e.g., lyophilized and/or sterilized), optionally under vacuum, which are reconstituted with an aqueous diluent (e.g., water, buffer, salt solution, etc.) prior to injection. In some embodiments, pharmaceutical compositions are diluted and/or reconstituted in water, sodium chloride solution, sodium acetate solution, benzyl alcohol solution, phosphate buffered saline, etc. In some embodiments, powder should be mixed gently with the aqueous diluent (e.g., not shaken).

In some embodiments, provided pharmaceutical compositions comprise one or more pharmaceutically acceptable excipients (e.g., preservative, inert diluent, dispersing agent, surface active agent and/or emulsifier, buffering agent, etc.). In some embodiments, pharmaceutical compositions comprise one or more preservatives. In some embodiments, pharmaceutical compositions comprise no preservative.

Compositions of the pharmaceutical compositions described herein may be prepared by any method known or hereafter developed in the art of pharmacology. In some embodiments, such preparatory methods include the step of bringing active ingredient into association with one or more excipients and/or one or more other accessory ingredients, and then, if necessary and/or desirable, shaping and/or packaging the product into a desired single- or multi-dose unit.

A pharmaceutical composition in accordance with the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to a dose which would be administered to a subject and/or a convenient fraction of such a dose such as, for example, one-half or one-third of such a dose.

Relative amounts of active ingredient, pharmaceutically acceptable excipient, and/or any additional ingredients in a pharmaceutical composition in accordance with the invention may vary, depending upon the identity, size, and/or condition of the subject treated and/or depending upon the route by which the composition is to be administered. By way of example, the composition may comprise between 0.1% and 100% (w/w) active ingredient.

Pharmaceutical compositions of the present invention may additionally comprise a pharmaceutically acceptable excipient, which, as used herein, may be or comprise solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

Targeted therapeutics described herein (or a composition or medicament containing a targeted therapeutics described herein) can be administered by any appropriate route generally known in the art. In some embodiments, a targeted therapeutic or a pharmaceutical composition containing the same is administered systemically. Systemic administration may be intravenous, intramuscular, intradermal, by inhalation, transdermal (topical), intraocular, subcutaneous, oral and/or transmucosal. In some embodiments, a targeted therapeutics or a pharmaceutical composition containing the same is administered by intramuscular injection. In some embodiments, a targeted therapeutics or a pharmaceutical composition containing the same is administered subcutaneously. Administration may be performed by injecting a composition into areas including, but not limited to, the thigh region, abdominal region, gluteal region, or scapular region. In some embodiments, a targeted therapeutics or a pharmaceutical composition containing the same is administered intravenously. In some embodiments, a targeted therapeutics or a pharmaceutical composition containing the same is administered orally. More than one route can be used concurrently, if desired. All of the administration routes disclosed herein are generally known in the art, and the skilled artisan would know how to administer targeted therapeutics of the present invention by these routes.

In some embodiments, pharmaceutical compositions according to the present invention can be used for CNS delivery via various techniques and routes including, but not limited to, intraparenchymal, intracerebral, intravetricular cerebral (ICV), intrathecal (e.g., IT-Lumbar, IT-cisterna magna) administrations and any other techniques and routes for injection directly or indirectly to the CNS and/or CSF.

In some embodiments, pharmaceutical compositions according to the present invention can be used for intrathecal administration. As used herein, intrathecal administration (also referred to as intrathecal injection or intrathecal delivery) refers to an injection into the spinal canal (intrathecal space surrounding the spinal cord). Various formulations for intrathecal administration are described in WO/2011/163652, the contents of which are incorporated herein by reference.

According to the present invention, a pharmaceutical composition containing a targeted therapeutics may be injected at any region surrounding the spinal canal. In some embodiments, a pharmaceutical composition containing a targeted therapeutics is injected into the lumbar area or the cisterna magna or intraventricularly into a cerebral ventricle space. As used herein, the term "lumbar region" or "lumbar area" refers to the area between the third and fourth lumbar (lower back) vertebrae and, more inclusively, the L2-S1 region of the spine. Typically, intrathecal injection via the lumbar region or lumbar area is also referred to as "lumbar IT delivery" or "lumbar IT administration."

Various devices may be used for intrathecal delivery according to the present invention. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. As a non-limiting example, a suitable securing mechanism contains one or more nobs mounted on the surface of the hollow body and a sutured ring adjustable over the one or more nobs to prevent the hollow body (e.g., catheter) from slipping out of the spinal cord. In various embodiments, the fluid access port comprises a reservoir. In some embodiments, the fluid access port comprises a mechanical pump (e.g., an infusion pump). In some embodiments, an implanted catheter is connected to either a reservoir (e.g., for bolus delivery), or an infusion pump. The fluid access port may be implanted or external In some embodiments, intrathecal administration may be performed by either lumbar puncture (i.e., slow bolus) or via a port-catheter delivery system (i.e., infusion or bolus). In some embodiments, the catheter is inserted between the laminae of the lumbar vertebrae and the tip is threaded up the thecal space to the desired level (generally L3-L4).

For injection, formulations of the invention can be formulated in liquid solutions. In addition, the enzyme may be formulated in solid form and re-dissolved or suspended immediately prior to use. Lyophilized forms are also included. The injection can be, for example, in the form of a bolus injection or continuous infusion (e.g., using infusion pumps) of the enzyme.

Treatment of Pompe Disease, San B and Other Lysosomal Storage Diseases

The present invention may be used to effectively treat Pompe Disease, Sanfilippo Syndrome Type B and other lysosomal storage diseases.

Pompe disease, or Glycogen Storage Disease Type II, is an autosomal recessive metabolic disorder resulting from a deficiency or dysfunction of the lysosomal hydrolase acid alpha-glucosidase (GAA). GAA is localized to lysosomes and plays an important role in the catabolism of glycogen into glucose. In the absence of the enzyme, these glycogen accumulates within the cells, ultimately causing engorgement, followed by cellular death and tissue destruction. Due the widespread expression of the enzyme, multiple cell types and organ systems are affected in Pompe patients.

Unlike San B, which displays CNS degeneration as the predominant defining clinical feature, Pompe disease is characterized by a degeneration within the peripheral tissues of the body. In particular, glycogen build-up results in progressive muscle weakness (myopathy) throughout the body, specifically affecting the tissues of the heart, skeletal muscles, as well as liver and kidneys. Typical findings are those of enlarged heart with non-specific conduction defects, along with several indicators of kidney disease, such as high levels of serum creatine kinase, aldolase, aspartate transaminase and lactic dehydrogenase. The disease typically manifests itself in the first several month of life, with cardiomegaly, hypotonia, cardiomyopathy, respiratory distress and muscle weakness. Some affected individuals experience a progressive loss of skeletal muscle, cardiac or kidney function, with most affected individuals dying of disease-associated complications in their first or second decade.

Sanfilippo Syndrome Type B (San B), or Mucopolysaccharidosis III B (MPS III B), is a heritable metabolic disorder resulting from a deficiency of the enzyme Naglu. Naglu is localized to lysosomes and plays an important role in the catabolism of glycosaminoglycans (GAGs) heparan- and dermatan-sulfate. In the absence of enzyme, these substrates accumulate within cells, ultimately causing engorgement, followed by cellular death and tissue destruction. Due to the widespread expression of Naglu, multiple cell types and organ systems are affected in MPS III B patients.

A defining clinical feature of San B is central nervous system (CNS) degeneration, however, which typically results in cognitive impairment (e.g., decrease in IQ). Additionally, MRI scans of affected individuals have revealed white matter lesions, dilated perivascular spaces in the brain parenchyma, ganglia, corpus callosum, and brainstem; atrophy; and ventriculomegaly (Wang et al. Molecular Genetics and Metabolism, 2009). The disease typically manifests itself in the first years of life with organomegaly and skeletal abnormalities. Some affected individuals experience a progressive loss of cognitive function, with most affected individuals dying of disease-associated complications in their first or second decade.

Compositions and methods of the present invention may be used to effectively treat individuals suffering from or susceptible to Pompe Disease or San B. The terms "treat" or "treatment," as used herein, refer to amelioration of one or more symptoms associated with the disease, prevention or delay of the onset of one or more symptoms of the disease, and/or lessening of the severity or frequency of one or more symptoms of the disease.

In some embodiments, treatment refers to partial or complete alleviation, amelioration, relief, inhibition, delay of onset, reduction of severity and/or incidence of impairment in a Pompe Disease or San B patient. As used herein, the term "impairment" includes various symptoms in various organ systems commonly associated with Pompe Disease and/or San B (e.g., in the brain and spinal cord or skeletal or heart muscle). Symptoms of neurological impairment may include, for example, e.g., cognitive impairment; white matter lesions; dilated perivascular spaces in the brain parenchyma, ganglia, corpus callosum, and/or brainstem; atrophy; and/or ventriculomegaly, among others. Symptoms often associated with Pompe Disease include, for example, weakness of skeletal muscle and heart failure and respiratory weakness.

The terms, "improve," "increase" or "reduce," as used herein, indicate values that are relative to a control. In some embodiments, a suitable control is a baseline measurement, such as a measurement in the same individual prior to initiation of the treatment described herein, or a measurement in a control individual (or multiple control individuals) in the absence of the treatment described herein. A "control individual" is an individual afflicted with a lysosomal storage disease (e.g., San B, Pompe Disease), who is about the same age and/or gender as the individual suffering from the same lysosmal storage disease, who is being treated (to ensure that the stages of the disease in the treated individual and the control individual(s) are comparable).

The individual (also referred to as "patient" or "subject") being treated is an individual (fetus, infant, child, adolescent, or adult human) having a lysosomal storage disease or having the potential to develop a lysosmal storage disease. In some embodiments, the lysosmal storage disease is Pompe Disease or Sanfilippo Syndrome. In some specific embodiments the lysosomal storage disease is San B. The individual can have residual endogenous GAA or Naglu expression and/or activity, or no measurable activity. For example, the individual having Pompe Disease may have GAA expression levels that are less than about 30-50%, less than about 25-30%, less than about 20-25%, less than about 15-20%, less than about 10-15%, less than about 5-10%, less than about 0.1-5% of normal GAA expression levels. For example, the individual having San B may have Naglu expression levels that are less than about 30-50%, less than about 25-30%, less than about 20-25%, less than about 15-20%, less than about 10-15%, less than about 5-10%, less than about 0.1-5% of normal Naglu expression levels.

In some embodiments, the individual is an individual who has been recently diagnosed with the disease. Typically, early treatment (treatment commencing as soon as possible after diagnosis) is important to minimize the effects of the disease and to maximize the benefits of treatment.

All references cited herein are incorporated herein by reference in their entirety.

The invention will be more fully understood by reference to the following examples. They should not, however, be construed as limiting the scope of the invention.

EXAMPLES

Example 1: Generation of Components for PCSK9 Fusion Proteins

The present invention provides, among other things, methods and compositions for lysosomal targeting of a therapeutic protein (e.g. a lysosmal enzyme) based on a lysosomal targeting moiety. The current example, discloses a general method for producing one or more targeted therapeutic proteins, by generating a translational fusion protein between a lysosmal enzyme and a lysosomal targeting moiety. It will be understood from the teachings within the specification, that in some embodiments, one or more auxiliary proteins may also be produced to form a protein complex with the lysosmal targeting moiety.

The lysosomal enzymes acid alpha-glucosidase (GAA) and N-acetylglucosaminidase (Naglu) were chosen as candidate proteins, since it has been demonstrated that deficiency of each individual protein plays a central role in the development of Pompe disease and Sanpfilippo Syndrome (Mucopolysaccharidosis III) Type B, respectively. However, it will be understood by one skilled in the art, that such an approach is broadly applicable in generating fusion therapeutics for conditions associated with any lysosomal storage disease. It is contemplated that suitable fusion therapeutics of the current invention facilitate cellular uptake and lysosomal targeting and have an enzyme activity substantially similar to the native enzyme.

A lysosomal targeting moiety may be associated with a suitable therapeutic enzyme (e.g., lysosomal enzyme) covalently or non-covalently. For example, a lysosomal targeting moiety may be chemically conjugated to a therapeutic enzyme. Alternatively, a lysosomal targeting moiety may be fused to a therapeutic enzyme as a fusion protein. In yet further embodiments, a lysosomal targeting moiety (lysosomal targeting moiety) may be coupled, and or bound, to an auxiliary protein, to form a protein complex. In this example, a series of two constructs was created, each designed to express GAA or Naglu, fused to PCSK9. While PCSK9 is used as the representative lysosomal targeting moiety, it will be understood by one skilled in the art, that any lysosomal targeting moiety such as, PC proteins, proteins with a CHRD domain, proteins capable of binding to low density lipoprotein receptor (LDLR), amyloid precursor-like protein 2 (APLP2), Dynamin, amyloid precursor protein (APP), autosomal recessive hypercholesterolemia (ARH) protein, or low density lipoprotein receptor-related protein 8 (Lrp8)) or fragment thereof, may be used. For the example, a construct was also generated, encoding an auxiliary protein capable of forming a protein complex with a lysosomal targeting moiety.

PCSK9-GAA

An exemplary PCSK9-GAA fusion protein comprising S386A and F379A point mutations was created by connecting a nucleid acid encoding PCSK9 comprising S386A and F379A point mutations to a nucleic acid encoding GAA via an intervening GlyGlyGly-encoding linker (SEQ ID NO:14). The amino acid sequence resulting from the translation of (SEQ ID NO:14) is shown below (SEQ ID NO:17).

(SEQ ID NO: 17)

MGTVSSRRSWWPLPLLLLLLLLLGPAGARASIPWNLERITPPRYRADEYQPPDGGSLVEV

YLLDTSIQSDHREIEGRVMVTDFENVPEEDGTRFHRQASKCDSHGTHLAGVVSGRDAGV

AKGASMRSLRVLNCQGKGTVSGTLIGLEFIRKSQLVQPVGPLVVLLPLAGGYSRVLNAA

CQRLARAGVVLVTAAGNFRDDACLYSPASAPEVITVGATNAQDQPVTLGTLGTNFGRCV

DLFAPGEDIIGASSDCSTCAVSQSGTAQAAAHVAGIAAMMLSAEPELTLAELRQRLIHFS

AKDVINEAWFPEDQRVLTPNLVAALPPSTHGAGWQLFCRTVWSAHSGPTRMATAVARCA

PDEELLSCSSFSRSGKRRGERMEAQGGKLVCRAHNAFGGEGVYAIARCCLLPQANCSVH

TAPPAEASMGTRVHCHQQGHVLTGCSSHWEVEDLGTHKPPVLRPRGQPNQCVGHREASI

HASCCHAPGLECKVKEHGIPAPQEQVTVACEEGWTLTGCSALPGTSHVLGAYAVDNTCV

VRSRDVSTTGSTSEGAVTAVAICCRSRHLAQASQELQGGG*AHPGRPRAVPTQCDVPPNSR*

*FDCAPDKAITQEQCEARGCCYIPAKQGLQGAQMGQPWCFFPPSYPSYKLENLSSSEMGY*

*TATLTRTTPTFFPKDILTLRLDVMMETENRLHFTIKDPANRRYEVPLETPHVHSRAPSPL*

*YSVEFSEEPFGVIVRRQLDGRVLLNTTVAPLFFADQFLQLSTSLPSQYITGLAEHLSPLML*

*STSWTRITLWNRDLAPTPGANLYGSHPFYLALEDGGSAHGVFLLNSNAMDVVLQPSPAL*

-continued

SWRSTGGILDVYIFLGPEPKSVVQQYLDVVGYPFMPPYWGLGFHLCRWGYSSTAITRQV

VENMTRAHFPLDVQWNDLDYMDSRRDFTFNKDGFRDFPAMVQELHQGGRRYMMIVD

PAISSSGPAGSYRPYDEGLRRGVFITNETGQPLIGKVWPGSTAFPDFTNPTALAWWEDMV

AEFHDQVPFDGMWIDMNEPSNFIRGSEDGCPNNELENPPYVPGVVGGTLQAATICASS

HQFLSTHYNLHNLYGLTEAIASHRALVKARGTRPFVISRSTFAGHGRYAGHWTGDVWSS

WEQLASSVPEILQFNLLGVPLVGADVCGFLGNTSEELCVRWTQLGAFYPFMRNHNSLL

SLPQEPYSFSEPAQQAMRKALTLRYALLPHLYTLFHQAHVAGETVARPLFLEFPKDSSTW

TVDHQLLWGEALLITPVLQAGKAEVTGYFPLGTWYDLQTVPVEALGSLPPPPAAPREPAI

HSEGQWVTLPAPLDTINVHLRAGYIIPLQGPGLTTTESRQQPMALAVALTKGGEARGELF

WDDGESLEVLERGAYTQVIFLARNNTIVNELVRVTSEGAGLQLQKVTVLGVATAPQQVL

SNGVPVSNFTYSPDTKVLDICVSLLMGEQFLVSWC (1) The amino acid sequence of PCSK9 signal peptide is underlined.
(2) The amino acid sequence of PCSK9 Mature Protein (except mutations F379A and S386A, which are underlined and bold) is not underlined, bold or in italics.
(3) The amino acid sequence of the GlyGlyGly linker is underlined.
(4) The amino acid sequence of Mature Form GAA Protein (aa70-952) is bold and in italics.

Naglu-PCSK9

An exemplary Naglu-PCSK9 fusion protein comprising S386A and F379A point mutations was created by connecting a nucleic acid encoding Naglu to a nucleic acid encoding PCSK9 comprising S386A and F379A point mutations via an intervening GlyGlyGly-encoding linker (SEQ ID NO:15). The amino acid sequence resulting from the translation of (SEQ ID NO:15) is shown below (SEQ ID NO:18).

(SEQ ID NO: 18)
MEAVAVAAAVGVLLLAGAGGAAGDEAREAAAVRALVARLLGPGPAADFSVSVERALAA

KPGLDTYSLGGGGAARVRVRGSTGVAAAAGLHRYLRDFCGCHVAWSGSQLRLPRPLPA

VPGELTEATPNRYRYYQNVCTQSYSFVWWDWARWEREIDWMALNGINLALAWSGQEA

IWQRVYLALGLTQAEINEFFTGPAFLAWGRMGNLHTWDGPLPPSWHIKQLYLQHRVLDQ

MRSFGMTPVLPAFAGHVPEAVTRVFPQVNVTKMGSWGHFNCSYSCSFLLAPEDPIFPIIGS

LFLRELIKEFGTDHIYGADTFNEMQPPSSEPSYLAAATTAVYEAMTAVDTEAVWLLQGW

LFQHQPQFWGPAQIRAVLGAVPRGRLLVLDLFAESQPVYTRTASFQGQPFIWCMLHNFGG

NHGLFGALEAVNGGPEAARLFPNSTMVGTGMAPEGISQNEVVYSLMAELGWRKDPVPD

LAAWVTSFAARRYGVSHPDAGAAWRLLLRSVYNCSGEACRGHNRSPLVRRPSLQMNTS

IWYNRSDVFEAWRLLLTSAPSLATSPAFRYDLLDLTRQAVQELVSLYYEEARSAYLSKELA

SLLRAGGVLAYELLPALDEVLASDSRFLLGSWLEQARAAAVSEAEADFYEQNSRYQLTL

WGPEGNILDYANKQLAGLVANYYTPRWRLFLEALVDSVAQGIPPQQHQFDKNVFQLEQ

AFVLSKQRYPSQPRGDTVDLAKKIFLKYYPRWVAGSWGGGSIPWNLERITPPRYRADEYQ

PPDGGSLVEVYLLDTSIQSDHREIEGRVMVTDFENVPEEDGTRFHRQASKCDSHGTHLAGVV

SGRDAGVAKGASMRSLRVLNCQGKGTVSGTLIGLEFIRKSQLVQPVGPLVVLLPLAGGYSRVL

NAACQRLARAGVVLVTAAGNFRDDACLYSPASAPEVITVGATNAQDQPVTLGTLGTNFGRCVD

LFAPGEDIIGASSDCSTCAVSQSGTAQAAAHVAGIAAMMLSAEPELTLAELRQRLIHFSAKDVIN

EAWFPEDQRVLTPNLVAALPPSTHGAGWQLFCRTVWSAHSGPTRMATAVARCAPDEELLSCSS

FSRSGKRRGERMEAQGGKLVCRAHNAFGGEGVYAIARCCLLPQANCSVHTAPPAEASMGTRV

HCHQQGHVLTGCSSHWEVEDLGTHKPPVLRPRGQPNQCVGHREASIHASCCHAPGLECKV

```
KEHGIPAPQEQVTVACEEGWTLTGCSALPGTSHVLGAYAVDNTCVVRSRDVSTTGSTSEGAVTA

VAICCRSRHLAQASQELQ
```

(1) The amino acid sequence of Naglu signal peptide is underlined.
(2) The amino acid sequence of Mature Form of Naglu is not underlined, bold or in italics.
(3) The amino acid sequence of the GlyGlyGly linker is underlined.
(4) The amino acid sequence of PCSK9 Mature Protein (except mutations F379A and S386A, which are underlined and bold as well) is in italics.

PCSK9-Propeptide (PPP)

To facilitate formation of a lysosmal targeting moiety protein complex, a suitable auxiliary protein was created by generating a nucleic acid encoding PCSK9 signal peptide and PCSK9 propeptide (SEQ ID NO:16). The amino acid sequence resulting from the translation of (SEQ ID NO:16) is shown below (SEQ ID NO:19).

```
                                           (SEQ ID NO: 19)
MGTVSSRRSWWPLPLLLLLLLLLGPAGARAQEDEDGDYEELVLALRSEED

GLAEAPEHGTTATFHRCAKDPWRLPGTYVVVLKEETHLSQSERTARRLQA

QAARRGYLTKILHVFHGLLPGFLVKMSGDLLELALKLPHVDYIEEDSSVF

AQ
```

The amino acid sequence of PCSK9 signal peptide is underlined.

Sig/Pro-PCSK9-GAA

An exemplary Sig/Pro-PCSK9-GAA fusion protein comprising S386A and F379A point mutations was created by connecting a nucleic acid encoding PCSK9 comprising S386A and F379A point mutations to a nucleic acid encoding GAA via an intervening GlyGlyGly-encoding linker. The amino acid sequence resulting from the translation of this DNA is shown below (SEQ ID NO:20).

```
MGTVSSRRSWWPLPLLLLLLLLLGPAGARAQEDEDGDYEELVLALRSEEDGLAEAPEHGT

TATFHRCAKDPWRLPGTYVVVLKEETHLSQSERTARRLQAQAARRGYLTKILHVFHGLLPGFL

VKMSGDLLELALKLPHVDYIEEDSSVFAQRRRRRSIPWNLERITPPRYRADEYQPPDGGSLV

EVYLLDTSIQSDHREIEGRVMVTDFENVPEEDGTRFHRQASKCDSHGTHLAGVVSGRDA

GVAKGASMRSLRVLNCQGKGTVSGTLIGLEFIRKSQLVQPVGPLVVLLPLAGGYSRVLN

AACQRLARAGVVLVTAAGNFRDDACLYSPASAPEVITVGATNAQDQPVTLGTLGTNFGR

CVDLFAPGEDIIGASSDCSTCAVSQSGTAQAAAHVAGIAAMMLSAEPELTLAELRQRLIH

FSAKDVINEAWFPEDQRVLTPNLVAALPPSTHGAGWQLFCRTVWSAHSGPTRMATAVAR

CAPDEELLSCSSFSRSGKRRGERMEAQGGKLVCRAHNAFGGEGVYAIARCCLLPQANCS

VHTAPPAEASMGTRVHCHQQGHVLTGCSSHWEVEDLGTHKPPVLRPRGQPNQCVGHRE

ASIHASCCHAPGLECKVKEHGIPAPQEQVTVACEEGWTLTGCSALPGTSHVLGAYAVDNT

CVVRSRDVSTTGSTSEGAVTAVAICCRSRHLAQASQELQGGGAHPGRPRAVPTQCDVPP

NSRFDCAPDKAITQEQCEARGCCYIPAKQGLQGAQMGQPWCFFPPSYPSYKLENLSSSE

MGYTATLTRTTPTFFPKDILTLRLDVMMETENRLHFTIKDPANRRYEVPLETPHVHSRA

PSPLYSVEFSEEPFGVIVRRQLDGRVLLNTTVAPLFFADQFLQLSTSLPSQYITGLAEHLS

PLMLSTSWTRITLWNRDLAPTPGANLYGSHPFYLALEDGGSAHGVFLLNSNAMDVVLQ

PSPALSWRSTGGILDVYIFLGPEPKSVVQQYLDVVGYPFMPPYWGLGFHLCRWGYSSTAI

TRQVVENMTRAHFPLDVQWNDLDYMDSRRDFTFNKDGFRDFPAMVQELHQGGRRYM

MIVDPAISSSGPAGSYRPYDEGLRRGVFITNETGQPLIGKVWPGSTAFPDFTNPTALAWW

EDMVAEFHDQVPFDGMWIDMNEPSNFIRGSEDGCPNNELENPPYVPGVVGGTLQAATI

CASSHQFLSTHYNLHNLYGLTEAIASHRALVKARGTRPFVISRSTFAGHGRYAGHWTGD

VWSSWEQLASSVPEILQFNLLGVPLVGADVCGFLGNTSEELCVRWTQLGAFYPFMRNH

NSLLSLPQEPYSFSEPAQQAMRKALTLRYALLPHLYTLFHQAHVAGETVARPLFLEFPKD

SSTWTVDHQLLWGEALLITPVLQAGKAEVTGYFPLGTWYDLQTVPVEALGSLPPPAAP
```

*REPAIHSEGQWVTLPAPLDTINVHLRAGYIIPLQGPGLTTTESRQQPMALAVALTKGGEA*

*RGELFWDDGESLEVLERGAYTQVIFLARNNTIVNELVRVTSEGAGLQLQKVTVLGVATA*

*PQQVLSNGVPVSNFTYSPDTKVLDICVSLLMGEQFLVSWC*

(1) The amino acid sequence of PCSK9 signal peptide is underlined.
(2) The amino acid sequence of PCSK9 propeptide is in italics.
(3) The amino acid sequence of a Furin proteolytic cleavage site is bolded and underlined.
(4) The amino acid sequence of PCSK9 Mature Protein (except mutations F379A and S386A, which are underlined and bold) is not underlined, bold or in italics.
(5) The amino acid sequence of the GlyGlyGly linker is underlined.
(6) The amino acid sequence of Mature Form GAA Protein (aa70-952) is bold and in italics.

Nucleic acids encoding a fusion protein and an auxiliary protein can be individually subcloned into mammalian expression vectors of choice. These expression constructs may then be transfected into a human cell line, and the cell line may be screened to generate over-expressing cell clones. To produce functional targeted therapeutics, a fusion protein is co-espressed with an auxiliary protein, for example PCSK9 propeptide, to ensure proper association between the two, which ensures endocytosis of the complex.

SEQ ID NO:17-19 are amino acid sequences which still contain the amino acids of PCSK9 or Naglu N-terminal signal peptides. These signal peptides are typically removed during intracellular processing and and are typically not present in the final targeted therapeutic drug product. Below are depitcted the amino acid sequences of targeted therapeutics resulting from, in order, expression of proteins defined by SEQ ID NO:17-19:

PCSK9-GAA (SEQ ID NO: 21)

SIPWNLERITPPRYRADEYQPPDGGSLVEVYLLDTSIQSDHREIEGRVMVTDFENVPEEDG

TRFHRQASKCDSHGTHLAGVVSGRDAGVAKGASMRSLRVLNCQGKGTVSGTLIGLEFIR

KSQLVQPVGPLVVLLPLAGGYSRVLNAACQRLARAGVVLVTAAGNFRDDACLYSPASAP

EVITVGATNAQDQPVTLGTLGTNFGRCVDLFAPGEDIIGASSDCSTCAVSQSGTAQAAAH

VAGIAAMMLSAEPELTLAELRQRLIHFSAKDVINEAWFPEDQRVLTPNLVAALPPSTHGA

GWQLFCRTVWSAHSGPTRMATAVARCAPDEELLSCSSFSRSGKRRGERMEAQGGKLVC

RAHNAFGGEGVYAIARCCLLPQANCSVHTAPPAEASMGTRVHCHQQGHVLTGCSSHWE

VEDLGTHKPPVLRPRGQPNQCVGHREASIHASCCHAPGLECKVKEHGIPAPQEQVTVAC

EEGWTLTGCSALPGTSHVLGAYAVDNTCVVRSRDVSTTGSTSEGAVTAVAICCRSRHLAQ

ASQELQGGG*AHPGRPRAVPTQCDVPPNSRFDCAPDKAITQEQCEARGCCYIPAKQGLQG*

*AQMGQPWCFFPPSYPSYKLENLSSSEMGYTATLTRTTPTFFPKDILTLRLDVMMETENR*

*LHFTIKDPANRRYEVPLETPHVHSRAPSPLYSVEFSEEPFGVIVRRQLDGRVLLNTTVAP*

*LFFADQFLQLSTSLPSQYITGLAEHLSPLMLSTSWTRITLWNRDLAPTPGANLYGSHPFY*

*LALEDGGSAHGVFLLNSNAMDVVLQPSPALSWRSTGGILDVYIFLGPEPKSVVQQYLDV*

*VGYPFMPPYWGLGFHLCRWGYSSTAITRQVVENMTRAHFPLDVQWNDLDYMDSRRDF*

*TFNKDGFRDFPAMVQELHQGGRRYMMIVDPAISSSGPAGSYRPYDEGLRRGVFITNETG*

*QPLIGKVWPGSTAFPDFTNPTALAWWEDMVAEFHDQVPFDGMWIDMNEPSNFIRGSE*

*DGCPNNELENPPYVPGVVGGTLQAATICASSHQFLSTHYNLHNLYGLTEAIASHRALVK*

*ARGTRPFVISRSTFAGHGRYAGHWTGDVWSSWEQLASSVPEILQFNLLGVPLVGADVCG*

*FLGNTSEELCVRWTQLGAFYPFMRNHNSLLSLPQEPYSFSEPAQQAMRKALTLRYALLP*

*HLYTLFHQAHVAGETVARPLFLEFPKDSSTWTVDHQLLWGEALLITPVLQAGKAEVTGY*

*FPLGTWYDLQTVPVEALGSLPPPPAAPREPAIHSEGQWVTLPAPLDTINVHLRAGYIIPLQ*

-continued

*GPGLTTTESRQQPMALAVALTKGGEARGELFWDDGESLEVLERGAYTQVIFLARNNTIV*

*NELVRVTSEGAGLQLQKVTVLGVATAPQQVLSNGVPVSNFTYSPDTKVLDICVSLLMGE*

*QFLVSWC*

(1) The amino acid sequence of PCSK9 Mature Protein (except mutations F379A and S386A, which are underlined and bold) is not underlined, bold or in italics.
(2) The amino acid sequence of the GlyGlyGly linker is underlined.
(3) The amino acid sequence of Mature Form GAA Protein (aa70-952) is bold and in italics.
Naglu-PCSK9

(SEQ ID NO: 22)
DEAREAAAVRALVARLLGPGPAADFSVSVERALAAKPGLDTYSLGGGGAARVRVRGST

GVAAAAGLHRYLRDFCGCHVAWSGSQLRLPRPLPAVPGELTEATPNRYRYYQNVCTQSY

SFVWWDWARWEREIDWMALNGINLALAWSGQEAIWQRVYLALGLTQAEINEFFTGPAF

LAWGRMGNLHTWDGPLPPSWHIKQLYLQHRVLDQMRSFGMTPVLPAFAGHVPEAVTRV

FPQVNVTKMGSWGHFNCSYSCSFLLAPEDPIFPIIGSLFLRELIKEFGTDHIYGADTFNEM

QPPSSEPSYLAAATTAVYEAMTAVDTEAVWLLQGWLFQHQPQFWGPAQIRAVLGAVPRG

RLLVLDLFAESQPVYTRTASFQGQPFIWCMLHNFGGNHGLFGALEAVNGGPEAARLFPN

STMVGTGMAPEGISQNEVVYSLMAELGWRKDPVPDLAAWVTSFAARRYGVSHPDAGA

AWRLLLRSVYNCSGEACRGHNRSPLVRRPSLQMNTSIWYNRSDVFEAWRLLLTSAPSLA

TSPAFRYDLLDLTRQAVQELVSLYYEEARSAYLSKELASLLRAGGVLAYELLPALDEVLA

SDSRFLLGSWLEQARAAAVSEAEADFYEQNSRYQLTLWGPEGNILDYANKQLAGLVANY

YTPRWRLFLEALVDSVAQGIPFQQHQFDKNVFQLEQAFVLSKQRYPSQPRGDTVDLAKK

IFLKYYPRWVAGSW<u>GGG</u>*SIPWNLERITPPRYRADEYQPPDGGSLVEVYLLDTSIQSDHREIEG*

*RVMVTDFENVPEEDGTRFHRQASKCDSHGTHLAGVVSGRDAGVAKGASMRSLRVLNCQGKG*

*TVSGTLIGLEFIRKSQLVQPVGPLVVLLPLAGGYSRVLNAACQRLARAGVVLVTAAGNFRDDAC*

*LYSPASAPEVITVGATNAQDQPVTLGTLGTNFGRCVDLFAPGEDIIGASSDCSTCAVSQSGTAQ*

*AAAHVAGIAAMMLSAEPELTLAELRQRLIHFSAKDVINEAWFPEDQRVLTPNLVAALPPSTHGA*

*GWQLFCRTVWSAHSGPTRMATAVARCAPDEELLSCSSFSRSGKRRGERMEAQGGKLVCRAHN*

*AFGGEGVYAIARCCLLPQANCSVHTAPPAEASMGTRVHCHQQGHVLTGCSSHWEVEDLGTH*

*KPPVLRPRGQPNQCVGHREASIHASCCHAPGLECKVKEHGIPAPQEQVTVACEEGWTLTGCS*

*ALPGTSHVLGAYAVDNTCVVRSRDVSTTGSTSEGAVTAVAICCRSRHLAQASQELQ*

(1) The amino acid sequence of Mature Form of Naglu is not underlined, bold or in italics.
(2) The amino acid sequence of the GlyGlyGly linker is underlined.
(3) The amino acid sequence of PCSK9 Mature Protein (except mutations F379A and S386A, which are underlined and bold as well) is in italics.

PCSK9-Propeptide (PPP)

(SEQ ID NO: 23)
QEDEDGDYEELVLALRSEEDGLAEAPEHGTTATFHRCAKDPWRLPGTYVV

VLKEETHLSQSERTARRLQAQAARRGYLTKILHVFHGLLPGFLVKMSGDL

LELALKLPHVDYIEEDSSVFAQ

SEQ ID NO:20 is an amino acid sequences which still contains the amino acids of the PCSK9 N-terminal signal peptide and propeptide. It is envisioned that the signal peptide is typically removed during intracellular processing and is typically not present in the final targeted therapeutic drug product. The Furin proteolytic cleavage site will be cleaved intracellularly and the fusion comprising PCSK9 and GAA will form a complex with the released propeptide.

For protein based assays and receptor binding experiments, recombinant protein may be produced in a wave bioreactor, using a mammalian cell culture expressing system. Following expression, protein/protein complexes may be purified using conventional protein purification methods.

Example 2: Activity Assay

Following purification, each fusion protein can be evaluated for proper function, by examining its specific activity and enzyme kinetics using a well-defined cleavable substrate. Based on this analysis, PSK9-GAA- and Naglu-PCSK9 binding constants and specificity for the enzyme substrate can be compared to each respective wildtype lysosomal enzyme, to ensure enzyme function is similar to the native protein.

Example 3: Fusion Protein Binding Studies

Studies will also be carried out to determine the binding properties of PCSK9-GAA and Naglu-PCSK9 fusion proteins, and evaluate their specificity for various cognate protein binding partners. For the approach, a surface plasmone resonance (SPR) assay will be employed using standard techniques.

There are four possible scenarios of carrying out this SPR assay. Firstly, the binding protein (such as, but not limited to this listed in Table 6 below) serving as "ligand" are diluted in immobilization buffer and bound to the dextran surface of a SPR sensor chip housed in a microfluidic system. A solution containing purified PCSK9-GAA or Naglu-PCSK9 protein, serving as the "analyte", is then injected into the device. Secondly, the PCSK9-GAA or Naglu-PCSK9 protein, serving as "ligand," are diluted in immobilization buffer and bound to the dextran surface of a SPR sensor chip housed in a microfluidic system. A solution containing the binding proteins (such as, but not limited to this listed in Table 6 below), serving as the "analyte," is then injected into the device. Thirdly, a "capturing molecule," such as an anti-PCSK9-GAA or anti-Naglu-PCSK9 antibody, is diluted in immobilization buffer and bound to the dextran surface of a SPR sensor chip housed in a microfluidic system. Next, a solution containing PCSK9-GAA or Naglu-PCSK9, serving as the "ligand," is injected into the microflow system and run over surface to bind the antibody to form a "capture complex." A solution containing binding protein, serving as the "analyte," is then injected into the device.

Fourthly, a "capturing molecule," such as anti-binding protein antibody, is diluted in immobilization buffer and bound to the dextran surface of a SPR sensor chip housed in a microfluidic system. Next, a solution containing recombinant "binding protein" (such as, but not limited to, those listed in Table 6 below), serving as the "ligand," is injected into the microflow system and run over surface to bind the antibody to form a "capture complex." A solution containing purified PCSK9-GAA or Naglu-PCSK9 protein, serving as the "analyte," is then injected into the device.

In all four scenarios, as the solution runs over the SPR sensor chip, the analyte binds to the ligand and/or capture complex, and an increase in SPR signal (expressed in response units, RU) is observed. After a predetermined period of time, a solution without the analyte is injected into the microfluidic device, resulting in dissociation of the interaction between analyte and ligand and/or capture complex, inn turn resulting in a decrease in SPR signal.

TABLE 6

Potential PCSK9 Secondary Binding Proteins

Low Density Lipoprotein Receptor (LDLR)
Amyloid Precursor-like Protein 2 (APLP2)
Dynamin
Amyloid Precursor Protein (APP)
Autosomal Recessive Hypercholesterolemia (ARH)

Proposed experimental conditions for use with the surface plasmone resonance (SPR) assay are described in Table 7 below.

TABLE 7

Experimental Design For Exemplary Surface Plasmone Resonance Assay (Scenario 4)

| Capturing Molecule | Ligand | Analyte | Analyte Conc. | Flow Rate | Association Time | Dissociation Time |
|---|---|---|---|---|---|---|
| anti-binding protein antibody | Protein from Table 6 | Naglu-PCSK9 | 0 nM | 30 µl/min | 300 sec | 300 sec |
| | | Naglu-PCSK9 | 0.625 nM | | | |
| | | Naglu-PCSK9 | 1.25 nM | | | |
| | | Naglu-PCSK9 | 2.5 nM | | | |
| | | Naglu-PCSK9 | 5 nM | | | |
| | | Naglu-PCSK9 | 10 nM | | | |
| | | Naglu-PCSK9 | 20 nM | | | |
| anti-binding protein antibody | Protein from Table 6 | PCSK9-GAA- | 0 nM | 30 µl/min | 300 sec | 300 sec |
| | | PCSK9-GAA | 0.625 nM | | | |
| | | PCSK9-GAA | 1.25 nM | | | |
| | | PCSK9-GAA | 2.5 nM | | | |
| | | PCSK9-GAA | 5 nM | | | |
| | | PCSK9-GAA | 10 nM | | | |
| | | PCSK9-GAA | 20 nM | | | |

To evaluate the overall specificity of each PCSK9 fusion protein, a competitive inhibition study may also be performed using a SPR assay. For the study, a purified protein comprising one or more human CHRD domains, referred to as an "inhibitor protein," can be used. Since it is suggested that PCSK9 binds to cognate proteins via it's CHRD domain, the protein can competitively inhibit binding between PCSK9 and the potential target binding partner. Alternatively, an antibody that binds to the PCSK9 binding site on the human LDLR, referred to as an "LDLR blocker", may also be used. Briefly, anti-binding protein antibody, the "capturing molecule," is diluted in immobilization buffer and bound to the dextran surface of a SPR sensor chip housed in a microfluidic system. Next, a solution containing recombinant protein (such as, but not limited to, amyloid precursor-like protein 2 (APLP2), Dynamin, amyloid precursor protein (APP), autosomal recessive hypercholesterolemia (ARH) protein, and low density lipoprotein receptor-related protein 8 (Lrp8)) or LDLR, serving as the "Ligand," is injected into the microflow system and run over the surface to bind the antibody to form a "capture complex." A solution containing purified Naglu-PCSK9 or PCSK9-GAA protein with or without 20 µM inhibitor protein is injected into the device and analyzed for binding. After a predetermined period of time, a solution without the analyte is injected into the microfluidic device, dissociating any possible interaction between the analyte and the capture complex, and resulting in a decrease in SPR signal. The experimental conditions used for the assay are described in Table 8 below.

TABLE 8

Experimental Design For Exemplary Surface Plasmone Resonance Assay

| Capturing Molecule | Ligand | Analyte | Analyte (Conc.) | Inhibitor (Conc.) | Flow Rate | Assoc. Time | Dissoc. Time |
|---|---|---|---|---|---|---|---|
| anti-binding protein antibody | protein from table 6 | Naglu-PCSK9 | 0.0 nM | 0.0 µM | 30 µl/min | 300 sec | 300 sec |
| | | Naglu-PCSK9 | 0.0 nM | 20 µM | | | |
| | | Naglu-PCSK9 | 0.625 nM | 20 µM | | | |
| | | Naglu-PCSK9 | 1.25 nM | 20 µM | | | |
| | | Naglu-PCSK9 | 2.5 nM | 20 µM | | | |
| | | Naglu-PCSK9 | 5 nM | 20 µM | | | |
| | | Naglu-PCSK9 | 10 nM | 20 µM | | | |
| | | Naglu-PCSK9 | 20 nM | 20 µM | | | |
| anti-binding protein antibody | protein from table 6 | PCSK9-GAA | 0.0 nM | 0.0 µM | 30 µl/min | 300 sec | 300 sec |
| | | PCSK9-GAA | 0.0 nM | 20 µM | | | |
| | | PCSK9-GAA | 0.625 nM | 20 µM | | | |
| | | PCSK9-GAA | 1.25 nM | 20 µM | | | |
| | | PCSK9-GAA | 2.5 nM | 20 µM | | | |
| | | PCSK9-GAA | 5 nM | 20 µM | | | |
| | | PCSK9-GAA | 10 nM | 20 µM | | | |
| | | PCSK9-GAA | 20 nM | 20 µM | | | |

The inverse study can also be performed to evaluate competitive inhibition of Naglu-PCSK9 and PCSK9-GAA by an inhibitor protein or LDLR blocker (an antibody that blocks PCSK9 binding to the LDLR), in which the concentration of each PCSK9 fusion protein is held constant and assayed against varying concentrations of inhibitor protein or LDLR blocker. Briefly, anti-binding protein antibody "capturing molecule" is diluted in immobilization buffer and bound on the dextran surface of a SPR sensor chip housed in a microfluidic system. Next, a solution containing recombinant protein, serving as the "ligand," is injected into the microflow system and run over surface to bind the antibody to form a "capture complex." A solution containing each purified PCSK9 fusion protein at 20 nM, along with 0-1.5 uM of inhibitor protein or LDLR blocker, is injected into the device and analyzed for binding. After a predetermined period of time, a solution without the analyte is injected into the microfluidic device, dissociating any possible interaction between the analyte and the capture complex, and resulting in a decrease in SPR signal. The experimental conditions for use in performing the assay are described in Table 9 below.

TABLE 9

Experimental Design For Exemplary Surface Plasmone Resonance Assay

| Capturing Molecule | Ligand | Analyte | Analyte (Conc.) | Inhibitor (Conc.) | Flow Rate | Assoc. Time | Dissoc. Time |
|---|---|---|---|---|---|---|---|
| anti-binding protein | protein from table 6 | Naglu-PCSK9 | 20 nM | 0.0 nM | 30 µl/min | 300 sec | 300 sec |
| | | Naglu-PCSK9 | 20 nM | 25 nM | | | |
| | | Naglu-PCSK9 | 20 nM | 50 nM | | | |
| | | Naglu-PCSK9 | 20 nM | 100 nM | | | |
| | | Naglu-PCSK9 | 20 nM | 200 nM | | | |
| | | Naglu-PCSK9 | 20 nM | 400 nM | | | |
| | | Naglu-PCSK9 | 20 nM | 600 nM | | | |
| | | Naglu-PCSK9 | 20 nM | 1.0 µM | | | |
| | | Naglu-PCSK9 | 20 nM | 1.5 µM | | | |
| anti-binding protein | protein from table 6 | PCSK9-GAA | 20 nM | 0.0 nM | 30 µl/min | 300 sec | 300 sec |
| | | PCSK9-GAA | 20 nM | 25 nM | | | |
| | | PCSK9-GAA | 20 nM | 50 nM | | | |
| | | PCSK9-GAA | 20 nM | 100 nM | | | |

TABLE 9-continued

Experimental Design For Exemplary Surface Plasmone Resonance Assay

| Capturing Molecule | Ligand | Analyte | Analyte (Conc.) | Inhibitor (Conc.) | Flow Rate | Assoc. Time | Dissoc. Time |
|---|---|---|---|---|---|---|---|
| | | PCSK9-GAA | 20 nM | 200 nM | | | |
| | | PCSK9-GAA | 20 nM | 400 nM | | | |
| | | PCSK9-GAA | 20 nM | 600 nM | | | |
| | | PCSK9-GAA | 20 nM | 1.0 µM | | | |
| | | PCSK9-GAA | 20 nM | 1.5 µM | | | |

Example 4: In Vitro Studies

Cellular Uptake Assays

Studies may also be performed to assess lysosomal targeting and cellular uptake of lysosomal targeted therapeutics, in accordance with the claimed invention. In this particular representative example, a lysosomal targeting assay is described that uses PCSK9-GAA and Naglu-PCSK9 fusion proteins. However, one skilled in the art will appreciate that Example 4 teaches a general assay method that may be used to evaluate any lysosomal targeted therapeutic in accordance with the teachings of the instant application. The cell line of choice for this assay is C2C12 cell, which is a mouse myoblast cell lines (Yaffe D. and Saxel O; Serial passaging and differentiation of myogenic cells isolated from dystrophic mouse muscle; Nature 270 (5639): 725-727 (1977)) that has been utilized by scientists estimating the cellular uptake of GAA into muscle cells. The C2C12 cells are grown to confluence and treated with a solution of recombinant Naglu-PCSK9 or PCSK9-GAA, which is complexed with recombinant PCSK9-Propeptide (PPP). After a specified period of time, supernatant is removed, cells washed repeatedly; and following lysis each sample is assayed for Naglu and/or GAA enzyme activity.

Visualization of Lysosomal Targeting and Entry of Naglu-PCSK9 and PCSK9-GAA

Studies may also be carried out to evaluate cellular lysosomal targeting and entry using fluorescent immunomicroscopy. For the study, C2C12 cell lines, as described above, are treated with or without recombinant Naglu-PCSK9 or PCSK9-GAA which has been complexed with PPP. Following treatment, the cells are fixed and prepared for staining. Both control and treated cells are stained using antibodies specific for each lysosomal protein (GAA or Naglu) along with Lamp-1, a lysosome specific protein biomarker. Cells are assayed for cellular internalization of each fusion protein by immunofluroescent microscopy.

We claim:

1. A targeted therapeutic fusion protein comprising a lysosomal enzyme fused to a lysosomal targeting moiety comprising a proprotein convertase subtilisin kexin type 9 (PCSK9) protein comprising amino acid substitutions S386A and F379A.

2. The targeted therapeutic fusion protein of claim 1, wherein the lysosomal enzyme is an acid alpha glucosidase (GAA) protein, comprising an amino acid sequence at least 80% identical to SEQ ID NO: 1.

3. The targeted therapeutic fusion protein of claim 1, wherein the lysosomal enzyme is an alpha-N-acetylglucosaminidase (Naglu) protein comprising an amino acid sequence at least 80% identical to SEQ ID NO: 4.

4. The targeted therapeutic fusion protein of claim 1, wherein the lysosomal targeting moiety and the lysosomal enzyme are fused via a linker.

5. The targeted therapeutic fusion protein of claim 4, wherein the linker comprises a sequence of GAPGGGGGAAAAAGGGGGGAPGGGGGAAAAAG-GGGGGAPG GGGGAAAAAGGGGGGAP, which is SEQ ID NO: 13.

* * * * *

SEQUENCE LISTING

```
<160> NUMBER OF SEQ ID NOS: 23

<210> SEQ ID NO 1
<211> LENGTH: 883
<212> TYPE: PRT
<213> ORGANISM: Homo sapiens

<400> SEQUENCE: 1

Ala His Pro Gly Arg Pro Arg Ala Val Pro Thr Gln Cys Asp Val Pro
1               5                  10                  15

Pro Asn Ser Arg Phe Asp Cys Ala Pro Asp Lys Ala Ile Thr Gln Glu
            20                  25                  30

Gln Cys Glu Ala Arg Gly Cys Cys Tyr Ile Pro Ala Lys Gln Gly Leu
        35                  40                  45

Gln Gly Ala Gln Met Gly Gln Pro Trp Cys Phe Phe Pro Pro Ser Tyr
    50                  55                  60

Pro Ser Tyr Lys Leu Glu Asn Leu Ser Ser Ser Glu Met Gly Tyr Thr
65                  70                  75                  80

Ala Thr Leu Thr Arg Thr Thr Pro Thr Phe Phe Pro Lys Asp Ile Leu
                85                  90                  95

Thr Leu Arg Leu Asp Val Met Met Glu Thr Glu Asn Arg Leu His Phe
            100                 105                 110

Thr Ile Lys Asp Pro Ala Asn Arg Arg Tyr Glu Val Pro Leu Glu Thr
        115                 120                 125

Pro His Val His Ser Arg Ala Pro Ser Pro Leu Tyr Ser Val Glu Phe
    130                 135                 140

Ser Glu Glu Pro Phe Gly Val Ile Val Arg Arg Gln Leu Asp Gly Arg
145                 150                 155                 160
```

-continued

Val Leu Leu Asn Thr Thr Val Ala Pro Leu Phe Phe Ala Asp Gln Phe
              165                 170                 175

Leu Gln Leu Ser Thr Ser Leu Pro Ser Gln Tyr Ile Thr Gly Leu Ala
              180                 185                 190

Glu His Leu Ser Pro Leu Met Leu Ser Thr Ser Trp Thr Arg Ile Thr
              195                 200                 205

Leu Trp Asn Arg Asp Leu Ala Pro Thr Pro Gly Ala Asn Leu Tyr Gly
    210                 215                 220

Ser His Pro Phe Tyr Leu Ala Leu Glu Asp Gly Ser Ala His Gly
225                 230                 235                 240

Val Phe Leu Leu Asn Ser Asn Ala Met Asp Val Val Leu Gln Pro Ser
              245                 250                 255

Pro Ala Leu Ser Trp Arg Ser Thr Gly Gly Ile Leu Asp Val Tyr Ile
              260                 265                 270

Phe Leu Gly Pro Glu Pro Lys Ser Val Val Gln Gln Tyr Leu Asp Val
          275                 280                 285

Val Gly Tyr Pro Phe Met Pro Pro Tyr Trp Gly Leu Gly Phe His Leu
      290                 295                 300

Cys Arg Trp Gly Tyr Ser Ser Thr Ala Ile Thr Arg Gln Val Val Glu
305                 310                 315                 320

Asn Met Thr Arg Ala His Phe Pro Leu Asp Val Gln Trp Asn Asp Leu
              325                 330                 335

Asp Tyr Met Asp Ser Arg Arg Asp Phe Thr Phe Asn Lys Asp Gly Phe
          340                 345                 350

Arg Asp Phe Pro Ala Met Val Gln Glu Leu His Gln Gly Gly Arg Arg
      355                 360                 365

Tyr Met Met Ile Val Asp Pro Ala Ile Ser Ser Ser Gly Pro Ala Gly
  370                 375                 380

Ser Tyr Arg Pro Tyr Asp Glu Gly Leu Arg Arg Gly Val Phe Ile Thr
385                 390                 395                 400

Asn Glu Thr Gly Gln Pro Leu Ile Gly Lys Val Trp Pro Gly Ser Thr
              405                 410                 415

Ala Phe Pro Asp Phe Thr Asn Pro Thr Ala Leu Ala Trp Trp Glu Asp
          420                 425                 430

Met Val Ala Glu Phe His Asp Gln Val Pro Phe Asp Gly Met Trp Ile
      435                 440                 445

Asp Met Asn Glu Pro Ser Asn Phe Ile Arg Gly Ser Glu Asp Gly Cys
  450                 455                 460

Pro Asn Asn Glu Leu Glu Asn Pro Pro Tyr Val Pro Gly Val Val Gly
465                 470                 475                 480

Gly Thr Leu Gln Ala Ala Thr Ile Cys Ala Ser Ser His Gln Phe Leu
              485                 490                 495

Ser Thr His Tyr Asn Leu His Asn Leu Tyr Gly Leu Thr Glu Ala Ile
          500                 505                 510

Ala Ser His Arg Ala Leu Val Lys Ala Arg Gly Thr Arg Pro Phe Val
      515                 520                 525

Ile Ser Arg Ser Thr Phe Ala Gly His Gly Arg Tyr Ala Gly His Trp
  530                 535                 540

Thr Gly Asp Val Trp Ser Ser Trp Glu Gln Leu Ala Ser Ser Val Pro
545                 550                 555                 560

Glu Ile Leu Gln Phe Asn Leu Leu Gly Val Pro Leu Val Gly Ala Asp
              565                 570                 575

-continued

Val Cys Gly Phe Leu Gly Asn Thr Ser Glu Glu Leu Cys Val Arg Trp
                580                 585                 590

Thr Gln Leu Gly Ala Phe Tyr Pro Phe Met Arg Asn His Asn Ser Leu
            595                 600                 605

Leu Ser Leu Pro Gln Glu Pro Tyr Ser Phe Ser Glu Pro Ala Gln Gln
        610                 615                 620

Ala Met Arg Lys Ala Leu Thr Leu Arg Tyr Ala Leu Leu Pro His Leu
625                 630                 635                 640

Tyr Thr Leu Phe His Gln Ala His Val Ala Gly Glu Thr Val Ala Arg
                645                 650                 655

Pro Leu Phe Leu Glu Phe Pro Lys Asp Ser Ser Thr Trp Thr Val Asp
            660                 665                 670

His Gln Leu Leu Trp Gly Glu Ala Leu Leu Ile Thr Pro Val Leu Gln
        675                 680                 685

Ala Gly Lys Ala Glu Val Thr Gly Tyr Phe Pro Leu Gly Thr Trp Tyr
690                 695                 700

Asp Leu Gln Thr Val Pro Val Glu Ala Leu Gly Ser Leu Pro Pro Pro
705                 710                 715                 720

Pro Ala Ala Pro Arg Glu Pro Ala Ile His Ser Glu Gly Gln Trp Val
                725                 730                 735

Thr Leu Pro Ala Pro Leu Asp Thr Ile Asn Val His Leu Arg Ala Gly
            740                 745                 750

Tyr Ile Ile Pro Leu Gln Gly Pro Gly Leu Thr Thr Thr Glu Ser Arg
        755                 760                 765

Gln Gln Pro Met Ala Leu Ala Val Ala Leu Thr Lys Gly Gly Glu Ala
770                 775                 780

Arg Gly Glu Leu Phe Trp Asp Asp Gly Glu Ser Leu Glu Val Leu Glu
785                 790                 795                 800

Arg Gly Ala Tyr Thr Gln Val Ile Phe Leu Ala Arg Asn Asn Thr Ile
                805                 810                 815

Val Asn Glu Leu Val Arg Val Thr Ser Glu Gly Ala Gly Leu Gln Leu
            820                 825                 830

Gln Lys Val Thr Val Leu Gly Val Ala Thr Ala Pro Gln Gln Val Leu
        835                 840                 845

Ser Asn Gly Val Pro Val Ser Asn Phe Thr Tyr Ser Pro Asp Thr Lys
850                 855                 860

Val Leu Asp Ile Cys Val Ser Leu Leu Met Gly Glu Gln Phe Leu Val
865                 870                 875                 880

Ser Trp Cys

<210> SEQ ID NO 2
<211> LENGTH: 925
<212> TYPE: PRT
<213> ORGANISM: Homo sapiens

<400> SEQUENCE: 2

Gly His Ile Leu Leu His Asp Phe Leu Leu Val Pro Arg Glu Leu Ser
1               5                   10                  15

Gly Ser Ser Pro Val Leu Glu Glu Thr His Pro Ala His Gln Gln Gly
            20                  25                  30

Ala Ser Arg Pro Gly Pro Arg Asp Ala Gln Ala His Pro Gly Arg Pro
        35                  40                  45

Arg Ala Val Pro Thr Gln Cys Asp Val Pro Pro Asn Ser Arg Phe Asp
50                  55                  60

```
Cys Ala Pro Asp Lys Ala Ile Thr Gln Glu Gln Cys Glu Ala Arg Gly
 65                  70                  75                  80
Cys Cys Tyr Ile Pro Ala Lys Gln Gly Leu Gln Gly Ala Gln Met Gly
                 85                  90                  95
Gln Pro Trp Cys Phe Phe Pro Ser Tyr Pro Ser Tyr Lys Leu Glu
            100                 105                 110
Asn Leu Ser Ser Ser Glu Met Gly Tyr Thr Ala Thr Leu Thr Arg Thr
             115                 120                 125
Thr Pro Thr Phe Phe Pro Lys Asp Ile Leu Thr Leu Arg Leu Asp Val
             130                 135                 140
Met Met Glu Thr Glu Asn Arg Leu His Phe Thr Ile Lys Asp Pro Ala
145                 150                 155                 160
Asn Arg Arg Tyr Glu Val Pro Leu Glu Thr Pro His Val His Ser Arg
                 165                 170                 175
Ala Pro Ser Pro Leu Tyr Ser Val Glu Phe Ser Glu Glu Pro Phe Gly
             180                 185                 190
Val Ile Val Arg Arg Gln Leu Asp Gly Arg Val Leu Leu Asn Thr Thr
             195                 200                 205
Val Ala Pro Leu Phe Phe Ala Asp Gln Phe Leu Gln Leu Ser Thr Ser
             210                 215                 220
Leu Pro Ser Gln Tyr Ile Thr Gly Leu Ala Glu His Leu Ser Pro Leu
225                 230                 235                 240
Met Leu Ser Thr Ser Trp Thr Arg Ile Thr Leu Trp Asn Arg Asp Leu
                 245                 250                 255
Ala Pro Thr Pro Gly Ala Asn Leu Tyr Gly Ser His Pro Phe Tyr Leu
             260                 265                 270
Ala Leu Glu Asp Gly Gly Ser Ala His Gly Val Phe Leu Leu Asn Ser
             275                 280                 285
Asn Ala Met Asp Val Val Leu Gln Pro Ser Pro Ala Leu Ser Trp Arg
             290                 295                 300
Ser Thr Gly Gly Ile Leu Asp Val Tyr Ile Phe Leu Gly Pro Glu Pro
305                 310                 315                 320
Lys Ser Val Val Gln Gln Tyr Leu Asp Val Val Gly Tyr Pro Phe Met
                 325                 330                 335
Pro Pro Tyr Trp Gly Leu Gly Phe His Leu Cys Arg Trp Gly Tyr Ser
             340                 345                 350
Ser Thr Ala Ile Thr Arg Gln Val Val Glu Asn Met Thr Arg Ala His
             355                 360                 365
Phe Pro Leu Asp Val Gln Trp Asn Asp Leu Asp Tyr Met Asp Ser Arg
             370                 375                 380
Arg Asp Phe Thr Phe Asn Lys Asp Gly Phe Arg Asp Phe Pro Ala Met
385                 390                 395                 400
Val Gln Glu Leu His Gln Gly Gly Arg Arg Tyr Met Met Ile Val Asp
                 405                 410                 415
Pro Ala Ile Ser Ser Ser Gly Pro Ala Gly Ser Tyr Arg Pro Tyr Asp
             420                 425                 430
Glu Gly Leu Arg Arg Gly Val Phe Ile Thr Asn Glu Thr Gly Gln Pro
             435                 440                 445
Leu Ile Gly Lys Val Trp Pro Gly Ser Thr Ala Phe Pro Asp Phe Thr
             450                 455                 460
Asn Pro Thr Ala Leu Ala Trp Trp Glu Asp Met Val Ala Glu Phe His
465                 470                 475                 480
Asp Gln Val Pro Phe Asp Gly Met Trp Ile Asp Met Asn Glu Pro Ser
```

```
                    485                 490                 495
Asn Phe Ile Arg Gly Ser Glu Asp Gly Cys Pro Asn Asn Glu Leu Glu
                500                 505                 510

Asn Pro Pro Tyr Val Pro Gly Val Gly Gly Thr Leu Gln Ala Ala
            515                 520                 525

Thr Ile Cys Ala Ser Ser His Gln Phe Leu Ser Thr His Tyr Asn Leu
        530                 535                 540

His Asn Leu Tyr Gly Leu Thr Glu Ala Ile Ala Ser His Arg Ala Leu
545                 550                 555                 560

Val Lys Ala Arg Gly Thr Arg Pro Phe Val Ile Ser Arg Ser Thr Phe
                565                 570                 575

Ala Gly His Gly Arg Tyr Ala Gly His Trp Thr Gly Asp Val Trp Ser
                580                 585                 590

Ser Trp Glu Gln Leu Ala Ser Ser Val Pro Glu Ile Leu Gln Phe Asn
            595                 600                 605

Leu Leu Gly Val Pro Leu Val Gly Ala Asp Val Cys Gly Phe Leu Gly
        610                 615                 620

Asn Thr Ser Glu Glu Leu Cys Val Arg Trp Thr Gln Leu Gly Ala Phe
625                 630                 635                 640

Tyr Pro Phe Met Arg Asn His Asn Ser Leu Leu Ser Leu Pro Gln Glu
                645                 650                 655

Pro Tyr Ser Phe Ser Glu Pro Ala Gln Gln Ala Met Arg Lys Ala Leu
            660                 665                 670

Thr Leu Arg Tyr Ala Leu Leu Pro His Leu Tyr Thr Leu Phe His Gln
        675                 680                 685

Ala His Val Ala Gly Glu Thr Val Ala Arg Pro Leu Phe Leu Glu Phe
690                 695                 700

Pro Lys Asp Ser Ser Thr Trp Thr Val Asp His Gln Leu Leu Trp Gly
705                 710                 715                 720

Glu Ala Leu Leu Ile Thr Pro Val Leu Gln Ala Gly Lys Ala Glu Val
                725                 730                 735

Thr Gly Tyr Phe Pro Leu Gly Thr Trp Tyr Asp Leu Gln Thr Val Pro
            740                 745                 750

Val Glu Ala Leu Gly Ser Leu Pro Pro Pro Ala Ala Pro Arg Glu
        755                 760                 765

Pro Ala Ile His Ser Glu Gly Gln Trp Val Thr Leu Pro Ala Pro Leu
770                 775                 780

Asp Thr Ile Asn Val His Leu Arg Ala Gly Tyr Ile Ile Pro Leu Gln
785                 790                 795                 800

Gly Pro Gly Leu Thr Thr Thr Glu Ser Arg Gln Gln Pro Met Ala Leu
                805                 810                 815

Ala Val Ala Leu Thr Lys Gly Gly Glu Ala Arg Gly Glu Leu Phe Trp
            820                 825                 830

Asp Asp Gly Glu Ser Leu Glu Val Leu Glu Arg Gly Ala Tyr Thr Gln
        835                 840                 845

Val Ile Phe Leu Ala Arg Asn Asn Thr Ile Val Asn Glu Leu Val Arg
850                 855                 860

Val Thr Ser Glu Gly Ala Gly Leu Gln Leu Gln Lys Val Thr Val Leu
865                 870                 875                 880

Gly Val Ala Thr Ala Pro Gln Gln Val Leu Ser Asn Gly Val Pro Val
                885                 890                 895

Ser Asn Phe Thr Tyr Ser Pro Asp Thr Lys Val Leu Asp Ile Cys Val
            900                 905                 910
```

Ser Leu Leu Met Gly Glu Gln Phe Leu Val Ser Trp Cys
        915                 920                 925

<210> SEQ ID NO 3
<211> LENGTH: 952
<212> TYPE: PRT
<213> ORGANISM: Homo sapiens

<400> SEQUENCE: 3

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro His Val His Ser Arg Ala Pro Ser Pro Leu
        195                 200                 205

Tyr Ser Val Glu Phe Ser Glu Glu Pro Phe Gly Val Ile Val Arg Arg
210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300

Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly

```
                355                 360                 365
Leu Gly Phe His Leu Cys Arg Trp Gly Tyr Ser Ser Thr Ala Ile Thr
370                 375                 380
Arg Gln Val Val Glu Asn Met Thr Arg Ala His Phe Pro Leu Asp Val
385                 390                 395                 400
Gln Trp Asn Asp Leu Asp Tyr Met Asp Ser Arg Arg Asp Phe Thr Phe
                405                 410                 415
Asn Lys Asp Gly Phe Arg Asp Phe Pro Ala Met Val Gln Glu Leu His
                420                 425                 430
Gln Gly Gly Arg Arg Tyr Met Met Ile Val Asp Pro Ala Ile Ser Ser
            435                 440                 445
Ser Gly Pro Ala Gly Ser Tyr Arg Pro Tyr Asp Glu Gly Leu Arg Arg
            450                 455                 460
Gly Val Phe Ile Thr Asn Glu Thr Gly Gln Pro Leu Ile Gly Lys Val
465                 470                 475                 480
Trp Pro Gly Ser Thr Ala Phe Pro Asp Phe Thr Asn Pro Thr Ala Leu
                485                 490                 495
Ala Trp Trp Glu Asp Met Val Ala Glu Phe His Asp Gln Val Pro Phe
                500                 505                 510
Asp Gly Met Trp Ile Asp Met Asn Glu Pro Ser Asn Phe Ile Arg Gly
            515                 520                 525
Ser Glu Asp Gly Cys Pro Asn Asn Glu Leu Glu Asn Pro Pro Tyr Val
            530                 535                 540
Pro Gly Val Val Gly Gly Thr Leu Gln Ala Ala Thr Ile Cys Ala Ser
545                 550                 555                 560
Ser His Gln Phe Leu Ser Thr His Tyr Asn Leu His Asn Leu Tyr Gly
                565                 570                 575
Leu Thr Glu Ala Ile Ala Ser His Arg Ala Leu Val Lys Ala Arg Gly
                580                 585                 590
Thr Arg Pro Phe Val Ile Ser Arg Ser Thr Phe Ala Gly His Gly Arg
            595                 600                 605
Tyr Ala Gly His Trp Thr Gly Asp Val Trp Ser Ser Trp Glu Gln Leu
            610                 615                 620
Ala Ser Ser Val Pro Glu Ile Leu Gln Phe Asn Leu Leu Gly Val Pro
625                 630                 635                 640
Leu Val Gly Ala Asp Val Cys Gly Phe Leu Gly Asn Thr Ser Glu Glu
                645                 650                 655
Leu Cys Val Arg Trp Thr Gln Leu Gly Ala Phe Tyr Pro Phe Met Arg
                660                 665                 670
Asn His Asn Ser Leu Leu Ser Leu Pro Gln Glu Pro Tyr Ser Phe Ser
            675                 680                 685
Glu Pro Ala Gln Gln Ala Met Arg Lys Ala Leu Thr Leu Arg Tyr Ala
            690                 695                 700
Leu Leu Pro His Leu Tyr Thr Leu Phe His Gln Ala His Val Ala Gly
705                 710                 715                 720
Glu Thr Val Ala Arg Pro Leu Phe Leu Glu Phe Pro Lys Asp Ser Ser
                725                 730                 735
Thr Trp Thr Val Asp His Gln Leu Leu Trp Gly Glu Ala Leu Leu Ile
                740                 745                 750
Thr Pro Val Leu Gln Ala Gly Lys Ala Glu Val Thr Gly Tyr Phe Pro
            755                 760                 765
Leu Gly Thr Trp Tyr Asp Leu Gln Thr Val Pro Val Glu Ala Leu Gly
            770                 775                 780
```

-continued

Ser Leu Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
            805                 810                 815

His Leu Arg Ala Gly Tyr Ile Ile Pro Leu Gln Gly Pro Gly Leu Thr
        820                 825                 830

Thr Thr Glu Ser Arg Gln Gln Pro Met Ala Leu Ala Val Ala Leu Thr
    835                 840                 845

Lys Gly Gly Glu Ala Arg Gly Glu Leu Phe Trp Asp Asp Gly Glu Ser
850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950

<210> SEQ ID NO 4
<211> LENGTH: 720
<212> TYPE: PRT
<213> ORGANISM: Homo sapiens

<400> SEQUENCE: 4

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65                  70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145                 150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp

```
                      195                 200                 205
        Gln Met Arg Ser Phe Gly Met Thr Pro Val Leu Pro Ala Phe Ala Gly
        210                 215                 220

His Val Pro Glu Ala Val Thr Arg Val Phe Pro Gln Val Asn Val Thr
    225                 230                 235                 240

Lys Met Gly Ser Trp Gly His Phe Asn Cys Ser Tyr Ser Cys Ser Phe
                        245                 250                 255

Leu Leu Ala Pro Glu Asp Pro Ile Phe Pro Ile Ile Gly Ser Leu Phe
                    260                 265                 270

Leu Arg Glu Leu Ile Lys Glu Phe Gly Thr Asp His Ile Tyr Gly Ala
                275                 280                 285

Asp Thr Phe Asn Glu Met Gln Pro Pro Ser Ser Glu Pro Ser Tyr Leu
        290                 295                 300

Ala Ala Ala Thr Thr Ala Val Tyr Glu Ala Met Thr Ala Val Asp Thr
    305                 310                 315                 320

Glu Ala Val Trp Leu Leu Gln Gly Trp Leu Phe Gln His Gln Pro Gln
                        325                 330                 335

Phe Trp Gly Pro Ala Gln Ile Arg Ala Val Leu Gly Ala Val Pro Arg
                    340                 345                 350

Gly Arg Leu Leu Val Leu Asp Leu Phe Ala Glu Ser Gln Pro Val Tyr
                355                 360                 365

Thr Arg Thr Ala Ser Phe Gln Gly Gln Pro Phe Ile Trp Cys Met Leu
        370                 375                 380

His Asn Phe Gly Gly Asn His Gly Leu Phe Gly Ala Leu Glu Ala Val
    385                 390                 395                 400

Asn Gly Gly Pro Glu Ala Ala Arg Leu Phe Pro Asn Ser Thr Met Val
                        405                 410                 415

Gly Thr Gly Met Ala Pro Glu Gly Ile Ser Gln Asn Glu Val Val Tyr
                    420                 425                 430

Ser Leu Met Ala Glu Leu Gly Trp Arg Lys Asp Pro Val Pro Asp Leu
                435                 440                 445

Ala Ala Trp Val Thr Ser Phe Ala Ala Arg Arg Tyr Gly Val Ser His
        450                 455                 460

Pro Asp Ala Gly Ala Ala Trp Arg Leu Leu Arg Ser Val Tyr Asn
    465                 470                 475                 480

Cys Ser Gly Glu Ala Cys Arg Gly His Asn Arg Ser Pro Leu Val Arg
                        485                 490                 495

Arg Pro Ser Leu Gln Met Asn Thr Ser Ile Trp Tyr Asn Arg Ser Asp
                    500                 505                 510

Val Phe Glu Ala Trp Arg Leu Leu Thr Ser Ala Pro Ser Leu Ala
                515                 520                 525

Thr Ser Pro Ala Phe Arg Tyr Asp Leu Leu Asp Thr Arg Gln Ala
        530                 535                 540

Val Gln Glu Leu Val Ser Leu Tyr Tyr Glu Glu Ala Arg Ser Ala Tyr
    545                 550                 555                 560

Leu Ser Lys Glu Leu Ala Ser Leu Leu Arg Ala Gly Gly Val Leu Ala
                        565                 570                 575

Tyr Glu Leu Leu Pro Ala Leu Asp Glu Val Leu Ala Ser Asp Ser Arg
                    580                 585                 590

Phe Leu Leu Gly Ser Trp Leu Glu Gln Ala Arg Ala Ala Ala Val Ser
                595                 600                 605

Glu Ala Glu Ala Asp Phe Tyr Glu Gln Asn Ser Arg Tyr Gln Leu Thr
        610                 615                 620
```

```
Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
            660                 665                 670

Gln Phe Asp Lys Asn Val Phe Gln Leu Glu Gln Ala Phe Val Leu Ser
        675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

<210> SEQ ID NO 5
<211> LENGTH: 743
<212> TYPE: PRT
<213> ORGANISM: Homo sapiens

<400> SEQUENCE: 5

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
        50                  55                  60

Tyr Ser Leu Gly Gly Gly Ala Ala Arg Val Arg Val Arg Gly Ser
65                  70                  75                  80

Thr Gly Val Ala Ala Ala Gly Leu His Arg Tyr Leu Arg Asp Phe
                85                  90                  95

Cys Gly Cys His Val Ala Trp Ser Gly Ser Gln Leu Arg Leu Pro Arg
            100                 105                 110

Pro Leu Pro Ala Val Pro Gly Glu Leu Thr Glu Ala Thr Pro Asn Arg
        115                 120                 125

Tyr Arg Tyr Tyr Gln Asn Val Cys Thr Gln Ser Tyr Ser Phe Val Trp
    130                 135                 140

Trp Asp Trp Ala Arg Trp Glu Arg Glu Ile Asp Trp Met Ala Leu Asn
145                 150                 155                 160

Gly Ile Asn Leu Ala Leu Ala Trp Ser Gly Gln Glu Ala Ile Trp Gln
                165                 170                 175

Arg Val Tyr Leu Ala Leu Gly Leu Thr Gln Ala Glu Ile Asn Glu Phe
            180                 185                 190

Phe Thr Gly Pro Ala Phe Leu Ala Trp Gly Arg Met Gly Asn Leu His
        195                 200                 205

Thr Trp Asp Gly Pro Leu Pro Pro Ser Trp His Ile Lys Gln Leu Tyr
    210                 215                 220

Leu Gln His Arg Val Leu Asp Gln Met Arg Ser Phe Gly Met Thr Pro
225                 230                 235                 240

Val Leu Pro Ala Phe Ala Gly His Val Pro Glu Ala Val Thr Arg Val
                245                 250                 255

Phe Pro Gln Val Asn Val Thr Lys Met Gly Ser Trp Gly His Phe Asn
            260                 265                 270

Cys Ser Tyr Ser Cys Ser Phe Leu Leu Ala Pro Glu Asp Pro Ile Phe
```

```
            275                 280                 285
Pro Ile Ile Gly Ser Leu Phe Leu Arg Glu Leu Ile Lys Glu Phe Gly
290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
            355                 360                 365
Val Leu Gly Ala Val Pro Arg Gly Arg Leu Leu Val Leu Asp Leu Phe
370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
            435                 440                 445
Ser Gln Asn Glu Val Val Tyr Ser Leu Met Ala Glu Leu Gly Trp Arg
450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
Leu Leu Arg Ser Val Tyr Asn Cys Ser Gly Glu Ala Cys Arg Gly His
            500                 505                 510
Asn Arg Ser Pro Leu Val Arg Arg Pro Ser Leu Gln Met Asn Thr Ser
            515                 520                 525
Ile Trp Tyr Asn Arg Ser Asp Val Phe Glu Ala Trp Arg Leu Leu Leu
            530                 535                 540
Thr Ser Ala Pro Ser Leu Ala Thr Ser Pro Ala Phe Arg Tyr Asp Leu
545                 550                 555                 560
Leu Asp Leu Thr Arg Gln Ala Val Gln Glu Leu Val Ser Leu Tyr Tyr
                565                 570                 575
Glu Glu Ala Arg Ser Ala Tyr Leu Ser Lys Glu Leu Ala Ser Leu Leu
            580                 585                 590
Arg Ala Gly Gly Val Leu Ala Tyr Glu Leu Leu Pro Ala Leu Asp Glu
            595                 600                 605
Val Leu Ala Ser Asp Ser Arg Phe Leu Leu Gly Ser Trp Leu Glu Gln
            610                 615                 620
Ala Arg Ala Ala Ala Val Ser Glu Ala Glu Ala Asp Phe Tyr Glu Gln
625                 630                 635                 640
Asn Ser Arg Tyr Gln Leu Thr Leu Trp Gly Pro Glu Gly Asn Ile Leu
                645                 650                 655
Asp Tyr Ala Asn Lys Gln Leu Ala Gly Leu Val Ala Asn Tyr Tyr Thr
            660                 665                 670
Pro Arg Trp Arg Leu Phe Leu Glu Ala Leu Val Asp Ser Val Ala Gln
            675                 680                 685
Gly Ile Pro Phe Gln Gln His Gln Phe Asp Lys Asn Val Phe Gln Leu
            690                 695                 700
```

```
Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp
            740

<210> SEQ ID NO 6
<211> LENGTH: 692
<212> TYPE: PRT
<213> ORGANISM: Homo sapiens

<400> SEQUENCE: 6

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
                20                  25                  30

Asp Glu Asp Gly Asp Tyr Glu Glu Leu Val Leu Ala Leu Arg Ser Glu
            35                  40                  45

Glu Asp Gly Leu Ala Glu Ala Pro Glu His Gly Thr Thr Ala Thr Phe
50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
```

```
                      325                 330                 335
        Gly Ala Thr Asn Ala Gln Asp Gln Pro Val Thr Leu Gly Thr Leu Gly
                        340                 345                 350

Thr Asn Phe Gly Arg Cys Val Asp Leu Phe Ala Pro Gly Glu Asp Ile
                        355                 360                 365

Ile Gly Ala Ser Ser Asp Cys Ser Thr Cys Phe Val Ser Gln Ser Gly
                        370                 375                 380

Thr Ser Gln Ala Ala His Val Ala Gly Ile Ala Ala Met Met Leu
        385                 390                 395                 400

Ser Ala Glu Pro Glu Leu Thr Leu Ala Glu Leu Arg Gln Arg Leu Ile
                        405                 410                 415

His Phe Ser Ala Lys Asp Val Ile Asn Glu Ala Trp Phe Pro Glu Asp
                        420                 425                 430

Gln Arg Val Leu Thr Pro Asn Leu Val Ala Ala Leu Pro Pro Ser Thr
                        435                 440                 445

His Gly Ala Gly Trp Gln Leu Phe Cys Arg Thr Val Trp Ser Ala His
                        450                 455                 460

Ser Gly Pro Thr Arg Met Ala Thr Ala Val Ala Arg Cys Ala Pro Asp
        465                 470                 475                 480

Glu Leu Leu Ser Cys Ser Ser Phe Ser Arg Ser Gly Lys Arg Arg
                        485                 490                 495

Gly Glu Arg Met Glu Ala Gln Gly Gly Lys Leu Val Cys Arg Ala His
                        500                 505                 510

Asn Ala Phe Gly Gly Glu Gly Val Tyr Ala Ile Ala Arg Cys Cys Leu
                        515                 520                 525

Leu Pro Gln Ala Asn Cys Ser Val His Thr Ala Pro Pro Ala Glu Ala
        530                 535                 540

Ser Met Gly Thr Arg Val His Cys His Gln Gly His Val Leu Thr
        545                 550                 555                 560

Gly Cys Ser Ser His Trp Glu Val Glu Asp Leu Gly Thr His Lys Pro
                        565                 570                 575

Pro Val Leu Arg Pro Arg Gly Gln Pro Asn Gln Cys Val Gly His Arg
                        580                 585                 590

Glu Ala Ser Ile His Ala Ser Cys His Ala Pro Gly Leu Glu Cys
                        595                 600                 605

Lys Val Lys Glu His Gly Ile Pro Ala Pro Gln Glu Gln Val Thr Val
        610                 615                 620

Ala Cys Glu Glu Gly Trp Thr Leu Thr Gly Cys Ser Ala Leu Pro Gly
        625                 630                 635                 640

Thr Ser His Val Leu Gly Ala Tyr Ala Val Asp Asn Thr Cys Val Val
                        645                 650                 655

Arg Ser Arg Asp Val Ser Thr Thr Gly Ser Thr Ser Glu Gly Ala Val
                        660                 665                 670

Thr Ala Val Ala Ile Cys Cys Arg Ser Arg His Leu Ala Gln Ala Ser
                        675                 680                 685

Gln Glu Leu Gln
                690

<210> SEQ ID NO 7
<211> LENGTH: 540
<212> TYPE: PRT
<213> ORGANISM: Homo sapiens

<400> SEQUENCE: 7
```

```
Ser Ile Pro Trp Asn Leu Glu Arg Ile Thr Pro Pro Arg Tyr Arg Ala
  1               5                  10                  15
Asp Glu Tyr Gln Pro Pro Asp Gly Gly Ser Leu Val Glu Val Tyr Leu
             20                  25                  30
Leu Asp Thr Ser Ile Gln Ser Asp His Arg Glu Ile Glu Gly Arg Val
             35                  40                  45
Met Val Thr Asp Phe Glu Asn Val Pro Glu Glu Asp Gly Thr Arg Phe
 50                  55                  60
His Arg Gln Ala Ser Lys Cys Asp Ser His Thr His Leu Ala Gly
 65                  70                  75                  80
Val Val Ser Gly Arg Asp Ala Gly Val Ala Lys Gly Ala Ser Met Arg
                 85                  90                  95
Ser Leu Arg Val Leu Asn Cys Gln Gly Lys Gly Thr Val Ser Gly Thr
                100                 105                 110
Leu Ile Gly Leu Glu Phe Ile Arg Lys Ser Gln Leu Val Gln Pro Val
            115                 120                 125
Gly Pro Leu Val Val Leu Leu Pro Leu Ala Gly Gly Tyr Ser Arg Val
        130                 135                 140
Leu Asn Ala Ala Cys Gln Arg Leu Ala Arg Ala Gly Val Val Leu Val
145                 150                 155                 160
Thr Ala Ala Gly Asn Phe Arg Asp Asp Ala Cys Leu Tyr Ser Pro Ala
                165                 170                 175
Ser Ala Pro Glu Val Ile Thr Val Gly Ala Thr Asn Ala Gln Asp Gln
            180                 185                 190
Pro Val Thr Leu Gly Thr Leu Gly Thr Asn Phe Gly Arg Cys Val Asp
        195                 200                 205
Leu Phe Ala Pro Gly Glu Asp Ile Ile Gly Ala Ser Ser Asp Cys Ser
210                 215                 220
Thr Cys Phe Val Ser Gln Ser Gly Thr Ser Gln Ala Ala Ala His Val
225                 230                 235                 240
Ala Gly Ile Ala Ala Met Met Leu Ser Ala Glu Pro Glu Leu Thr Leu
                245                 250                 255
Ala Glu Leu Arg Gln Arg Leu Ile His Phe Ser Ala Lys Asp Val Ile
            260                 265                 270
Asn Glu Ala Trp Phe Pro Glu Asp Gln Arg Val Leu Thr Pro Asn Leu
        275                 280                 285
Val Ala Ala Leu Pro Pro Ser Thr His Gly Ala Gly Trp Gln Leu Phe
    290                 295                 300
Cys Arg Thr Val Trp Ser Ala His Ser Gly Pro Thr Arg Met Ala Thr
305                 310                 315                 320
Ala Val Ala Arg Cys Ala Pro Asp Glu Glu Leu Leu Ser Cys Ser Ser
                325                 330                 335
Phe Ser Arg Ser Gly Lys Arg Gly Glu Arg Met Glu Ala Gln Gly
            340                 345                 350
Gly Lys Leu Val Cys Arg Ala His Asn Ala Phe Gly Gly Glu Gly Val
        355                 360                 365
Tyr Ala Ile Ala Arg Cys Cys Leu Leu Pro Gln Ala Asn Cys Ser Val
    370                 375                 380
His Thr Ala Pro Pro Ala Glu Ala Ser Met Gly Thr Arg Val His Cys
385                 390                 395                 400
His Gln Gln Gly His Val Leu Thr Gly Cys Ser Ser His Trp Glu Val
                405                 410                 415
Glu Asp Leu Gly Thr His Lys Pro Pro Val Leu Arg Pro Arg Gly Gln
```

```
                420             425             430

Pro Asn Gln Cys Val Gly His Arg Glu Ala Ser Ile His Ala Ser Cys
        435                 440                 445

Cys His Ala Pro Gly Leu Glu Cys Lys Val Lys Glu His Gly Ile Pro
    450                 455                 460

Ala Pro Gln Glu Gln Val Thr Val Ala Cys Glu Gly Trp Thr Leu
465                 470                 475                 480

Thr Gly Cys Ser Ala Leu Pro Gly Thr Ser His Val Leu Gly Ala Tyr
            485                 490                 495

Ala Val Asp Asn Thr Cys Val Val Arg Ser Arg Asp Val Ser Thr Thr
                500                 505                 510

Gly Ser Thr Ser Glu Gly Ala Val Thr Ala Val Ala Ile Cys Cys Arg
            515                 520                 525

Ser Arg His Leu Ala Gln Ala Ser Gln Glu Leu Gln
        530                 535                 540

<210> SEQ ID NO 8
<211> LENGTH: 122
<212> TYPE: PRT
<213> ORGANISM: Homo sapiens

<400> SEQUENCE: 8

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln
        115                 120

<210> SEQ ID NO 9
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Gly Gly Gly Gly Ala Ala Ala Ala Ala Gly Gly Gly Gly Gly
1               5                   10                  15

<210> SEQ ID NO 10
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 10

Gly Ala Pro
1

<210> SEQ ID NO 11
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Gly Gly Gly Gly Gly Pro
1               5

<210> SEQ ID NO 12
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 12

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro
        35

<210> SEQ ID NO 13
<211> LENGTH: 57
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 13

Gly Ala Pro Gly Gly Gly Gly Ala Ala Ala Ala Gly Gly Gly
1               5                   10                  15

Gly Gly Gly Ala Pro Gly Gly Gly Gly Ala Ala Ala Ala Gly
            20                  25                  30

Gly Gly Gly Gly Gly Ala Pro Gly Gly Gly Gly Ala Ala Ala Ala
        35                  40                  45

Ala Gly Gly Gly Gly Gly Gly Ala Pro
    50                  55

<210> SEQ ID NO 14
<211> LENGTH: 4371
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 14
atgggcaccg tcagctccag gcggtcctgg tggccgctgc cactgctgct gctgctgctg    60

```
ctgctcctgg gtcccgcggg cgcccgtgcg agcatcccgt ggaacctgga gcggattacc    120
cctccacggt accgggcgga tgaataccag cccccccgacg gaggcagcct ggtggaggtg   180
tatctcctag acaccagcat acagagtgac caccgggaaa tcgagggcag ggtcatggtc    240
accgacttcg agaatgtgcc cgaggaggac gggacccgct tccacagaca ggccagcaag    300
tgtgacagtc atggcaccca cctggcaggg gtggtcagcg gccgggatgc cggcgtggcc    360
aagggtgcca gcatgcgcag cctgcgcgtg ctcaactgcc aagggaaggg cacgcttagc    420
ggcaccctca taggcctgga gtttattcgg aaaagccagc tggtccagcc tgtggggcca    480
ctggtggtgc tgctgcccct ggcggtgggg tacagccgcg tcctcaacgc cgcctgccag    540
cgcctggcga gggctggggt cgtgctggtc accgctgccg gcaacttccg ggacgatgcc    600
tgcctctact ccccagcctc agctcccgag gtcatcacag ttggggccac caatgcccaa    660
gaccagccgg tgaccctggg gactttgggg accaactttg gccgctgtgt ggacctcttt    720
gccccagggg aggacatcat tggtgcctcc agcgactgca gcacctgcgc tgtgtcacag    780
agtgggacag cacaggctgc tgcccacgtg gctggcattg cagccatgat gctgtctgcc    840
gagccggagc tcaccctggc cgagttgagg cagagactga tccacttctc tgccaaagat    900
gtcatcaatg aggcctggtt ccctgaggac cagcgggtac tgacccccaa cctggtggcc    960
gccctgcccc ccagcaccca tggggcaggt tggcagctgt tttgcaggac tgtatggtca   1020
gcacactcgg ggcctacacg gatggccaca gccgtcgccc gctgcgcccc agatgaggag   1080
ctgctgagct gctccagttt ctccaggagt gggaagcggc ggggcgagcg catggaggcc   1140 caaggggca agctggtctg ccgggcccac aacgcttttg ggggtgaggg tgtctacgcc   1200
attgccaggt gctgcctgct accccaggcc aactgcagcg tccacacagc tccaccagct    1260
gaggccagca tggggacccg tgtccactgc caccaacagg gccacgtcct cacaggctgc    1320
agctcccact gggaggtgga ggaccttggc cccacaagc cgcctgtgct gaggccacga    1380
ggtcagccca ccagtgcgt gggccacagg gaggccagca tccacgcttc ctgctgccat    1440
gccccaggtc tggaatgcaa agtcaaggag catggaatcc cggcccctca ggagcaggtg    1500
accgtggcct gcgaggaggg ctggaccctg actggctgca gtgccctccc tgggacctcc    1560
cacgtcctgg gggcctacgc cgtagacaac acgtgtgtag tcaggagccg ggacgtcagc    1620
actacaggca gcaccagcga aggggccgtg acagccgttg ccatctgctg ccggagccgg    1680
cacctggcgc aggcctccca ggagctccag ggaggtggag cacacccgg ccgtcccaga    1740 gcagtgccca cacagtgcga cgtcccccccc aacagccgct tcgattgcgc ccctgacaag    1800
gccatcaccc aggaacagtg cgaggcccgc ggctgttgct acatccctgc aaagcagggg    1860
ctgcagggag cccagatggg gcagccctgg tgcttcttcc cacccagcta ccccagctac    1920
aagctggaga acctgagctc ctctgaaatg ggctacacgg ccaccctgac ccgtaccacc    1980
cccaccttct tccccaagga catcctgacc ctgcggctgg acgtgatgat ggagactgag    2040
aaccgcctcc acttcacgat caaagatcca gctaacaggc gctacgaggt gcccttggag    2100
accccgcatg tccacagccg ggcaccgtcc ccactctaca gcgtggagtt ctccgaggag    2160
cccttcgggg tgatcgtgcg ccggcagctg acggccgcg tgctgctgaa cacgacggtg    2220
gcgcccctgt tctttgcgga ccagttcctt cagctgtcca cctcgctgcc ctcgcagtat    2280
atcacaggcc tcgccgagca cctcagtccc ctgatgctca gcaccagctg gaccaggatc    2340
accctgtgga accgggacct tgcgcccacg cccggtgcga acctctacgg gtctcaccct    2400
```

| | |
|---|---|
| ttctacctgg cgctggagga cggcgggtcg gcacacgggg tgttcctgct aaacagcaat | 2460 |
| gccatggatg tggtcctgca gccgagccct gcccttagct ggaggtcgac aggtgggatc | 2520 |
| ctggatgtct acatcttcct gggcccagag cccaagagcg tggtgcagca gtacctggac | 2580 |
| gttgtgggat acccgttcat gccgccatac tggggcctgg gcttccacct gtgccgctgg | 2640 |
| ggctactcct ccaccgctat cacccgccag gtggtggaga acatgaccag ggcccacttc | 2700 |
| cccctgacg tccagtggaa cgacctggac tacatggact cccggaggga cttcacgttc | 2760 |
| aacaaggatg cttccgggga cttcccggcc atggtgcagg agctgcacca gggcggccgg | 2820 |
| cgctacatga tgatcgtgga tcctgccatc agcagctcgg gccctgccgg gagctacagg | 2880 |
| ccctacgacg agggtctgcg gaggggggtt ttcatcacca acgagaccgg ccagccgctg | 2940 |
| attgggaagg tatggcccgg gtccactgcc ttccccgact tcaccaaccc cacagccctg | 3000 |
| gcctggtggg aggacatggt ggctgagttc catgaccagg tgcccttcga cggcatgtgg | 3060 |
| attgacatga acgagccttc caacttcatc aggggctctg aggacggctg ccccaacaat | 3120 |
| gagctggaga acccaccta cgtgcctggg gtggttgggg gaccctcca ggcggccacc | 3180 |
| atctgtgcct ccagccacca gtttctctcc acacactaca acctgcacaa cctctacggc | 3240 |
| ctgaccgaag ccatcgcctc ccacagggcg ctggtgaagg ctcggggggac acgcccattt | 3300 |
| gtgatctccc gctcgacctt tgctggccac ggccgatacg ccggccactg acggggggac | 3360 |
| gtgtggagct cctgggagca gctcgcctcc tccgtgccag aaatcctgca gtttaacctg | 3420 |
| ctggggggtgc ctctggtcgg ggccgacgtc tgcggcttcc tgggcaacac ctcagaggag | 3480 |
| ctgtgtgtgc gctggaccca gctggggggcc ttctacccct tcatgcggaa ccacaacagc | 3540 |
| ctgctcagtc tgccccagga gccgtacagc ttcagcgagc cggcccagca ggccatgagg | 3600 |
| aaggccctca ccctgcgcta cgcactcctc cccccacctct acacactgtt ccaccaggcc | 3660 |
| cacgtcgcgg gggagaccgt ggcccggccc ctcttcctgg agttccccaa ggactctagc | 3720 |
| acctggactg tggaccacca gctcctgtgg gggaggccc tgctcatcac cccagtgctc | 3780 |
| caggccggga aggccgaagt gactggctac ttccccttgg gcacatggta cgacctgcag | 3840 |
| acggtgccag tagaggccct tggcagcctc ccaccccac ctgcagctcc ccgtgagcca | 3900 |
| gccatccaca gcgaggggca gtgggtgacg ctgccggccc ccctggacac catcaacgtc | 3960 |
| cacctccggg ctgggtacat catccccctg cagggccctg gcctcacaac cacagagtcc | 4020 |
| cgccagcagc ccatggccct ggctgtggcc ctgaccaagg gtggggaggc ccgaggggag | 4080 |
| ctgttctggg acgatggaga gagcctggaa gtgctggagc gaggggccta cacacaggtc | 4140 |
| atcttcctgg ccaggaataa cacgatcgtg aatgagctgg tacgtgtgac cagtgaggga | 4200 |
| gctggcctgc agctgcagaa ggtgactgtc ctgggcgtgg ccacggcgcc ccagcaggtc | 4260 |
| ctctccaacg gtgtccctgt ctccaacttc acctacagcc ccgacaccaa ggtcctggac | 4320 |
| atctgtgtct cgctgttgat gggagagcag tttctcgtca gctggtgtta g | 4371 |

<210> SEQ ID NO 15
<211> LENGTH: 3861
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

| | |
|---|---|
| atggaggcgg tggcggtggc cgcggcggtg ggggtccttc tcctggccgg ggccgggggc | 60 |

```
gcggcaggcg acgaggcccg ggaggcggcg gccgtgcggg cgctcgtggc ccggctgctg     120
gggccaggcc ccgcggccga cttctccgtg tcggtggagc gcgctctggc tgccaagccg     180
ggcttggaca cctacagcct gggcggcggc ggcgcggcgc gcgtgcgggt gcgcggctcc     240
acgggcgtgg cggccgccgc ggggctgcac cgctacctgc gcgacttctg tggctgccac     300
gtggcctggt ccggctctca gctgcgcctg ccgcggccac tgccagccgt gccggggggag    360 ctgaccgagg ccacgcccaa caggtaccgc tattaccaga atgtgtgcac gcaaagctac     420
tccttcgtgt ggtgggactg ggcccgctgg gagcgagaga tagactggat ggcgctgaat     480
ggcatcaacc tggcactggc ctggagcggc caggaggcca tctggcagcg ggtgtacctg     540
gccttgggcc tgacccaggc agagatcaat gagttcttta ctggtcctgc cttcctggcc     600
tgggggcgaa tggcaacct gcacacctgg gatggccccc tgccccctc ctggcacatc      660 aagcagcttt acctgcagca ccgggtcctg gaccagatgc gctccttcgg catgacccca    720
gtgctgcctg cattcgcggg gcatgttccc gaggctgtca ccagggtgtt ccctcaggtc    780
aatgtcacga agatgggcag ttggggccac tttaactgtt cctactcctg ctccttcctt    840
ctggctccgg aagaccccat attccccatc atcgggagcc tcttcctgcg agagctgatc    900
aaagagtttg gcacagacca catctatggg gccgacactt tcaatgagat gcagccacct    960
tcctcagagc cctcctacct tgccgcagcc accactgccg tctatgaggc catgactgca   1020
gtggatactg aggctgtgtg gctgctccaa ggctggctct tccagcacca gccgcagttc   1080
tgggggcccg cccagatcag ggctgtgctg ggagctgtgc cccgtggccg cctcctggtt   1140
ctggacctgt ttgctgagag ccagcctgtg tatacccgca ctgcctcctt ccagggccag   1200
cccttcatct ggtgcatgct gcacaacttt gggggaaacc atggtctttt tggagcccta   1260
gaggctgtga acggaggccc agaagctgcc cgcctcttcc ccaactccac catggtaggc   1320
acgggcatgg cccccgaggg catcagccag aacgaagtgg tctattccct catggctgag   1380
ctgggctggc gaaaggaccc agtgccagat ttggcagcct gggtgaccag cttcgccgcc   1440
cggcggtatg gggtctccca cccgacgca ggggcagcgt ggaggctact gctccggagt    1500
gtgtacaact gctccgggga ggcctgcagg ggccacaatc gtagcccgct ggtcaggcgg   1560
ccgtccctac agatgaatac cagcatctgg tacaaccgat ctgatgtgtt tgaggcctgg   1620
cggctgctgc tcacatctgc tccctccctg gccaccagcc ccgccttccg ctacgacctg   1680
ctggacctca ctcggcaggc agtgcaggag ctggtcagct tgtactatga ggaggcaaga   1740
agcgcctacc tgagcaagga gctggcctcc ctgttgaggg ctggaggcgt cctggcctat   1800
gagctgctgc cggcactgga cgaggtgctg gctagtgaca ccgcttctt gctgggcagc   1860 tggctagagc aggcccgagc agcggcagtc agtgaggccg aggccgattt ctacgagcag   1920
aacagccgct accagctgac cttgtggggg ccagaaggca acatcctgga ctatgccaac   1980
aagcagctgc cggggttggt ggccaactac tacaccctc gctggcggct tttcctggag    2040
gcgctggttg acagtgtggc ccagggcatc cctttccaac agcaccagtt tgacaaaaat   2100
gtcttccaac tggagcaggc cttcgttctc agcaagcaga ggtacccag ccagccgcga     2160 ggagacactg tggacctggc caagaagatc ttcctcaaat attaccccg ctgggtggcc     2220 ggctcttggg gaggtggaag catcccgtgg aacctggagc ggattacccc tccacggtac   2280
cgggcggatg aataccagcc ccccgacgga ggcagcctgg tggaggtgta tctcctagac   2340
accagcatac agagtgacca ccgggaaatc gagggcaggg tcatggtcac cgacttcgag   2400
```

| | | |
|---|---|---|
| aatgtgcccg aggaggacgg gacccgcttc cacagacagg ccagcaagtg tgacagtcat | 2460 |
| ggcacccacc tggcaggggt ggtcagcggc cgggatgccg gcgtggccaa gggtgccagc | 2520 |
| atgcgcagcc tgcgcgtgct caactgccaa gggaagggca cggttagcgg caccctcata | 2580 |
| ggcctggagt ttattcggaa aagccagctg gtccagcctg tggggccact ggtggtgctg | 2640 |
| ctgcccctgg cgggtgggta cagccgcgtc ctcaacgccg cctgccagcg cctggcgagg | 2700 |
| gctggggtcg tgctggtcac cgctgccggc aacttccggg acgatgcctg cctctactcc | 2760 |
| ccagcctcag ctcccgaggt catcacagtt ggggccacca atgcccaaga ccagccggtg | 2820 |
| accctgggga ctttggggac caactttggc cgctgtgtgg acctcttrgc cccaggggag | 2880 |
| gacatcattg gtgcctccag cgactgcagc acctgcgctg tgtcacagag tgggacagca | 2940 |
| caggctgctg cccacgtggc tggcattgca gccatgatgc tgtctgccga gccggagctc | 3000 |
| accctggccg agttgaggca gagactgatc cacttctctg ccaaagatgt catcaatgag | 3060 |
| gcctggttcc ctgaggacca gcgggtactg acccccaacc tggtggccgc cctgcccccc | 3120 |
| agcacccatg gggcaggttg gcagctgttt tgcaggacta tatggtcagc acactcgggg | 3180 |
| cctacacgga tggccacagc cgtcgcccgc tgcgccccag atgaggagct gctgagctgc | 3240 |
| tccagtttct ccaggagtgg gaagcggcgg ggcgagcgca tggaggccca aggggcaag | 3300 |
| ctggtctgcc gggcccacaa cgcttttggg ggtgagggtg tctacgccat tgccaggtgc | 3360 |
| tgcctgctac cccaggccaa ctgcagcgtc cacacagctc caccagctga ggccagcatg | 3420 |
| gggacccgtg tccactgcca ccaacagggc cacgtcctca caggctgcag ctcccactgg | 3480 |
| gaggtggagg accttggcac ccacaagccg cctgtgctga ggccacgagg tcagcccaac | 3540 |
| cagtgcgtgg gccacaggga ggccagcatc cacgcttcct gctgccatgc cccaggtctg | 3600 |
| gaatgcaaag tcaaggagca tggaatcccg gcccctcagg agcaggtgac cgtggcctgc | 3660 |
| gaggagggct ggaccctgac tggctgcagt gccctccctg ggacctccca cgtcctgggg | 3720 |
| gcctacgccg tagacaacac gtgtgtagtc aggagccggg acgtcagcac tacaggcagc | 3780 |
| accagcgaag gggccgtgac agccgttgcc atctgctgcc ggagccggca cctggcgcag | 3840 |
| gcctcccagg agctccagta g | 3861 |

<210> SEQ ID NO 16
<211> LENGTH: 459
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

| | |
|---|---|
| atgggcaccg tcagctccag gcggtcctgg tggccgctgc cactgctgct gctgctgctg | 60 |
| ctgctcctgg gtcccgcggg cgcccgtgcg caggaggacg aggacggcga ctacgaggag | 120 |
| ctggtgctag ccttgcgttc cgaggaggac ggcctggccg aagcacccga gcacggaacc | 180 |
| acagccacct tccaccgctg cgccaaggat ccgtggaggt tgcctggcac ctacgtggtg | 240 |
| gtgctgaagg aggagaccca cctctcgcag tcagagcgca ctgcccgccg cctgcaggcc | 300 |
| caggctgccc gccggggata cctcaccaag atcctgcatg tcttccatgg ccttcttcct | 360 |
| ggcttcctgg tgaagatgag tggcgacctg ctggagctgg ccttgaagtt gccccatgtc | 420 |
| gactacatcg aggaggactc ctctgtcttt gcccagtga | 459 |

```
<210> SEQ ID NO 17
<211> LENGTH: 1456
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17
```

| | | | | | | | | | | | | | | | |
|---|---|---|---|---|---|---|---|---|---|---|---|---|---|---|---|
| Met | Gly | Thr | Val | Ser | Ser | Arg | Arg | Ser | Trp | Trp | Pro | Leu | Pro | Leu | Leu |
| 1 | | | | 5 | | | | | 10 | | | | | 15 | |
| Leu | Leu | Leu | Leu | Leu | Leu | Leu | Gly | Pro | Ala | Gly | Ala | Arg | Ala | Ser | Ile |
| | | | 20 | | | | | 25 | | | | | 30 | | |
| Pro | Trp | Asn | Leu | Glu | Arg | Ile | Thr | Pro | Pro | Arg | Tyr | Arg | Ala | Asp | Glu |
| | | | 35 | | | | | 40 | | | | | 45 | | |
| Tyr | Gln | Pro | Pro | Asp | Gly | Gly | Ser | Leu | Val | Glu | Val | Tyr | Leu | Leu | Asp |
| | 50 | | | | | 55 | | | | | 60 | | | | |
| Thr | Ser | Ile | Gln | Ser | Asp | His | Arg | Glu | Ile | Glu | Gly | Arg | Val | Met | Val |
| 65 | | | | | 70 | | | | | 75 | | | | | 80 |
| Thr | Asp | Phe | Glu | Asn | Val | Pro | Glu | Glu | Asp | Gly | Thr | Arg | Phe | His | Arg |
| | | | | 85 | | | | | 90 | | | | | 95 | |
| Gln | Ala | Ser | Lys | Cys | Asp | Ser | His | Gly | Thr | His | Leu | Ala | Gly | Val | Val |
| | | | 100 | | | | | 105 | | | | | 110 | | |
| Ser | Gly | Arg | Asp | Ala | Gly | Val | Ala | Lys | Gly | Ala | Ser | Met | Arg | Ser | Leu |
| | | | 115 | | | | | 120 | | | | | 125 | | |
| Arg | Val | Leu | Asn | Cys | Gln | Gly | Lys | Gly | Thr | Val | Ser | Gly | Thr | Leu | Ile |
| | 130 | | | | | 135 | | | | | 140 | | | | |
| Gly | Leu | Glu | Phe | Ile | Arg | Lys | Ser | Gln | Leu | Val | Gln | Pro | Val | Gly | Pro |
| 145 | | | | | 150 | | | | | 155 | | | | | 160 |
| Leu | Val | Val | Leu | Leu | Pro | Leu | Ala | Gly | Gly | Tyr | Ser | Arg | Val | Leu | Asn |
| | | | | 165 | | | | | 170 | | | | | 175 | |
| Ala | Ala | Cys | Gln | Arg | Leu | Ala | Arg | Ala | Gly | Val | Val | Leu | Val | Thr | Ala |
| | | | 180 | | | | | 185 | | | | | 190 | | |
| Ala | Gly | Asn | Phe | Arg | Asp | Asp | Ala | Cys | Leu | Tyr | Ser | Pro | Ala | Ser | Ala |
| | | | 195 | | | | | 200 | | | | | 205 | | |
| Pro | Glu | Val | Ile | Thr | Val | Gly | Ala | Thr | Asn | Ala | Gln | Asp | Gln | Pro | Val |
| | 210 | | | | | 215 | | | | | 220 | | | | |
| Thr | Leu | Gly | Thr | Leu | Gly | Thr | Asn | Phe | Gly | Arg | Cys | Val | Asp | Leu | Phe |
| 225 | | | | | 230 | | | | | 235 | | | | | 240 |
| Ala | Pro | Gly | Glu | Asp | Ile | Ile | Gly | Ala | Ser | Ser | Asp | Cys | Ser | Thr | Cys |
| | | | | 245 | | | | | 250 | | | | | 255 | |
| Ala | Val | Ser | Gln | Ser | Gly | Thr | Ala | Gln | Ala | Ala | His | Val | Ala | Gly | |
| | | | 260 | | | | | 265 | | | | | 270 | | |
| Ile | Ala | Ala | Met | Met | Leu | Ser | Ala | Glu | Pro | Glu | Leu | Thr | Leu | Ala | Glu |
| | | | 275 | | | | | 280 | | | | | 285 | | |
| Leu | Arg | Gln | Arg | Leu | Ile | His | Phe | Ser | Ala | Lys | Asp | Val | Ile | Asn | Glu |
| | 290 | | | | | 295 | | | | | 300 | | | | |
| Ala | Trp | Phe | Pro | Glu | Asp | Gln | Arg | Val | Leu | Thr | Pro | Asn | Leu | Val | Ala |
| 305 | | | | | 310 | | | | | 315 | | | | | 320 |
| Ala | Leu | Pro | Pro | Ser | Thr | His | Gly | Ala | Gly | Trp | Gln | Leu | Phe | Cys | Arg |
| | | | | 325 | | | | | 330 | | | | | 335 | |
| Thr | Val | Trp | Ser | Ala | His | Ser | Gly | Pro | Thr | Arg | Met | Ala | Thr | Ala | Val |
| | | | 340 | | | | | 345 | | | | | 350 | | |
| Ala | Arg | Cys | Ala | Pro | Asp | Glu | Glu | Leu | Leu | Ser | Cys | Ser | Ser | Phe | Ser |
| | | | 355 | | | | | 360 | | | | | 365 | | |

-continued

```
Arg Ser Gly Lys Arg Gly Glu Arg Met Glu Ala Gln Gly Gly Lys
    370                 375                 380

Leu Val Cys Arg Ala His Asn Ala Phe Gly Gly Glu Gly Val Tyr Ala
385                 390                 395                 400

Ile Ala Arg Cys Cys Leu Leu Pro Gln Ala Asn Cys Ser Val His Thr
                405                 410                 415

Ala Pro Pro Ala Glu Ala Ser Met Gly Thr Arg Val His Cys His Gln
            420                 425                 430

Gln Gly His Val Leu Thr Gly Cys Ser Ser His Trp Glu Val Glu Asp
        435                 440                 445

Leu Gly Thr His Lys Pro Pro Val Leu Arg Pro Arg Gly Gln Pro Asn
    450                 455                 460

Gln Cys Val Gly His Arg Glu Ala Ser Ile His Ala Ser Cys Cys His
465                 470                 475                 480

Ala Pro Gly Leu Glu Cys Lys Val Lys Glu His Gly Ile Pro Ala Pro
                485                 490                 495

Gln Glu Gln Val Thr Val Ala Cys Glu Gly Trp Thr Leu Thr Gly
            500                 505                 510

Cys Ser Ala Leu Pro Gly Thr Ser His Val Leu Gly Ala Tyr Ala Val
        515                 520                 525

Asp Asn Thr Cys Val Val Arg Ser Arg Asp Val Ser Thr Thr Gly Ser
    530                 535                 540

Thr Ser Glu Gly Ala Val Thr Ala Val Ala Ile Cys Cys Arg Ser Arg
545                 550                 555                 560

His Leu Ala Gln Ala Ser Gln Glu Leu Gln Gly Gly Ala His Pro
                565                 570                 575

Gly Arg Pro Arg Ala Val Pro Thr Gln Cys Asp Val Pro Pro Asn Ser
            580                 585                 590

Arg Phe Asp Cys Ala Pro Asp Lys Ala Ile Thr Gln Glu Gln Cys Glu
        595                 600                 605

Ala Arg Gly Cys Cys Tyr Ile Pro Ala Lys Gln Gly Leu Gln Gly Ala
    610                 615                 620

Gln Met Gly Gln Pro Trp Cys Phe Phe Pro Pro Ser Tyr Pro Ser Tyr
625                 630                 635                 640

Lys Leu Glu Asn Leu Ser Ser Ser Glu Met Gly Tyr Thr Ala Thr Leu
                645                 650                 655

Thr Arg Thr Thr Pro Thr Phe Phe Pro Lys Asp Ile Leu Thr Leu Arg
            660                 665                 670

Leu Asp Val Met Met Glu Thr Glu Asn Arg Leu His Phe Thr Ile Lys
        675                 680                 685

Asp Pro Ala Asn Arg Arg Tyr Glu Val Pro Leu Glu Thr Pro His Val
    690                 695                 700

His Ser Arg Ala Pro Ser Pro Leu Tyr Ser Val Glu Phe Ser Glu Glu
705                 710                 715                 720

Pro Phe Gly Val Ile Val Arg Arg Gln Leu Asp Gly Arg Val Leu Leu
                725                 730                 735

Asn Thr Thr Val Ala Pro Leu Phe Phe Ala Asp Gln Phe Leu Gln Leu
            740                 745                 750

Ser Thr Ser Leu Pro Ser Gln Tyr Ile Thr Gly Leu Ala Glu His Leu
        755                 760                 765

Ser Pro Leu Met Leu Ser Thr Ser Trp Thr Arg Ile Thr Leu Trp Asn
    770                 775                 780
```

```
Arg Asp Leu Ala Pro Thr Pro Gly Ala Asn Leu Tyr Gly Ser His Pro
785                 790                 795                 800

Phe Tyr Leu Ala Leu Glu Asp Gly Gly Ser Ala His Gly Val Phe Leu
                805                 810                 815

Leu Asn Ser Asn Ala Met Asp Val Val Leu Gln Pro Ser Pro Ala Leu
            820                 825                 830

Ser Trp Arg Ser Thr Gly Gly Ile Leu Asp Val Tyr Ile Phe Leu Gly
        835                 840                 845

Pro Glu Pro Lys Ser Val Val Gln Gln Tyr Leu Asp Val Gly Tyr
    850                 855                 860

Pro Phe Met Pro Pro Tyr Trp Gly Leu Gly Phe His Leu Cys Arg Trp
865                 870                 875                 880

Gly Tyr Ser Ser Thr Ala Ile Thr Arg Gln Val Val Glu Asn Met Thr
                885                 890                 895

Arg Ala His Phe Pro Leu Asp Val Gln Trp Asn Asp Leu Asp Tyr Met
            900                 905                 910

Asp Ser Arg Arg Asp Phe Thr Phe Asn Lys Asp Gly Phe Arg Asp Phe
        915                 920                 925

Pro Ala Met Val Gln Glu Leu His Gln Gly Gly Arg Arg Tyr Met Met
    930                 935                 940

Ile Val Asp Pro Ala Ile Ser Ser Ser Gly Pro Ala Gly Ser Tyr Arg
945                 950                 955                 960

Pro Tyr Asp Glu Gly Leu Arg Arg Gly Val Phe Ile Thr Asn Glu Thr
                965                 970                 975

Gly Gln Pro Leu Ile Gly Lys Val Trp Pro Gly Ser Thr Ala Phe Pro
            980                 985                 990

Asp Phe Thr Asn Pro Thr Ala Leu Ala Trp Trp Glu Asp Met Val Ala
        995                 1000                1005

Glu Phe His Asp Gln Val Pro Phe Asp Gly Met Trp Ile Asp Met
    1010                1015                1020

Asn Glu Pro Ser Asn Phe Ile Arg Gly Ser Glu Asp Gly Cys Pro
    1025                1030                1035

Asn Asn Glu Leu Glu Asn Pro Pro Tyr Val Pro Gly Val Val Gly
    1040                1045                1050

Gly Thr Leu Gln Ala Ala Thr Ile Cys Ala Ser Ser His Gln Phe
    1055                1060                1065

Leu Ser Thr His Tyr Asn Leu His Asn Leu Tyr Gly Leu Thr Glu
    1070                1075                1080

Ala Ile Ala Ser His Arg Ala Leu Val Lys Ala Arg Gly Thr Arg
    1085                1090                1095

Pro Phe Val Ile Ser Arg Ser Thr Phe Ala Gly His Gly Arg Tyr
    1100                1105                1110

Ala Gly His Trp Thr Gly Asp Val Trp Ser Ser Trp Glu Gln Leu
    1115                1120                1125

Ala Ser Ser Val Pro Glu Ile Leu Gln Phe Asn Leu Leu Gly Val
    1130                1135                1140

Pro Leu Val Gly Ala Asp Val Cys Gly Phe Leu Gly Asn Thr Ser
    1145                1150                1155

Glu Glu Leu Cys Val Arg Trp Thr Gln Leu Gly Ala Phe Tyr Pro
    1160                1165                1170

Phe Met Arg Asn His Asn Ser Leu Leu Ser Leu Pro Gln Glu Pro
    1175                1180                1185

Tyr Ser Phe Ser Glu Pro Ala Gln Gln Ala Met Arg Lys Ala Leu
```

```
                    1190                1195                1200

Thr Leu Arg Tyr Ala Leu Leu Pro His Leu Tyr Thr Leu Phe His
    1205                1210                1215

Gln Ala His Val Ala Gly Glu Thr Val Ala Arg Pro Leu Phe Leu
    1220                1225                1230

Glu Phe Pro Lys Asp Ser Ser Thr Trp Thr Val Asp His Gln Leu
    1235                1240                1245

Leu Trp Gly Glu Ala Leu Leu Ile Thr Pro Val Leu Gln Ala Gly
    1250                1255                1260

Lys Ala Glu Val Thr Gly Tyr Phe Pro Leu Gly Thr Trp Tyr Asp
    1265                1270                1275

Leu Gln Thr Val Pro Val Glu Ala Leu Gly Ser Leu Pro Pro Pro
    1280                1285                1290

Pro Ala Ala Pro Arg Glu Pro Ala Ile His Ser Glu Gly Gln Trp
    1295                1300                1305

Val Thr Leu Pro Ala Pro Leu Asp Thr Ile Asn Val His Leu Arg
    1310                1315                1320

Ala Gly Tyr Ile Ile Pro Leu Gln Gly Pro Gly Leu Thr Thr Thr
    1325                1330                1335

Glu Ser Arg Gln Gln Pro Met Ala Leu Ala Val Ala Leu Thr Lys
    1340                1345                1350

Gly Gly Glu Ala Arg Gly Glu Leu Phe Trp Asp Asp Gly Glu Ser
    1355                1360                1365

Leu Glu Val Leu Glu Arg Gly Ala Tyr Thr Gln Val Ile Phe Leu
    1370                1375                1380

Ala Arg Asn Asn Thr Ile Val Asn Glu Leu Val Arg Val Thr Ser
    1385                1390                1395

Glu Gly Ala Gly Leu Gln Leu Gln Lys Val Thr Val Leu Gly Val
    1400                1405                1410

Ala Thr Ala Pro Gln Gln Val Leu Ser Asn Gly Val Pro Val Ser
    1415                1420                1425

Asn Phe Thr Tyr Ser Pro Asp Thr Lys Val Leu Asp Ile Cys Val
    1430                1435                1440

Ser Leu Leu Met Gly Glu Gln Phe Leu Val Ser Trp Cys
    1445                1450                1455

<210> SEQ ID NO 18
<211> LENGTH: 1286
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Met Glu Ala Val Ala Val Ala Ala Ala Val Gly Val Leu Leu Leu Ala
1               5                   10                  15

Gly Ala Gly Gly Ala Ala Gly Asp Glu Ala Arg Glu Ala Ala Ala Val
                20                  25                  30

Arg Ala Leu Val Ala Arg Leu Leu Gly Pro Gly Pro Ala Ala Asp Phe
            35                  40                  45

Ser Val Ser Val Glu Arg Ala Leu Ala Ala Lys Pro Gly Leu Asp Thr
        50                  55                  60

Tyr Ser Leu Gly Gly Gly Gly Ala Ala Arg Val Arg Val Arg Gly Ser
65                  70                  75                  80
```

-continued

```
Thr Gly Val Ala Ala Ala Ala Gly Leu His Arg Tyr Leu Arg Asp Phe
                 85                  90                  95
Cys Gly Cys His Val Ala Trp Ser Gly Ser Gln Leu Arg Leu Pro Arg
            100                 105                 110
Pro Leu Pro Ala Val Pro Gly Glu Leu Thr Glu Ala Thr Pro Asn Arg
        115                 120                 125
Tyr Arg Tyr Tyr Gln Asn Val Cys Thr Gln Ser Tyr Ser Phe Val Trp
    130                 135                 140
Trp Asp Trp Ala Arg Trp Glu Arg Glu Ile Asp Trp Met Ala Leu Asn
145                 150                 155                 160
Gly Ile Asn Leu Ala Leu Ala Trp Ser Gly Gln Glu Ala Ile Trp Gln
                165                 170                 175
Arg Val Tyr Leu Ala Leu Gly Leu Thr Gln Ala Glu Ile Asn Glu Phe
            180                 185                 190
Phe Thr Gly Pro Ala Phe Leu Ala Trp Gly Arg Met Gly Asn Leu His
        195                 200                 205
Thr Trp Asp Gly Pro Leu Pro Pro Ser Trp His Ile Lys Gln Leu Tyr
    210                 215                 220
Leu Gln His Arg Val Leu Asp Gln Met Arg Ser Phe Gly Met Thr Pro
225                 230                 235                 240
Val Leu Pro Ala Phe Ala Gly His Val Pro Glu Ala Val Thr Arg Val
                245                 250                 255
Phe Pro Gln Val Asn Val Thr Lys Met Gly Ser Trp Gly His Phe Asn
            260                 265                 270
Cys Ser Tyr Ser Cys Ser Phe Leu Leu Ala Pro Glu Asp Pro Ile Phe
        275                 280                 285
Pro Ile Ile Gly Ser Leu Phe Leu Arg Glu Leu Ile Lys Glu Phe Gly
    290                 295                 300
Thr Asp His Ile Tyr Gly Ala Asp Thr Phe Asn Glu Met Gln Pro Pro
305                 310                 315                 320
Ser Ser Glu Pro Ser Tyr Leu Ala Ala Ala Thr Thr Ala Val Tyr Glu
                325                 330                 335
Ala Met Thr Ala Val Asp Thr Glu Ala Val Trp Leu Leu Gln Gly Trp
            340                 345                 350
Leu Phe Gln His Gln Pro Gln Phe Trp Gly Pro Ala Gln Ile Arg Ala
        355                 360                 365
Val Leu Gly Ala Val Pro Arg Gly Arg Leu Leu Val Leu Asp Leu Phe
    370                 375                 380
Ala Glu Ser Gln Pro Val Tyr Thr Arg Thr Ala Ser Phe Gln Gly Gln
385                 390                 395                 400
Pro Phe Ile Trp Cys Met Leu His Asn Phe Gly Gly Asn His Gly Leu
                405                 410                 415
Phe Gly Ala Leu Glu Ala Val Asn Gly Gly Pro Glu Ala Ala Arg Leu
            420                 425                 430
Phe Pro Asn Ser Thr Met Val Gly Thr Gly Met Ala Pro Glu Gly Ile
        435                 440                 445
Ser Gln Asn Glu Val Val Tyr Ser Leu Met Ala Glu Leu Gly Trp Arg
    450                 455                 460
Lys Asp Pro Val Pro Asp Leu Ala Ala Trp Val Thr Ser Phe Ala Ala
465                 470                 475                 480
Arg Arg Tyr Gly Val Ser His Pro Asp Ala Gly Ala Ala Trp Arg Leu
                485                 490                 495
```

```
Leu Leu Arg Ser Val Tyr Asn Cys Ser Gly Glu Ala Cys Arg Gly His
            500                 505                 510

Asn Arg Ser Pro Leu Val Arg Pro Ser Leu Gln Met Asn Thr Ser
        515                 520                 525

Ile Trp Tyr Asn Arg Ser Asp Val Phe Glu Ala Trp Arg Leu Leu Leu
    530                 535                 540

Thr Ser Ala Pro Ser Leu Ala Thr Ser Pro Ala Phe Arg Tyr Asp Leu
545                 550                 555                 560

Leu Asp Leu Thr Arg Gln Ala Val Gln Glu Leu Val Ser Leu Tyr Tyr
                565                 570                 575

Glu Glu Ala Arg Ser Ala Tyr Leu Ser Lys Glu Leu Ala Ser Leu Leu
            580                 585                 590

Arg Ala Gly Gly Val Leu Ala Tyr Glu Leu Pro Ala Leu Asp Glu
        595                 600                 605

Val Leu Ala Ser Asp Ser Arg Phe Leu Leu Gly Ser Trp Leu Glu Gln
    610                 615                 620

Ala Arg Ala Ala Ala Val Ser Glu Ala Glu Ala Asp Phe Tyr Glu Gln
625                 630                 635                 640

Asn Ser Arg Tyr Gln Leu Thr Leu Trp Gly Pro Glu Gly Asn Ile Leu
                645                 650                 655

Asp Tyr Ala Asn Lys Gln Leu Ala Gly Leu Val Ala Asn Tyr Tyr Thr
            660                 665                 670

Pro Arg Trp Arg Leu Phe Leu Glu Ala Leu Val Asp Ser Val Ala Gln
        675                 680                 685

Gly Ile Pro Phe Gln Gln His Gln Phe Asp Lys Asn Val Phe Gln Leu
690                 695                 700

Glu Gln Ala Phe Val Leu Ser Lys Gln Arg Tyr Pro Ser Gln Pro Arg
705                 710                 715                 720

Gly Asp Thr Val Asp Leu Ala Lys Lys Ile Phe Leu Lys Tyr Tyr Pro
                725                 730                 735

Arg Trp Val Ala Gly Ser Trp Gly Gly Ser Ile Pro Trp Asn Leu
            740                 745                 750

Glu Arg Ile Thr Pro Pro Arg Tyr Arg Ala Asp Glu Tyr Gln Pro Pro
        755                 760                 765

Asp Gly Gly Ser Leu Val Glu Val Tyr Leu Leu Asp Thr Ser Ile Gln
770                 775                 780

Ser Asp His Arg Glu Ile Glu Gly Arg Val Met Val Thr Asp Phe Glu
785                 790                 795                 800

Asn Val Pro Glu Glu Asp Gly Thr Arg Phe His Arg Gln Ala Ser Lys
                805                 810                 815

Cys Asp Ser His Gly Thr His Leu Ala Gly Val Val Ser Gly Arg Asp
            820                 825                 830

Ala Gly Val Ala Lys Gly Ala Ser Met Arg Ser Leu Arg Val Leu Asn
        835                 840                 845

Cys Gln Gly Lys Gly Thr Val Ser Gly Thr Leu Ile Gly Leu Glu Phe
850                 855                 860

Ile Arg Lys Ser Gln Leu Val Gln Pro Val Gly Pro Leu Val Val Leu
865                 870                 875                 880

Leu Pro Leu Ala Gly Gly Tyr Ser Arg Val Leu Asn Ala Ala Cys Gln
                885                 890                 895

Arg Leu Ala Arg Ala Gly Val Val Leu Val Thr Ala Ala Gly Asn Phe
            900                 905                 910

Arg Asp Asp Ala Cys Leu Tyr Ser Pro Ala Ser Ala Pro Glu Val Ile
```

915                 920                 925
Thr Val Gly Ala Thr Asn Ala Gln Asp Gln Pro Val Thr Leu Gly Thr
            930                 935                 940
Leu Gly Thr Asn Phe Gly Arg Cys Val Asp Leu Phe Ala Pro Gly Glu
945                 950                 955                 960
Asp Ile Ile Gly Ala Ser Ser Asp Cys Ser Thr Cys Ala Val Ser Gln
                965                 970                 975
Ser Gly Thr Ala Gln Ala Ala Ala His Val Ala Gly Ile Ala Ala Met
            980                 985                 990
Met Leu Ser Ala Glu Pro Glu Leu Thr Leu Ala Glu Leu Arg Gln Arg
                995                1000                1005
Leu Ile His Phe Ser Ala Lys Asp Val Ile Asn Glu Ala Trp Phe
            1010                1015                1020
Pro Glu Asp Gln Arg Val Leu Thr Pro Asn Leu Val Ala Ala Leu
            1025                1030                1035
Pro Pro Ser Thr His Gly Ala Gly Trp Gln Leu Phe Cys Arg Thr
            1040                1045                1050
Val Trp Ser Ala His Ser Gly Pro Thr Arg Met Ala Thr Ala Val
            1055                1060                1065
Ala Arg Cys Ala Pro Asp Glu Glu Leu Leu Ser Cys Ser Ser Phe
            1070                1075                1080
Ser Arg Ser Gly Lys Arg Arg Gly Glu Arg Met Glu Ala Gln Gly
            1085                1090                1095
Gly Lys Leu Val Cys Arg Ala His Asn Ala Phe Gly Gly Glu Gly
            1100                1105                1110
Val Tyr Ala Ile Ala Arg Cys Cys Leu Leu Pro Gln Ala Asn Cys
            1115                1120                1125
Ser Val His Thr Ala Pro Pro Ala Glu Ala Ser Met Gly Thr Arg
            1130                1135                1140
Val His Cys His Gln Gln Gly His Val Leu Thr Gly Cys Ser Ser
            1145                1150                1155
His Trp Glu Val Glu Asp Leu Gly Thr His Lys Pro Pro Val Leu
            1160                1165                1170
Arg Pro Arg Gly Gln Pro Asn Gln Cys Val Gly His Arg Glu Ala
            1175                1180                1185
Ser Ile His Ala Ser Cys Cys His Ala Pro Gly Leu Glu Cys Lys
            1190                1195                1200
Val Lys Glu His Gly Ile Pro Ala Pro Gln Glu Gln Val Thr Val
            1205                1210                1215
Ala Cys Glu Glu Gly Trp Thr Leu Thr Gly Cys Ser Ala Leu Pro
            1220                1225                1230
Gly Thr Ser His Val Leu Gly Ala Tyr Ala Val Asp Asn Thr Cys
            1235                1240                1245
Val Val Arg Ser Arg Asp Val Ser Thr Thr Gly Ser Thr Ser Glu
            1250                1255                1260
Gly Ala Val Thr Ala Val Ala Ile Cys Cys Arg Ser Arg His Leu
            1265                1270                1275
Ala Gln Ala Ser Gln Glu Leu Gln
            1280                1285

<210> SEQ ID NO 19
<211> LENGTH: 152
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 19

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln
145                 150

<210> SEQ ID NO 20
<211> LENGTH: 1583
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60

His Arg Cys Ala Lys Asp Pro Trp Arg Leu Pro Gly Thr Tyr Val Val
65                  70                  75                  80

Val Leu Lys Glu Glu Thr His Leu Ser Gln Ser Glu Arg Thr Ala Arg
                85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Arg Arg Arg Arg Ser Ile Pro
145                 150                 155                 160
```

```
Trp Asn Leu Glu Arg Ile Thr Pro Pro Arg Tyr Arg Ala Asp Glu Tyr
            165                 170                 175
Gln Pro Pro Asp Gly Gly Ser Leu Val Glu Val Tyr Leu Leu Asp Thr
        180                 185                 190
Ser Ile Gln Ser Asp His Arg Glu Ile Glu Gly Arg Val Met Val Thr
            195                 200                 205
Asp Phe Glu Asn Val Pro Glu Glu Asp Gly Thr Arg Phe His Arg Gln
210                 215                 220
Ala Ser Lys Cys Asp Ser His Gly Thr His Leu Ala Gly Val Val Ser
225                 230                 235                 240
Gly Arg Asp Ala Gly Val Ala Lys Gly Ala Ser Met Arg Ser Leu Arg
                245                 250                 255
Val Leu Asn Cys Gln Gly Lys Gly Thr Val Ser Gly Thr Leu Ile Gly
            260                 265                 270
Leu Glu Phe Ile Arg Lys Ser Gln Leu Val Gln Pro Val Gly Pro Leu
        275                 280                 285
Val Val Leu Leu Pro Leu Ala Gly Gly Tyr Ser Arg Val Leu Asn Ala
    290                 295                 300
Ala Cys Gln Arg Leu Ala Arg Ala Gly Val Val Leu Val Thr Ala Ala
305                 310                 315                 320
Gly Asn Phe Arg Asp Asp Ala Cys Leu Tyr Ser Pro Ala Ser Ala Pro
                325                 330                 335
Glu Val Ile Thr Val Gly Ala Thr Asn Ala Gln Asp Gln Pro Val Thr
            340                 345                 350
Leu Gly Thr Leu Gly Thr Asn Phe Gly Arg Cys Val Asp Leu Phe Ala
        355                 360                 365
Pro Gly Glu Asp Ile Ile Gly Ala Ser Ser Asp Cys Ser Thr Cys Ala
    370                 375                 380
Val Ser Gln Ser Gly Thr Ala Gln Ala Ala Ala His Val Ala Gly Ile
385                 390                 395                 400
Ala Ala Met Met Leu Ser Ala Glu Pro Glu Leu Thr Leu Ala Glu Leu
                405                 410                 415
Arg Gln Arg Leu Ile His Phe Ser Ala Lys Asp Val Ile Asn Glu Ala
            420                 425                 430
Trp Phe Pro Glu Asp Gln Arg Val Leu Thr Pro Asn Leu Val Ala Ala
        435                 440                 445
Leu Pro Pro Ser Thr His Gly Ala Gly Trp Gln Leu Phe Cys Arg Thr
    450                 455                 460
Val Trp Ser Ala His Ser Gly Pro Thr Arg Met Ala Thr Ala Val Ala
465                 470                 475                 480
Arg Cys Ala Pro Asp Glu Glu Leu Leu Ser Cys Ser Ser Phe Ser Arg
                485                 490                 495
Ser Gly Lys Arg Arg Gly Glu Arg Met Glu Ala Gln Gly Gly Lys Leu
            500                 505                 510
Val Cys Arg Ala His Asn Ala Phe Gly Gly Glu Gly Val Tyr Ala Ile
        515                 520                 525
Ala Arg Cys Cys Leu Leu Pro Gln Ala Asn Cys Ser Val His Thr Ala
    530                 535                 540
Pro Pro Ala Glu Ala Ser Met Gly Thr Arg Val His Cys His Gln Gln
545                 550                 555                 560
Gly His Val Leu Thr Gly Cys Ser Ser His Trp Glu Val Glu Asp Leu
                565                 570                 575
Gly Thr His Lys Pro Pro Val Leu Arg Pro Arg Gly Gln Pro Asn Gln
```

```
                580               585                590
    Cys Val Gly His Arg Glu Ala Ser Ile His Ala Ser Cys Cys His Ala
                    595                 600                 605

Pro Gly Leu Glu Cys Lys Val Lys Glu His Gly Ile Pro Ala Pro Gln
                    610                 615                 620

Glu Gln Val Thr Val Ala Cys Glu Glu Gly Trp Thr Leu Thr Gly Cys
    625                 630                 635                 640

Ser Ala Leu Pro Gly Thr Ser His Val Leu Gly Ala Tyr Ala Val Asp
                    645                 650                 655

Asn Thr Cys Val Val Arg Ser Arg Asp Val Ser Thr Thr Gly Ser Thr
                    660                 665                 670

Ser Glu Gly Ala Val Thr Ala Val Ala Ile Cys Cys Arg Ser Arg His
                    675                 680                 685

Leu Ala Gln Ala Ser Gln Glu Leu Gln Gly Gly Ala His Pro Gly
                    690                 695                 700

Arg Pro Arg Ala Val Pro Thr Gln Cys Asp Val Pro Pro Asn Ser Arg
    705                 710                 715                 720

Phe Asp Cys Ala Pro Asp Lys Ala Ile Thr Gln Glu Gln Cys Glu Ala
                    725                 730                 735

Arg Gly Cys Cys Tyr Ile Pro Ala Lys Gln Gly Leu Gln Gly Ala Gln
                    740                 745                 750

Met Gly Gln Pro Trp Cys Phe Phe Pro Pro Ser Tyr Pro Ser Tyr Lys
                    755                 760                 765

Leu Glu Asn Leu Ser Ser Ser Glu Met Gly Tyr Thr Ala Thr Leu Thr
                    770                 775                 780

Arg Thr Thr Pro Thr Phe Phe Pro Lys Asp Ile Leu Thr Leu Arg Leu
    785                 790                 795                 800

Asp Val Met Met Glu Thr Glu Asn Arg Leu His Phe Thr Ile Lys Asp
                    805                 810                 815

Pro Ala Asn Arg Arg Tyr Glu Val Pro Leu Glu Thr Pro His Val His
                    820                 825                 830

Ser Arg Ala Pro Ser Pro Leu Tyr Ser Val Glu Phe Ser Glu Glu Pro
                    835                 840                 845

Phe Gly Val Ile Val Arg Arg Gln Leu Asp Gly Arg Val Leu Leu Asn
                    850                 855                 860

Thr Thr Val Ala Pro Leu Phe Phe Ala Asp Gln Phe Leu Gln Leu Ser
    865                 870                 875                 880

Thr Ser Leu Pro Ser Gln Tyr Ile Thr Gly Leu Ala Glu His Leu Ser
                    885                 890                 895

Pro Leu Met Leu Ser Thr Ser Trp Thr Arg Ile Thr Leu Trp Asn Arg
                    900                 905                 910

Asp Leu Ala Pro Thr Pro Gly Ala Asn Leu Tyr Gly Ser His Pro Phe
                    915                 920                 925

Tyr Leu Ala Leu Glu Asp Gly Gly Ser Ala His Gly Val Phe Leu Leu
                    930                 935                 940

Asn Ser Asn Ala Met Asp Val Val Leu Gln Pro Ser Pro Ala Leu Ser
    945                 950                 955                 960

Trp Arg Ser Thr Gly Gly Ile Leu Asp Val Tyr Ile Phe Leu Gly Pro
                    965                 970                 975

Glu Pro Lys Ser Val Val Gln Gln Tyr Leu Asp Val Val Gly Tyr Pro
                    980                 985                 990

Phe Met Pro Pro Tyr Trp Gly Leu  Gly Phe His Leu Cys Arg Trp Gly
                    995                 1000                1005
```

```
Tyr Ser Ser Thr Ala Ile Thr Arg Gln Val Val Glu Asn Met Thr
    1010                1015                1020

Arg Ala His Phe Pro Leu Asp Val Gln Trp Asn Asp Leu Asp Tyr
    1025                1030                1035

Met Asp Ser Arg Arg Asp Phe Thr Phe Asn Lys Asp Gly Phe Arg
    1040                1045                1050

Asp Phe Pro Ala Met Val Gln Glu Leu His Gln Gly Gly Arg Arg
    1055                1060                1065

Tyr Met Met Ile Val Asp Pro Ala Ile Ser Ser Gly Pro Ala
    1070                1075                1080

Gly Ser Tyr Arg Pro Tyr Asp Glu Gly Leu Arg Arg Gly Val Phe
    1085                1090                1095

Ile Thr Asn Glu Thr Gly Gln Pro Leu Ile Gly Lys Val Trp Pro
    1100                1105                1110

Gly Ser Thr Ala Phe Pro Asp Phe Thr Asn Pro Thr Ala Leu Ala
    1115                1120                1125

Trp Trp Glu Asp Met Val Ala Glu Phe His Asp Gln Val Pro Phe
    1130                1135                1140

Asp Gly Met Trp Ile Asp Met Asn Glu Pro Ser Asn Phe Ile Arg
    1145                1150                1155

Gly Ser Glu Asp Gly Cys Pro Asn Asn Glu Leu Glu Asn Pro Pro
    1160                1165                1170

Tyr Val Pro Gly Val Val Gly Gly Thr Leu Gln Ala Ala Thr Ile
    1175                1180                1185

Cys Ala Ser Ser His Gln Phe Leu Ser Thr His Tyr Asn Leu His
    1190                1195                1200

Asn Leu Tyr Gly Leu Thr Glu Ala Ile Ala Ser His Arg Ala Leu
    1205                1210                1215

Val Lys Ala Arg Gly Thr Arg Pro Phe Val Ile Ser Arg Ser Thr
    1220                1225                1230

Phe Ala Gly His Gly Arg Tyr Ala Gly His Trp Thr Gly Asp Val
    1235                1240                1245

Trp Ser Ser Trp Glu Gln Leu Ala Ser Ser Val Pro Glu Ile Leu
    1250                1255                1260

Gln Phe Asn Leu Leu Gly Val Pro Leu Val Gly Ala Asp Val Cys
    1265                1270                1275

Gly Phe Leu Gly Asn Thr Ser Glu Glu Leu Cys Val Arg Trp Thr
    1280                1285                1290

Gln Leu Gly Ala Phe Tyr Pro Phe Met Arg Asn His Asn Ser Leu
    1295                1300                1305

Leu Ser Leu Pro Gln Glu Pro Tyr Ser Phe Ser Glu Pro Ala Gln
    1310                1315                1320

Gln Ala Met Arg Lys Ala Leu Thr Leu Arg Tyr Ala Leu Leu Pro
    1325                1330                1335

His Leu Tyr Thr Leu Phe His Gln Ala His Val Ala Gly Glu Thr
    1340                1345                1350

Val Ala Arg Pro Leu Phe Leu Glu Phe Pro Lys Asp Ser Ser Thr
    1355                1360                1365

Trp Thr Val Asp His Gln Leu Leu Trp Gly Glu Ala Leu Leu Ile
    1370                1375                1380

Thr Pro Val Leu Gln Ala Gly Lys Ala Glu Val Thr Gly Tyr Phe
    1385                1390                1395
```

-continued

```
Pro Leu Gly Thr Trp Tyr Asp Leu Gln Thr Val Pro Val Glu Ala
    1400            1405                1410

Leu Gly Ser Leu Pro Pro Pro Ala Ala Pro Arg Glu Pro Ala
    1415            1420                1425

Ile His Ser Glu Gly Gln Trp Val Thr Leu Pro Ala Pro Leu Asp
    1430            1435                1440

Thr Ile Asn Val His Leu Arg Ala Gly Tyr Ile Ile Pro Leu Gln
    1445            1450                1455

Gly Pro Gly Leu Thr Thr Thr Glu Ser Arg Gln Gln Pro Met Ala
    1460            1465                1470

Leu Ala Val Ala Leu Thr Lys Gly Gly Glu Ala Arg Gly Glu Leu
    1475            1480                1485

Phe Trp Asp Asp Gly Glu Ser Leu Glu Val Leu Glu Arg Gly Ala
    1490            1495                1500

Tyr Thr Gln Val Ile Phe Leu Ala Arg Asn Asn Thr Ile Val Asn
    1505            1510                1515

Glu Leu Val Arg Val Thr Ser Glu Gly Ala Gly Leu Gln Leu Gln
    1520            1525                1530

Lys Val Thr Val Leu Gly Val Ala Thr Ala Pro Gln Gln Val Leu
    1535            1540                1545

Ser Asn Gly Val Pro Val Ser Asn Phe Thr Tyr Ser Pro Asp Thr
    1550            1555                1560

Lys Val Leu Asp Ile Cys Val Ser Leu Leu Met Gly Glu Gln Phe
    1565            1570                1575

Leu Val Ser Trp Cys
    1580

<210> SEQ ID NO 21
<211> LENGTH: 1426
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ser Ile Pro Trp Asn Leu Glu Arg Ile Thr Pro Pro Arg Tyr Arg Ala
1               5                   10                  15

Asp Glu Tyr Gln Pro Pro Asp Gly Gly Ser Leu Val Glu Val Tyr Leu
                20                  25                  30

Leu Asp Thr Ser Ile Gln Ser Asp His Arg Glu Ile Glu Gly Arg Val
            35                  40                  45

Met Val Thr Asp Phe Glu Asn Val Pro Glu Glu Asp Gly Thr Arg Phe
        50                  55                  60

His Arg Gln Ala Ser Lys Cys Asp Ser His Gly Thr His Leu Ala Gly
65                  70                  75                  80

Val Val Ser Gly Arg Asp Ala Gly Val Ala Lys Gly Ala Ser Met Arg
                85                  90                  95

Ser Leu Arg Val Leu Asn Cys Gln Gly Lys Gly Thr Val Ser Gly Thr
            100                 105                 110

Leu Ile Gly Leu Glu Phe Ile Arg Lys Ser Gln Leu Val Gln Pro Val
        115                 120                 125

Gly Pro Leu Val Val Leu Leu Pro Leu Ala Gly Gly Tyr Ser Arg Val
    130                 135                 140

Leu Asn Ala Ala Cys Gln Arg Leu Ala Arg Ala Gly Val Val Leu Val
```

```
          145                 150                 155                 160
Thr Ala Ala Gly Asn Phe Arg Asp Asp Ala Cys Leu Tyr Ser Pro Ala
                    165                 170                 175

Ser Ala Pro Glu Val Ile Thr Val Gly Ala Thr Asn Ala Gln Asp Gln
                    180                 185                 190

Pro Val Thr Leu Gly Thr Leu Gly Thr Asn Phe Gly Arg Cys Val Asp
                    195                 200                 205

Leu Phe Ala Pro Gly Glu Asp Ile Ile Gly Ala Ser Ser Asp Cys Ser
                    210                 215                 220

Thr Cys Ala Val Ser Gln Ser Gly Thr Ala Gln Ala Ala His Val
225                 230                 235                 240

Ala Gly Ile Ala Ala Met Met Leu Ser Ala Glu Pro Glu Leu Thr Leu
                    245                 250                 255

Ala Glu Leu Arg Gln Arg Leu Ile His Phe Ser Ala Lys Asp Val Ile
                    260                 265                 270

Asn Glu Ala Trp Phe Pro Glu Asp Gln Arg Val Leu Thr Pro Asn Leu
                    275                 280                 285

Val Ala Ala Leu Pro Pro Ser Thr His Gly Ala Gly Trp Gln Leu Phe
                    290                 295                 300

Cys Arg Thr Val Trp Ser Ala His Ser Gly Pro Thr Arg Met Ala Thr
305                 310                 315                 320

Ala Val Ala Arg Cys Ala Pro Asp Glu Glu Leu Leu Ser Cys Ser Ser
                    325                 330                 335

Phe Ser Arg Ser Gly Lys Arg Gly Glu Arg Met Glu Ala Gln Gly
                    340                 345                 350

Gly Lys Leu Val Cys Arg Ala His Asn Ala Phe Gly Gly Glu Gly Val
                    355                 360                 365

Tyr Ala Ile Ala Arg Cys Cys Leu Leu Pro Gln Ala Asn Cys Ser Val
                    370                 375                 380

His Thr Ala Pro Pro Ala Glu Ala Ser Met Gly Thr Arg Val His Cys
385                 390                 395                 400

His Gln Gln Gly His Val Leu Thr Gly Cys Ser Ser His Trp Glu Val
                    405                 410                 415

Glu Asp Leu Gly Thr His Lys Pro Pro Val Leu Arg Pro Arg Gly Gln
                    420                 425                 430

Pro Asn Gln Cys Val Gly His Arg Glu Ala Ser Ile His Ala Ser Cys
                    435                 440                 445

Cys His Ala Pro Gly Leu Glu Cys Lys Val Lys Glu His Gly Ile Pro
450                 455                 460

Ala Pro Gln Glu Gln Val Thr Val Ala Cys Glu Glu Gly Trp Thr Leu
465                 470                 475                 480

Thr Gly Cys Ser Ala Leu Pro Gly Thr Ser His Val Leu Gly Ala Tyr
                    485                 490                 495

Ala Val Asp Asn Thr Cys Val Arg Ser Arg Asp Val Ser Thr Thr
                    500                 505                 510

Gly Ser Thr Ser Glu Gly Ala Val Thr Ala Val Ala Ile Cys Cys Arg
      515                 520                 525

Ser Arg His Leu Ala Gln Ala Ser Gln Glu Leu Gln Gly Gly Gly Ala
      530                 535                 540

His Pro Gly Arg Pro Arg Ala Val Pro Thr Gln Cys Asp Val Pro Pro
545                 550                 555                 560

Asn Ser Arg Phe Asp Cys Ala Pro Asp Lys Ala Ile Thr Gln Glu Gln
                    565                 570                 575
```

```
Cys Glu Ala Arg Gly Cys Cys Tyr Ile Pro Ala Lys Gln Gly Leu Gln
            580                 585                 590

Gly Ala Gln Met Gly Gln Pro Trp Cys Phe Phe Pro Ser Tyr Pro
        595                 600                 605

Ser Tyr Lys Leu Glu Asn Leu Ser Ser Ser Glu Met Gly Tyr Thr Ala
    610                 615                 620

Thr Leu Thr Arg Thr Thr Pro Thr Phe Phe Pro Lys Asp Ile Leu Thr
625                 630                 635                 640

Leu Arg Leu Asp Val Met Met Glu Thr Glu Asn Arg Leu His Phe Thr
                645                 650                 655

Ile Lys Asp Pro Ala Asn Arg Arg Tyr Glu Val Pro Leu Glu Thr Pro
            660                 665                 670

His Val His Ser Arg Ala Pro Ser Pro Leu Tyr Ser Val Glu Phe Ser
        675                 680                 685

Glu Glu Pro Phe Gly Val Ile Val Arg Arg Gln Leu Asp Gly Arg Val
    690                 695                 700

Leu Leu Asn Thr Thr Val Ala Pro Leu Phe Phe Ala Asp Gln Phe Leu
705                 710                 715                 720

Gln Leu Ser Thr Ser Leu Pro Ser Gln Tyr Ile Thr Gly Leu Ala Glu
                725                 730                 735

His Leu Ser Pro Leu Met Leu Ser Thr Ser Trp Thr Arg Ile Thr Leu
            740                 745                 750

Trp Asn Arg Asp Leu Ala Pro Thr Pro Gly Ala Asn Leu Tyr Gly Ser
        755                 760                 765

His Pro Phe Tyr Leu Ala Leu Glu Asp Gly Gly Ser Ala His Gly Val
    770                 775                 780

Phe Leu Leu Asn Ser Asn Ala Met Asp Val Val Leu Gln Pro Ser Pro
785                 790                 795                 800

Ala Leu Ser Trp Arg Ser Thr Gly Gly Ile Leu Asp Val Tyr Ile Phe
                805                 810                 815

Leu Gly Pro Glu Pro Lys Ser Val Val Gln Gln Tyr Leu Asp Val Val
            820                 825                 830

Gly Tyr Pro Phe Met Pro Pro Tyr Trp Gly Leu Gly Phe His Leu Cys
        835                 840                 845

Arg Trp Gly Tyr Ser Ser Thr Ala Ile Thr Arg Gln Val Val Glu Asn
    850                 855                 860

Met Thr Arg Ala His Phe Pro Leu Asp Val Gln Trp Asn Asp Leu Asp
865                 870                 875                 880

Tyr Met Asp Ser Arg Arg Asp Phe Thr Phe Asn Lys Asp Gly Phe Arg
                885                 890                 895

Asp Phe Pro Ala Met Val Gln Glu Leu His Gln Gly Arg Arg Tyr
            900                 905                 910

Met Met Ile Val Asp Pro Ala Ile Ser Ser Ser Gly Pro Ala Gly Ser
        915                 920                 925

Tyr Arg Pro Tyr Asp Glu Gly Leu Arg Arg Gly Val Phe Ile Thr Asn
    930                 935                 940

Glu Thr Gly Gln Pro Leu Ile Gly Lys Val Trp Pro Gly Ser Thr Ala
945                 950                 955                 960

Phe Pro Asp Phe Thr Asn Pro Thr Ala Leu Ala Trp Trp Glu Asp Met
                965                 970                 975

Val Ala Glu Phe His Asp Gln Val Pro Phe Asp Gly Met Trp Ile Asp
            980                 985                 990
```

```
Met Asn Glu Pro Ser Asn Phe Ile Arg Gly Ser Glu Asp Gly Cys Pro
            995                 1000                1005

Asn Asn Glu Leu Glu Asn Pro Pro Tyr Val Pro Gly Val Val Gly
        1010                1015                1020

Gly Thr Leu Gln Ala Ala Thr Ile Cys Ala Ser Ser His Gln Phe
        1025                1030                1035

Leu Ser Thr His Tyr Asn Leu His Asn Leu Tyr Gly Leu Thr Glu
        1040                1045                1050

Ala Ile Ala Ser His Arg Ala Leu Val Lys Ala Arg Gly Thr Arg
        1055                1060                1065

Pro Phe Val Ile Ser Arg Ser Thr Phe Ala Gly His Gly Arg Tyr
        1070                1075                1080

Ala Gly His Trp Thr Gly Asp Val Trp Ser Ser Trp Glu Gln Leu
        1085                1090                1095

Ala Ser Ser Val Pro Glu Ile Leu Gln Phe Asn Leu Leu Gly Val
        1100                1105                1110

Pro Leu Val Gly Ala Asp Val Cys Gly Phe Leu Gly Asn Thr Ser
        1115                1120                1125

Glu Glu Leu Cys Val Arg Trp Thr Gln Leu Gly Ala Phe Tyr Pro
        1130                1135                1140

Phe Met Arg Asn His Asn Ser Leu Leu Ser Leu Pro Gln Glu Pro
        1145                1150                1155

Tyr Ser Phe Ser Glu Pro Ala Gln Gln Ala Met Arg Lys Ala Leu
        1160                1165                1170

Thr Leu Arg Tyr Ala Leu Leu Pro His Leu Tyr Thr Leu Phe His
        1175                1180                1185

Gln Ala His Val Ala Gly Glu Thr Val Ala Arg Pro Leu Phe Leu
        1190                1195                1200

Glu Phe Pro Lys Asp Ser Ser Thr Trp Thr Val Asp His Gln Leu
        1205                1210                1215

Leu Trp Gly Glu Ala Leu Leu Ile Thr Pro Val Leu Gln Ala Gly
        1220                1225                1230

Lys Ala Glu Val Thr Gly Tyr Phe Pro Leu Gly Thr Trp Tyr Asp
        1235                1240                1245

Leu Gln Thr Val Pro Val Glu Ala Leu Gly Ser Leu Pro Pro Pro
        1250                1255                1260

Pro Ala Ala Pro Arg Glu Pro Ala Ile His Ser Glu Gly Gln Trp
        1265                1270                1275

Val Thr Leu Pro Ala Pro Leu Asp Thr Ile Asn Val His Leu Arg
        1280                1285                1290

Ala Gly Tyr Ile Ile Pro Leu Gln Gly Pro Gly Leu Thr Thr Thr
        1295                1300                1305

Glu Ser Arg Gln Gln Pro Met Ala Leu Ala Val Ala Leu Thr Lys
        1310                1315                1320

Gly Gly Glu Ala Arg Gly Glu Leu Phe Trp Asp Asp Gly Glu Ser
        1325                1330                1335

Leu Glu Val Leu Glu Arg Gly Ala Tyr Thr Gln Val Ile Phe Leu
        1340                1345                1350

Ala Arg Asn Asn Thr Ile Val Asn Glu Leu Val Arg Val Thr Ser
        1355                1360                1365

Glu Gly Ala Gly Leu Gln Leu Gln Lys Val Thr Val Leu Gly Val
        1370                1375                1380

Ala Thr Ala Pro Gln Gln Val Leu Ser Asn Gly Val Pro Val Ser
```

```
             1385                1390                1395
Asn Phe Thr Tyr Ser Pro Asp Thr Lys Val Leu Asp Ile Cys Val
    1400                1405                1410
Ser Leu Leu Met Gly Glu Gln Phe Leu Val Ser Trp Cys
    1415                1420                1425

<210> SEQ ID NO 22
<211> LENGTH: 1263
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Asp Glu Ala Arg Glu Ala Ala Val Arg Ala Leu Val Ala Arg Leu
1               5                   10                  15

Leu Gly Pro Gly Pro Ala Ala Asp Phe Ser Val Ser Val Glu Arg Ala
            20                  25                  30

Leu Ala Ala Lys Pro Gly Leu Asp Thr Tyr Ser Leu Gly Gly Gly Gly
        35                  40                  45

Ala Ala Arg Val Arg Val Arg Gly Ser Thr Gly Val Ala Ala Ala Ala
    50                  55                  60

Gly Leu His Arg Tyr Leu Arg Asp Phe Cys Gly Cys His Val Ala Trp
65              70                  75                  80

Ser Gly Ser Gln Leu Arg Leu Pro Arg Pro Leu Pro Ala Val Pro Gly
                85                  90                  95

Glu Leu Thr Glu Ala Thr Pro Asn Arg Tyr Arg Tyr Gln Asn Val
            100                 105                 110

Cys Thr Gln Ser Tyr Ser Phe Val Trp Trp Asp Trp Ala Arg Trp Glu
        115                 120                 125

Arg Glu Ile Asp Trp Met Ala Leu Asn Gly Ile Asn Leu Ala Leu Ala
    130                 135                 140

Trp Ser Gly Gln Glu Ala Ile Trp Gln Arg Val Tyr Leu Ala Leu Gly
145             150                 155                 160

Leu Thr Gln Ala Glu Ile Asn Glu Phe Phe Thr Gly Pro Ala Phe Leu
                165                 170                 175

Ala Trp Gly Arg Met Gly Asn Leu His Thr Trp Asp Gly Pro Leu Pro
            180                 185                 190

Pro Ser Trp His Ile Lys Gln Leu Tyr Leu Gln His Arg Val Leu Asp
        195                 200                 205

Gln Met Arg Ser Phe Gly Met Thr Pro Val Leu Pro Ala Phe Ala Gly
    210                 215                 220

His Val Pro Glu Ala Val Thr Arg Val Phe Pro Gln Val Asn Val Thr
225             230                 235                 240

Lys Met Gly Ser Trp Gly His Phe Asn Cys Ser Tyr Ser Cys Ser Phe
                245                 250                 255

Leu Leu Ala Pro Glu Asp Pro Ile Phe Pro Ile Ile Gly Ser Leu Phe
            260                 265                 270

Leu Arg Glu Leu Ile Lys Glu Phe Gly Thr Asp His Ile Tyr Gly Ala
        275                 280                 285

Asp Thr Phe Asn Glu Met Gln Pro Pro Ser Ser Glu Pro Ser Tyr Leu
    290                 295                 300

Ala Ala Ala Thr Thr Ala Val Tyr Glu Ala Met Thr Ala Val Asp Thr
305             310                 315                 320
```

```
Glu Ala Val Trp Leu Leu Gln Gly Trp Leu Phe Gln His Gln Pro Gln
                325                 330                 335

Phe Trp Gly Pro Ala Gln Ile Arg Ala Val Leu Gly Ala Val Pro Arg
        340                 345                 350

Gly Arg Leu Leu Val Leu Asp Leu Phe Ala Glu Ser Gln Pro Val Tyr
                355                 360                 365

Thr Arg Thr Ala Ser Phe Gln Gly Gln Pro Phe Ile Trp Cys Met Leu
    370                 375                 380

His Asn Phe Gly Gly Asn His Gly Leu Phe Gly Ala Leu Glu Ala Val
385                 390                 395                 400

Asn Gly Gly Pro Glu Ala Ala Arg Leu Phe Pro Asn Ser Thr Met Val
                405                 410                 415

Gly Thr Gly Met Ala Pro Glu Gly Ile Ser Gln Asn Glu Val Val Tyr
                420                 425                 430

Ser Leu Met Ala Glu Leu Gly Trp Arg Lys Asp Pro Val Pro Asp Leu
            435                 440                 445

Ala Ala Trp Val Thr Ser Phe Ala Ala Arg Arg Tyr Gly Val Ser His
        450                 455                 460

Pro Asp Ala Gly Ala Ala Trp Arg Leu Leu Arg Ser Val Tyr Asn
465                 470                 475                 480

Cys Ser Gly Glu Ala Cys Arg Gly His Asn Arg Ser Pro Leu Val Arg
                485                 490                 495

Arg Pro Ser Leu Gln Met Asn Thr Ser Ile Trp Tyr Asn Arg Ser Asp
            500                 505                 510

Val Phe Glu Ala Trp Arg Leu Leu Thr Ser Ala Pro Ser Leu Ala
            515                 520                 525

Thr Ser Pro Ala Phe Arg Tyr Asp Leu Leu Asp Leu Thr Arg Gln Ala
    530                 535                 540

Val Gln Glu Leu Val Ser Leu Tyr Tyr Glu Glu Ala Arg Ser Ala Tyr
545                 550                 555                 560

Leu Ser Lys Glu Leu Ala Ser Leu Leu Arg Ala Gly Val Leu Ala
                565                 570                 575

Tyr Glu Leu Leu Pro Ala Leu Asp Glu Val Leu Ala Ser Asp Ser Arg
            580                 585                 590

Phe Leu Leu Gly Ser Trp Leu Glu Gln Ala Arg Ala Ala Val Ser
            595                 600                 605

Glu Ala Glu Ala Asp Phe Tyr Glu Gln Asn Ser Arg Tyr Gln Leu Thr
    610                 615                 620

Leu Trp Gly Pro Glu Gly Asn Ile Leu Asp Tyr Ala Asn Lys Gln Leu
625                 630                 635                 640

Ala Gly Leu Val Ala Asn Tyr Tyr Thr Pro Arg Trp Arg Leu Phe Leu
                645                 650                 655

Glu Ala Leu Val Asp Ser Val Ala Gln Gly Ile Pro Phe Gln Gln His
                660                 665                 670

Gln Phe Asp Lys Asn Val Phe Gln Leu Glu Gln Ala Phe Val Leu Ser
            675                 680                 685

Lys Gln Arg Tyr Pro Ser Gln Pro Arg Gly Asp Thr Val Asp Leu Ala
    690                 695                 700

Lys Lys Ile Phe Leu Lys Tyr Tyr Pro Arg Trp Val Ala Gly Ser Trp
705                 710                 715                 720

Gly Gly Gly Ser Ile Pro Trp Asn Leu Glu Arg Ile Thr Pro Pro Arg
                725                 730                 735
```

-continued

Tyr Arg Ala Asp Glu Tyr Gln Pro Pro Asp Gly Gly Ser Leu Val Glu
        740                     745                 750

Val Tyr Leu Leu Asp Thr Ser Ile Gln Ser Asp His Arg Glu Ile Glu
        755                 760                 765

Gly Arg Val Met Val Thr Asp Phe Glu Asn Val Pro Glu Glu Asp Gly
        770                 775                 780

Thr Arg Phe His Arg Gln Ala Ser Lys Cys Asp Ser His Gly Thr His
785                 790                 795                 800

Leu Ala Gly Val Val Ser Gly Arg Asp Ala Gly Val Ala Lys Gly Ala
                805                 810                 815

Ser Met Arg Ser Leu Arg Val Leu Asn Cys Gln Gly Lys Gly Thr Val
                820                 825                 830

Ser Gly Thr Leu Ile Gly Leu Glu Phe Ile Arg Lys Ser Gln Leu Val
                835                 840                 845

Gln Pro Val Gly Pro Leu Val Val Leu Leu Pro Leu Ala Gly Gly Tyr
                850                 855                 860

Ser Arg Val Leu Asn Ala Ala Cys Gln Arg Leu Ala Arg Ala Gly Val
865                 870                 875                 880

Val Leu Val Thr Ala Ala Gly Asn Phe Arg Asp Asp Ala Cys Leu Tyr
                885                 890                 895

Ser Pro Ala Ser Ala Pro Glu Val Ile Thr Val Gly Ala Thr Asn Ala
                900                 905                 910

Gln Asp Gln Pro Val Thr Leu Gly Thr Leu Gly Thr Asn Phe Gly Arg
                915                 920                 925

Cys Val Asp Leu Phe Ala Pro Gly Glu Asp Ile Ile Gly Ala Ser Ser
                930                 935                 940

Asp Cys Ser Thr Cys Ala Val Ser Gln Ser Gly Thr Ala Gln Ala Ala
945                 950                 955                 960

Ala His Val Ala Gly Ile Ala Ala Met Met Leu Ser Ala Glu Pro Glu
                965                 970                 975

Leu Thr Leu Ala Glu Leu Arg Gln Arg Leu Ile His Phe Ser Ala Lys
                980                 985                 990

Asp Val Ile Asn Glu Ala Trp Phe Pro Glu Asp Gln Arg Val Leu Thr
                995                 1000                1005

Pro Asn Leu Val Ala Ala Leu Pro Pro Ser Thr His Gly Ala Gly
    1010                1015                1020

Trp Gln Leu Phe Cys Arg Thr Val Trp Ser Ala His Ser Gly Pro
    1025                1030                1035

Thr Arg Met Ala Thr Ala Val Ala Arg Cys Ala Pro Asp Glu Glu
    1040                1045                1050

Leu Leu Ser Cys Ser Ser Phe Ser Arg Ser Gly Lys Arg Arg Gly
    1055                1060                1065

Glu Arg Met Glu Ala Gln Gly Gly Lys Leu Val Cys Arg Ala His
    1070                1075                1080

Asn Ala Phe Gly Gly Glu Gly Val Tyr Ala Ile Ala Arg Cys Cys
    1085                1090                1095

Leu Leu Pro Gln Ala Asn Cys Ser Val His Thr Ala Pro Pro Ala
    1100                1105                1110

Glu Ala Ser Met Gly Thr Arg Val His Cys His Gln Gln Gly His
    1115                1120                1125

Val Leu Thr Gly Cys Ser Ser His Trp Glu Val Glu Asp Leu Gly
    1130                1135                1140

Thr His Lys Pro Pro Val Leu Arg Pro Arg Gly Gln Pro Asn Gln

-continued

```
              1145              1150              1155
Cys Val Gly His Arg Glu Ala Ser Ile His Ala Ser Cys Cys His
            1160              1165              1170

Ala Pro Gly Leu Glu Cys Lys Val Lys Glu His Gly Ile Pro Ala
            1175              1180              1185

Pro Gln Glu Gln Val Thr Val Ala Cys Glu Glu Gly Trp Thr Leu
            1190              1195              1200

Thr Gly Cys Ser Ala Leu Pro Gly Thr Ser His Val Leu Gly Ala
            1205              1210              1215

Tyr Ala Val Asp Asn Thr Cys Val Val Arg Ser Arg Asp Val Ser
            1220              1225              1230

Thr Thr Gly Ser Thr Ser Glu Gly Ala Val Thr Ala Val Ala Ile
            1235              1240              1245

Cys Cys Arg Ser Arg His Leu Ala Gln Ala Ser Gln Glu Leu Gln
            1250              1255              1260

<210> SEQ ID NO 23
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Gln Glu Asp Glu Asp Gly Asp Tyr Glu Glu Leu Val Leu Ala Leu Arg
1               5                   10                  15

Ser Glu Glu Asp Gly Leu Ala Glu Ala Pro Glu His Gly Thr Thr Ala
                20                  25                  30

Thr Phe His Arg Cys Ala Lys Asp Pro Trp Arg Leu Pro Gly Thr Tyr
            35                  40                  45

Val Val Val Leu Lys Glu Thr His Leu Ser Gln Ser Glu Arg Thr
        50                  55                  60

Ala Arg Arg Leu Gln Ala Gln Ala Ala Arg Arg Gly Tyr Leu Thr Lys
65                  70                  75                  80

Ile Leu His Val Phe His Gly Leu Leu Pro Gly Phe Leu Val Lys Met
                85                  90                  95

Ser Gly Asp Leu Leu Glu Leu Ala Leu Lys Leu Pro His Val Asp Tyr
                100                 105                 110

Ile Glu Glu Asp Ser Ser Val Phe Ala Gln
                115                 120
```

UNITED STATES PATENT AND TRADEMARK OFFICE
CERTIFICATE OF CORRECTION

PATENT NO. : 10,556,015 B2
APPLICATION NO. : 15/521130
DATED : February 11, 2020
INVENTOR(S) : Zhang et al.

Page 1 of 1

It is certified that error appears in the above-identified patent and that said Letters Patent is hereby corrected as shown below:

On the Title Page

Item (73) Under Assignee, please delete "Criteo S.A., Paris (FR)" and insert --"Shire Human Genetic Therapies, Inc., Lexington, MA (US)"--.

Signed and Sealed this
Twenty-eighth Day of July, 2020

Andrei Iancu
*Director of the United States Patent and Trademark Office*